United States Patent
Hagen et al.

(10) Patent No.: US 10,973,899 B2
(45) Date of Patent: Apr. 13, 2021

(54) FLAVIVIRUS REPLICONS

(71) Applicant: NOVARTIS AG, Basel (CH)

(72) Inventors: Caitlin Jeanette Hagen, Cambridge, MA (US); Dong Yu, Cambridge, MA (US); Peter W. Mason, New York, NY (US); Peter Shahinian, Cambridge, MA (US)

(73) Assignee: Novartis AG, Basel (CH)

( * ) Notice: Subject to any disclaimer, the term of this patent is extended or adjusted under 35 U.S.C. 154(b) by 326 days.

(21) Appl. No.: 15/554,139

(22) PCT Filed: Feb. 25, 2016

(86) PCT No.: PCT/IB2016/051045
§ 371 (c)(1),
(2) Date: Aug. 28, 2017

(87) PCT Pub. No.: WO2016/135675
PCT Pub. Date: Sep. 1, 2016

(65) Prior Publication Data
US 2018/0036398 A1    Feb. 8, 2018

(30) Foreign Application Priority Data

Feb. 27, 2015  (EP) .................................. 15157068

(51) Int. Cl.
*A61K 39/02* (2006.01)
*C12N 15/86* (2006.01)
*A61K 39/00* (2006.01)

(52) U.S. Cl.
CPC .............. *A61K 39/02* (2013.01); *C12N 15/86* (2013.01); *A61K 2039/53* (2013.01); *C12N 2770/24143* (2013.01); *Y02A 50/30* (2018.01)

(58) Field of Classification Search
None
See application file for complete search history.

(56) References Cited

U.S. PATENT DOCUMENTS

| 8,399,423 B2* | 3/2013 | Kandimalla | A61K 31/711 514/44 R |
| 2006/0062806 A1* | 3/2006 | Barrett | C12N 7/00 424/204.1 |

FOREIGN PATENT DOCUMENTS

| WO | 99/28487 A1 | 6/1999 |
| WO | WO 2004/040263 A2 * | 10/2003 |
| WO | 2006/086838 A1 | 8/2006 |
| WO | 2011/049677 A1 | 4/2011 |

OTHER PUBLICATIONS

Jones et al. "Construction and applications of yellow fever virus replicons" Virology, 2005; 331: 247-259.*
Schirrmacher et al. Intra-pinna anti-tumor vaccination with self-replicating infectious RNA or with DNA encoding a model tumor antigen and a cytokine, Gene Therapy, 2000; 7: 1137-1147.*
Varnavski et al. Stable High-Level Expression of Heterologous Genes In Vitro and In Vivo by Noncytopathic DNA-Based Kunjin Virus Replicon Vectors, J. Virol. 2000; 74(9) 4394-4403.*
Queiroz et al. "Construction of yellow fever virus subgenomic replicons by yeast-based homologous recombination cloning technique", Anais Da Academia Brasileira De Ciencias, 2013; 85; 1: 159-168.*
Coleman et al..Nucleic Acids Research, 2004, vol. 32, No. 1 e14 (Year: 2004).*
Jerzak et al., Virology 360 (2007) 469-476 (Year: 2007).*
Queiroz et al. "Construction of yellow fever virus subgenomic replicons by yeast-based homologous recombination cloning technique", Anais Da Academia Brasileira De Ciencias, 2013; 85; 1: 159-168 (Year: 2013).*
Pijlman et al., Expert Opin. Biol. Ther. (2006) 6(2):135-145 (Year: 2006).*
International Search Report and Written Opinion of International Application No. PCT/IB2016/051045 dated May 3, 2016. 14 pages.
Alcaraz-Estrada, Sofia L. et al. "Construction of Self-Replicating Subgenomic West Nile Virus Replicons for Screening Antiviral Compounds." Methods in Molecular Biology. vol. 1030, Jan. 1, 2013, pp. 283-299. XP009185841.
Queiroz, Sabrina R.A. et al. "Construction of yellow fever virus subgenomic replicons by yeast-based homologous recombination cloning technique." Anais Da Academia Brasileira De Cinecias. vol. 85, No. 1, Jan. 1, 2013, pp. 159-168. XP055209438.
Jones, Christopher T. et al. "Construction and applications of yellow fever virus replicons." Virology. Elsevier, Amsterdam, NL. vol. 331, No. 2, Jan. 20, 2005, pp. 247-259. XP004701402.
Herd, Karen A. et al. "Recombinant Kunjin virus replicon vaccines induce protective T-cell immunity against human papillomavirus 16 E7-expressing tumour." Virology. Elsevier, vol. 319, No. 2, Feb. 20, 2004, pp. 237-248. XP004491671.
Varnavski, Andrei N. et al. "Noncytopathic Flavivirus Replicon RNA-Based System for Expression and Delivery of Heterologous Genes." Virology. vol. 255, No. 2, Mar. 15, 1999, pp. 366-375. XP004440024.

(Continued)

*Primary Examiner* — Shanon A. Foley
*Assistant Examiner* — Myron G Hill
(74) *Attorney, Agent, or Firm* — Linyu L. Mitra

(57) ABSTRACT

The invention provides, inter alia, improved replicons and vectors encoding them, where the replicons provide sustained expression of an encoded protein. These replicons comprise flavivirus replicases and heterologous protein coding sequences, wherein the heterologous protein coding sequences are flanked by separation sequences for improved efficacy. These nucleic acids provided by the invention, including self-replicating RNAs provided by the invention, are useful in methods of protein expression, such as for vaccines (e.g., for methods of immunization), as well as expression of therapeutic proteins, such as antibodies (e.g., for methods of treatment).

13 Claims, 28 Drawing Sheets
Specification includes a Sequence Listing.

(56) References Cited

OTHER PUBLICATIONS

Anraku et al., "Kunjin Virus Replicon Vaccine Vectors Induce Protective CD8+ T Cell Immunity", Journal of Virology, 2002, 76(8):3791-3799.
Paul, et al., "Selection of a T7 promoter mutant with enhanced in vitro activity by a novel multo-copy bead display aproach for in vitro evolution", Nucleic Acids Research, 2013, 41(1):e29, 1-11.
Ray et al., "West Nile Virus 5'-Cap Structure is Formed by Sequencial Guanine N-7 and Ribose 2'-O Methylations by Nonstructural Protein 5", Journal of Virology, 2006, 80(7): 8362-8370.
Takasaki, "West Nile fever/encephalitis", Virus, 2007, vol. 57, No. 2, p. 199-206.

\* cited by examiner

FIG. 1

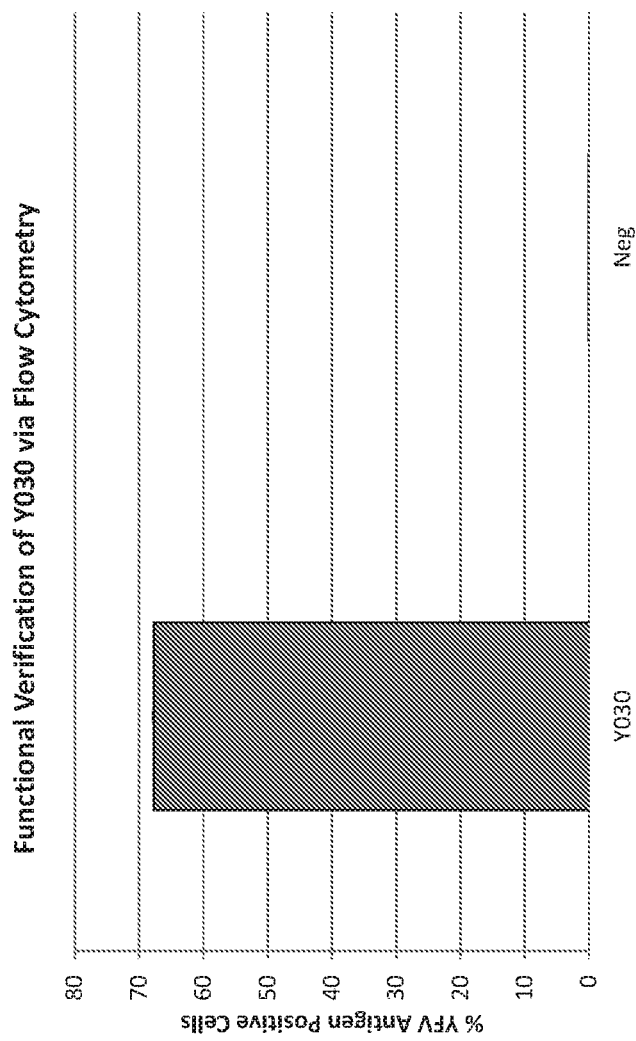

FIG. 4A:
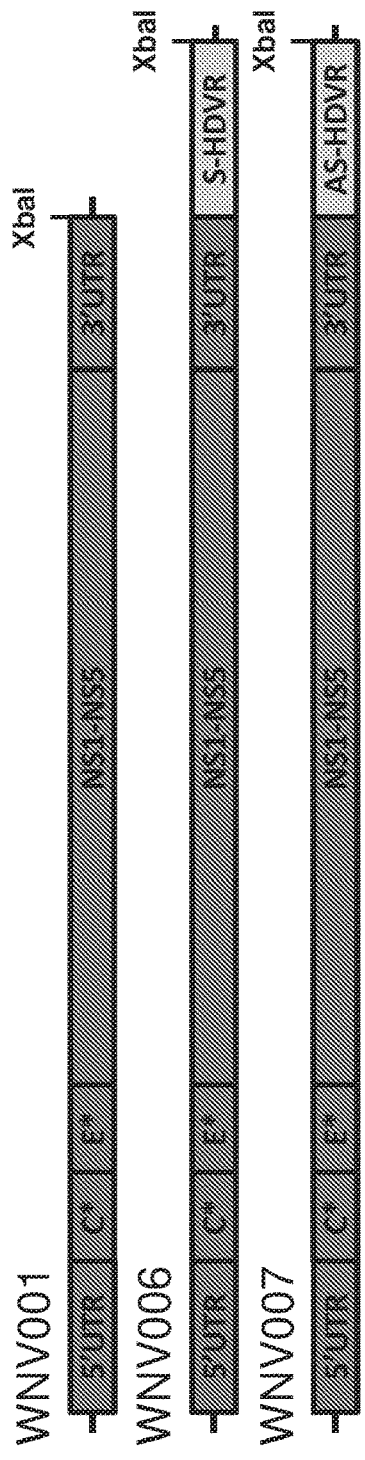
FIG. 4B
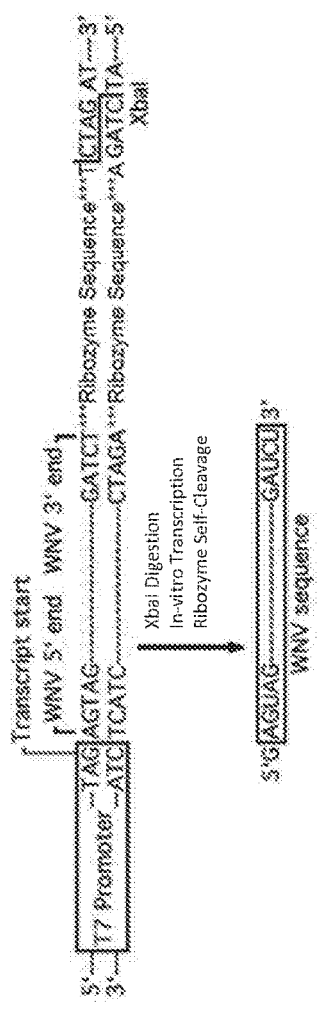
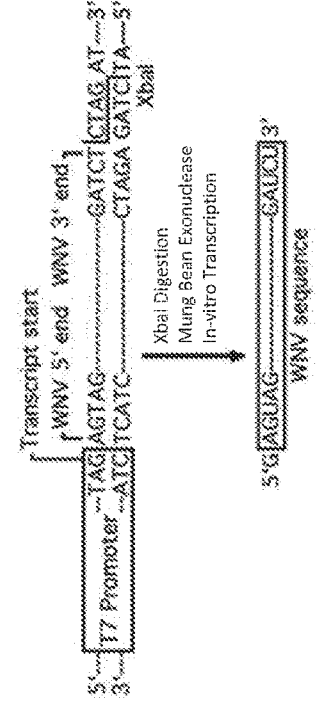

FIG. 5:

Addition of HDVR significantly improves WNV replicon potency

| Promoter | Sequence | Construct |
|---|---|---|
| T7 promoter φ6.5 | TAATACGACTCACTATAGA--- | WNV008* or Y037 |
| T7 promoter φ2.5 | TAATACGACTCACTATTAA--- | WNV017 or Y042 |
| T7 promoter φ6.5 mut | TAATACGACTCACTATAAA--- | WNV026 or Y043 |
| T7 promoter φ2.5 (OL) | TAATACGACTCACTATTA--- | WNV027 or Y044 |
| T7 promoter φ6.5 mut (OL) | TAATACGACTCACTATAA--- | WNV028 or Y045 |

B

| Replicon RNA | RNA Yield * (µg) |
|---|---|
| WNV008 | 100% |
| WNV017 | 7% |
| WNV026 | 1.5% |
| WNV027 | 64% |
| WNV028 | 82% |

C

| Replicon RNA | RNA Yield * (% yield compared to T7 promoter φ6.5) |
|---|---|
| Y037 | 100 % |
| Y042 | 64 % |
| Y043 | 59 % |
| Y044 | 62 % |
| Y045 | 61 % |

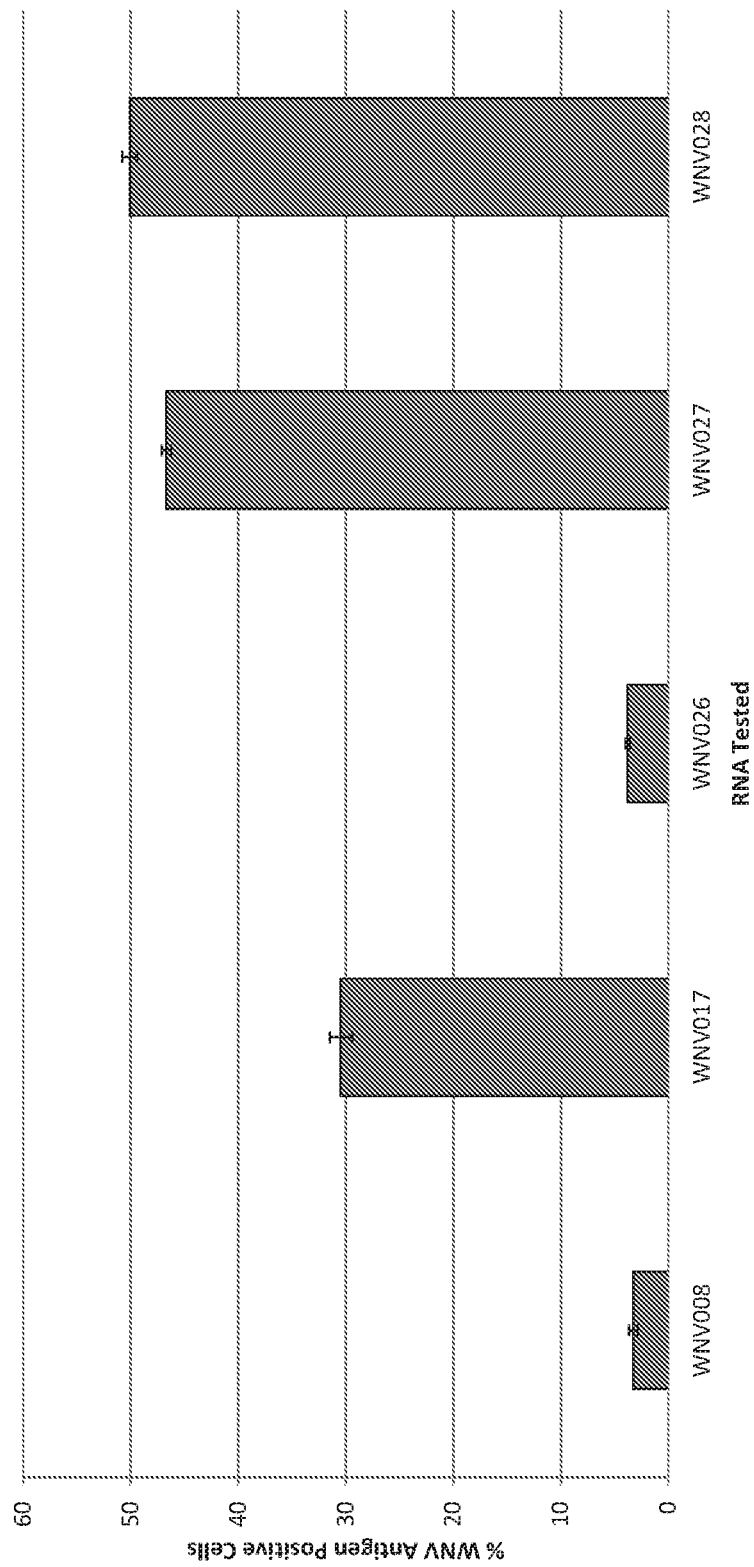

FIG. 10:

Modified Promoters Driving Transcription of
YFV Replicon RNA Enhance Potency

FIG. 12:
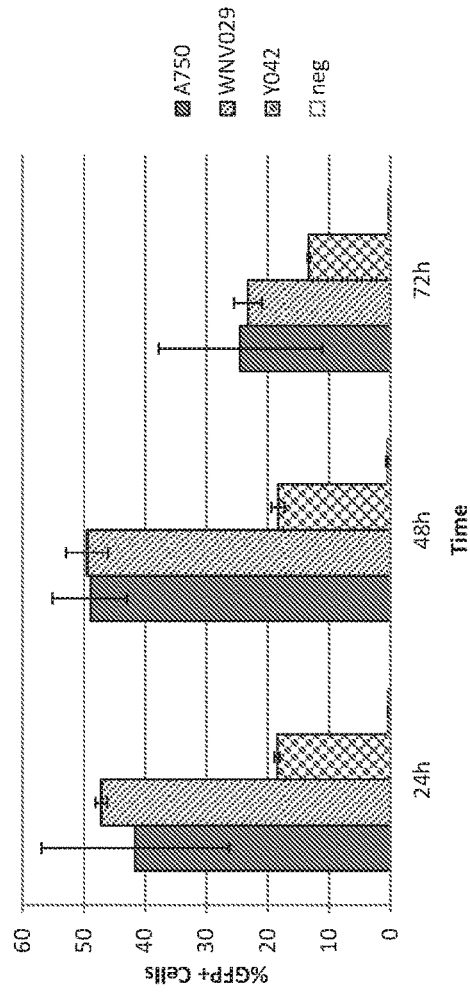
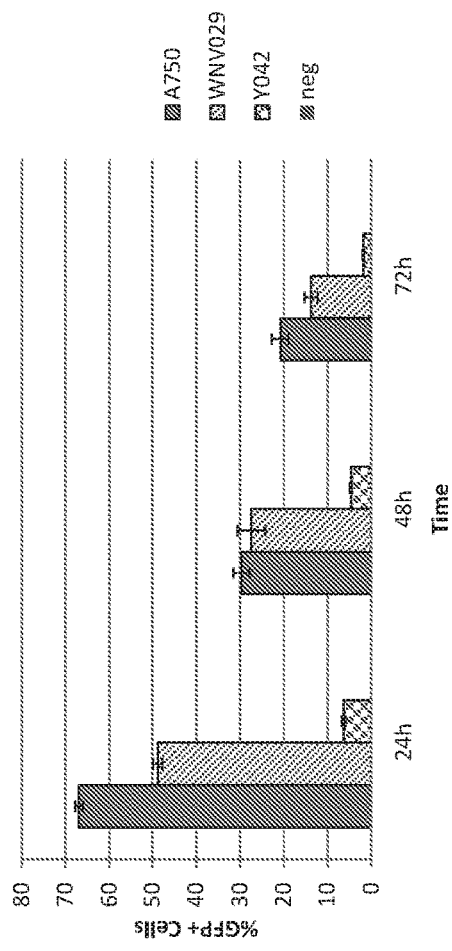

Addition of HDVR significantly improves WNV replicon potency

FIG. 16

1ug RNA Electroporation
%WNV+

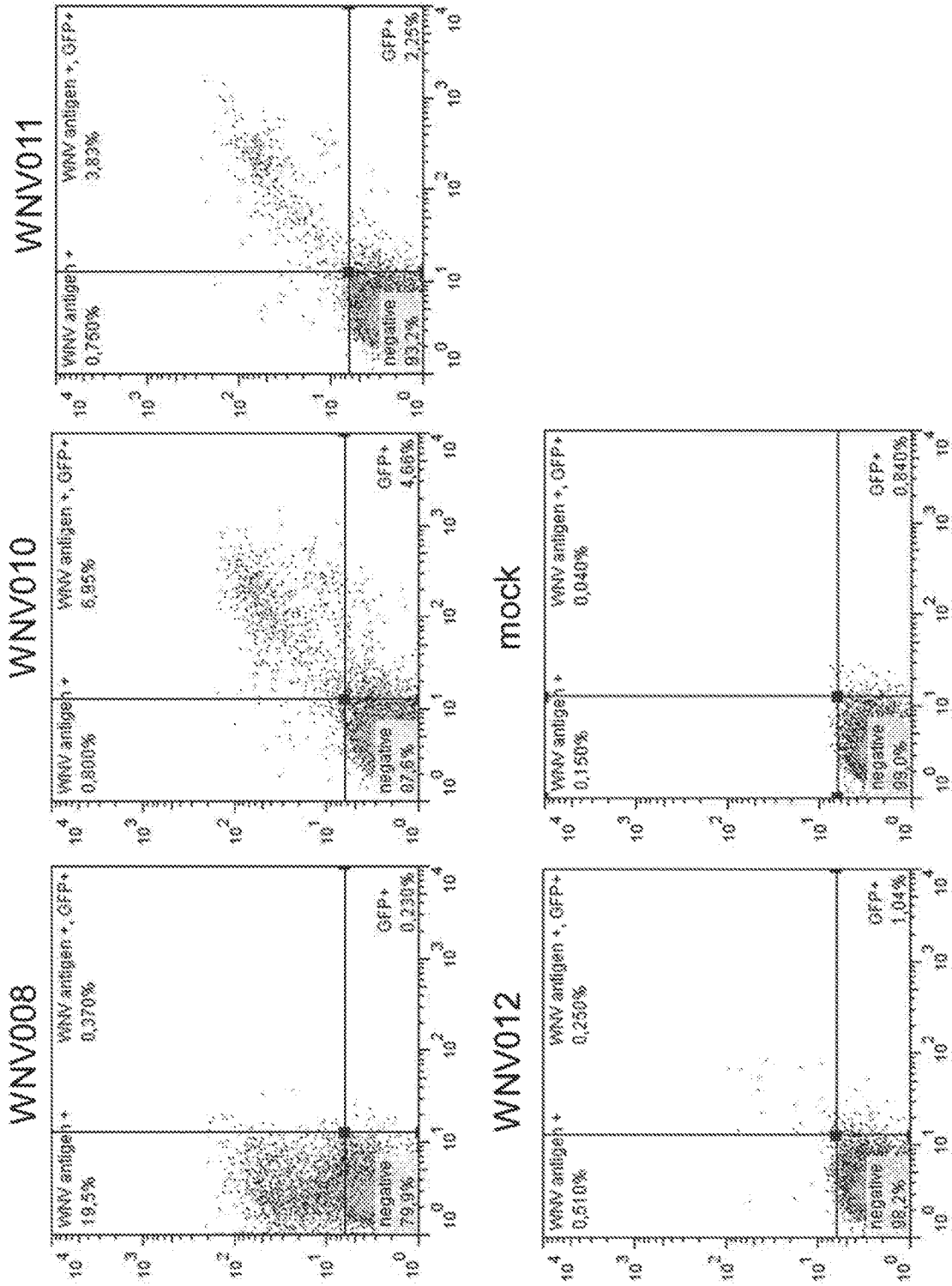

FIG. 19C

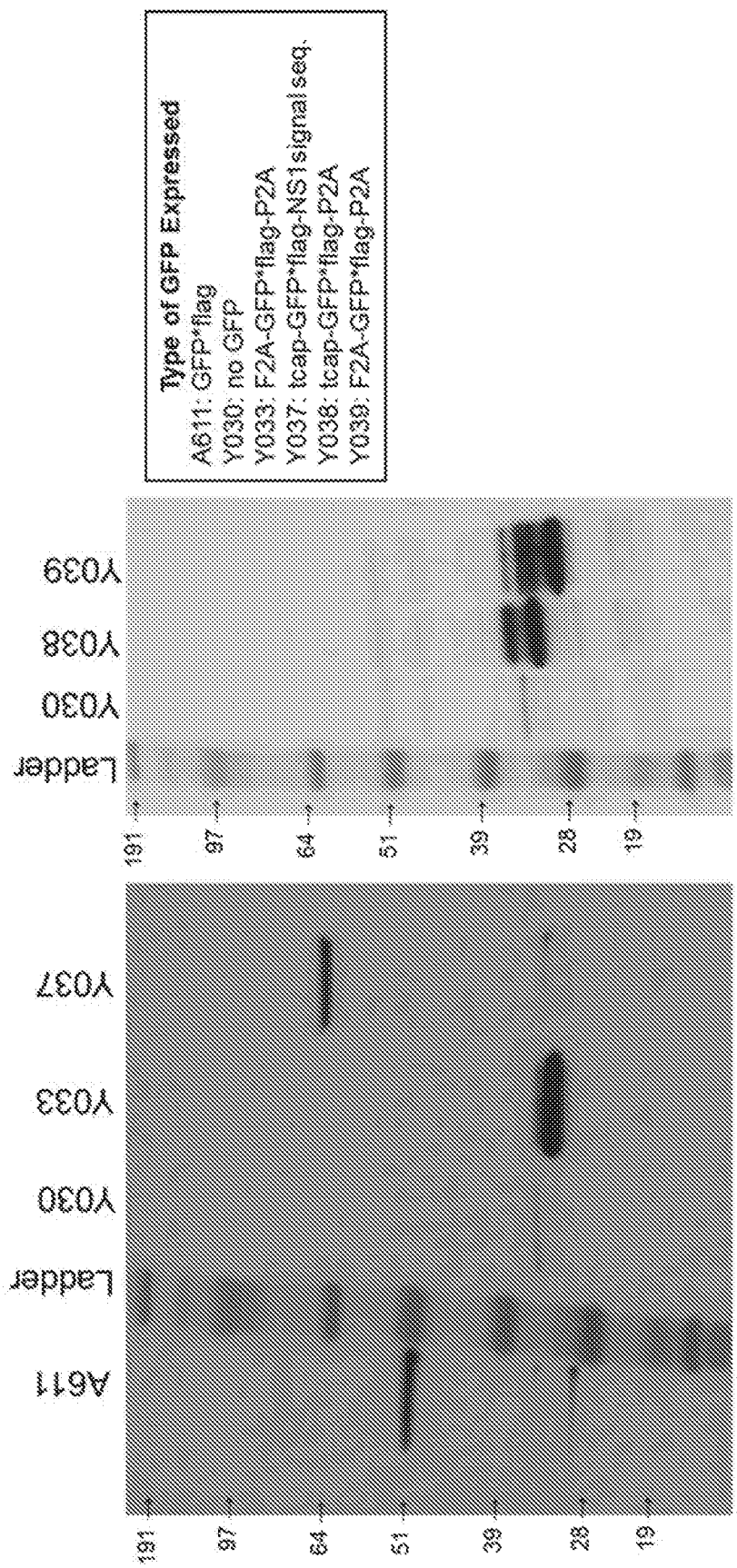

FIG. 23

A. Addition of GFP*FLAG or FLUC casettes into WNV replicon reduces potency

B. The insertion of scFv-hFc reporter genes into WNV constructs further reduces potency

SEQUENCE LISTING

```
<160> NUMBER OF SEQ ID NOS: 27

<210> SEQ ID NO 1
<211> LENGTH: 8839
<212> TYPE: DNA
<213> ORGANISM: West Nile virus

<400> SEQUENCE: 1
agtagttcgc ctgtgtgagc tgacaaactt agtagtgttt gtgaggatta acaacaatta    60
acacagtgcg agctgtttct tagcacgaag atctcgatgc taagaaaacc aggagggccc   120
ggcaagagcc gggctgtcaa tatgctaaaa cgcggaatgc ccgcgtgtt gtccttgatt    180
```

```
ggacttaaga tgggcatcaa tgctcgtgat aggtccatag ctctcacgtt tctcgcagtt    240
ggaggagttc tgctcttcct ctccgtgaac gtgcacgctg acactgggtg tgccatagac    300
atcagccggc aagagctgag atgtggaagt ggagtgttca tacacaatga tgtggaggct    360
tggatggacc gatacaagta ttaccctgaa acgccacaag gcctagccaa gatcattcag    420
aaagctcata aggaaggagt gtgcggtcta cgatcagttt ccagactgga gcatcaaatg    480
tgggaagcag tgaaggacga gctgaacact cttttgaagg agaatggtgt ggaccttagt    540
gtcgtggttg agaaacagga gggaatgtac aagtcagcac ctaaacgcct caccgccacc    600
acggaaaaat tggaaattgg ctggaaggcc tggggaaaga gtattttatt tgcaccagaa    660
ctcgccaaca acacctttgt ggttgatggt ccggagacca aggaatgtcc gactcagaat    720
cgcgcttgga atagcttaga agtggaggat tttggatttg gtctcaccag cactcggatg    780
ttcctgaagg tcagagagag caacacaact gaatgtgact cgaagatcat ggaacggct     840 gtcaagaaca acttggcgat ccacagtgac ctgtcctatt ggattgaaag caggctcaat    900
gatacgtgga agcttgaaag ggcagttctg ggtgaagtca aatcatgtac gtggcctgag    960
acgcatacct tgtggggcga tggaatcctt gagagtgact tgataatacc agtcacactg    1020
gcgggaccac gaagcaatca caatcggaga cctgggtaca agacacaaaa ccagggccca    1080
tgggacgaag gccgggtaga gattgacttc gattactgcc caggaactac ggtcacctg    1140 agtgagagct cgcgacaccg tggacctgcc actcgcacca ccacagagag cggaaagttg    1200
ataacagatt ggtgctgcag gagctgcacc ttaccaccac tgcgctacca aactgacagc    1260
ggctgttggt atggtatgga gatcagacca cagagacatg atgaaaagac cctcgtgcag    1320
tcacaagtga atgcttataa tgctgatatg attgacccct tcagttgggg ccttctggtc    1380
gtgttcttgg ccacccagga ggtccttcgc aagaggtgga cagccaagat cagcatgcca    1440
gctatactga ttgctctgct agtcctggtg tttgggggca ttacttacac tgatgtgtta    1500
cgctatgtca tcttggtggg ggcagctttc gcagaatcta attcgggagg agacgtggta    1560
cacttggcgc tcatggcgac cttcaagata caaccagtgt ttatggtggc atcgtttctc    1620
aaagcgagat ggaccaacca ggagaacatt ttgttgatgt tggcggctgt tttcttcaa    1680 atggcttatc acgatgcccg ccaaattctg ctctgggaga tccctgatgt gttgaattca    1740
ctggcggtag cttggatgat actgagagcc ataacattca aacgacatc aaacgtggtt    1800 gttccgctgc tagccctgct aacacccggg ctgagatgct tgaatctgga tgtgtacagg    1860
atactgctgt tgatggtcgg aataggcagc ttgatcaggg agaagaggag tgcagctgca    1920
aaaaagaaag gagcaagtct gctatgcttg gctctagcct caacaggact tttcaacccc    1980
atgatccttg ctgctggact gattacatgt gatcccaacc gtaaacgcgg atggcccgca    2040
actgaagtga tgacagctgt cggcctgatg tttgccatcg tcggagggct ggcagagctt    2100
gacattgact ccatggccat tccaatgact atcgcggggc tcatgtttgc tgctttcgtg    2160
atttctggga aatcaacaga tatgtggatt gagagaacgg cggacattc ctgggaaagt    2220 gatgcagaaa ttacaggctc gagcgaaaga gttgatgtgc ggcttgatga tgatggaaac    2280
ttccagctca tgaatgatcc aggagcacct tggaagatat ggatgctcag aatggtctgt    2340
ctcgcgatta gtgcgtacac ccctgggca atcttgccct cagtagttgg atttggata     2400 actctccaat acacaaagag aggaggcgtg ttgtgggaca ctccctcacc aaaggagtac    2460
aaaaaggggg acacgaccac cggcgtctac aggatcatga ctcgtgggct gctcggcagt    2520
tatcaagcag gagcgggcgt gatggttgaa ggtgttttcc acacccttg gcatacaaca    2580
```

```
aaaggagccg ctttgatgag cggagagggc cgcctggacc catactgggg cagtgtcaag    2640
gaggatcgac tttgttacgg aggaccctgg aaattgcagc acaagtggaa cgggcaggat    2700
gaggtgcaga tgattgtggt ggaacctggc aagaacgtta agaacgtcca gacgaaacca    2760
ggggtgttca aaacacctga aggagaaatc ggggccgtga ctttggactt ccccactgga    2820
acatcaggct caccaatagt ggacaaaaac ggtgatgtga ttgggcttta tggcaatgga    2880
gtcataatgc ccaacggctc atacataagc gcgatagtgc agggtgaaag gatggatgag    2940
ccaatcccag ccggattcga acctgagatg ctgaggaaaa acagatcac tgtactggat     3000 ctccatcccg gcgccggtaa acaaggagg attctgccac agatcatcaa agaggccata     3060
aacagaagac tgagaacagc cgtgctagca ccaaccaggg ttgtggctgc tgagatggct    3120
gaagcactga gaggactgcc catccggtac cagacatccg cagtgcccag agaacataat    3180
ggaaatgaga ttgttgatgt catgtgtcat gctaccctca cccacaggct gatgtctcct    3240
cacagggtgc cgaactacaa cctgttcgtg atggatgagg ctcatttcac cgacccagct    3300
agcattgcag caagaggtta catttccaca aaggtcgagc taggggaggc ggcggcaata    3360
ttcatgacag ccaccccacc aggcacttca gatccattcc cagagtccaa ttcaccaatt    3420
tccgacttac agactgagat cccggatcga gcttggaact ctggatacga atggatcaca    3480
gaatacaccg ggaagacggt ttggtttgtg cctagtgtca agatggggaa tgagattgcc    3540
ctttgcctac aacgtgctgg aaagaaagta gtccaattga acagaaagtc gtacgagacg    3600
gagtacccaa aatgtaagaa cgatgattgg gactttgtta tcacaacaga catatctgaa    3660
atgggggcta actttaaggc gagcagggtg attgacagcc ggaagagtgt gaaaccaacc    3720
atcataacag aaggagaagg gagagtgatc ctgggagaac catctgcagt gacagcagct    3780
agtgccgccc agagacgtgg acgtatcggt agaaatccgt cgcaagttgg tgatgagtac    3840
tgttatgggg ggcacacgaa tgaagacgac tcgaacttcg cccattggac tgaggcacga    3900
atcatgctgg acaacatcaa catgccaaac ggactgatcg ctcaattcta ccaaccagag    3960
cgtgagaagg tataccat ggatggggaa taccggctca gaggagaaga gagaaaaaac      4020
tttctggaac tgttgaggac tgcagatctg ccagtttggc tggcttacaa ggttgcagcg    4080
gctggagtgt cataccacga ccggaggtgg tgctttgatg gtcctaggac aaacacaatt    4140
ttagaagaca caacgaagt ggaagtcatc acgaagcttg gtgaaaggaa gattctgagg     4200
ccgcgctgga ttgacgccag ggtgtactcg gatcaccagg cactaaaggc gttcaaggac    4260
ttcgcctcga gaaacgttc tcagataggg ctcattgagg ttctgggaaa gatgcctgag     4320
cacttcatgg ggaagacatg ggaagcactt gacaccatgt acgttgtggc cactgcagag    4380
aaaggaggaa gagctcacag aatggcctg gaggaactgc cagatgctct tcagacaatt    4440
gccttgattg ccttattgag tgtgatgacc atgggagtat tcttcctcct catgcagcgg    4500
aagggcattg gaaagatagg tttgggaggc gctgtcttgg gagtcgcgac cttttttctgt   4560 tggatggctg aagttccagg aacgaagatc gccggaatgt tgctgctctc ccttctcttg    4620
atgattgtgc taattcctga gccagagaag caacgttcgc agacagacaa ccagctagcc    4680
gtgttcctga tttgtgtcat gaccccttgtg agcgcagtgg cagccaacga gatgggttgg    4740
ctagataaga ccaagagtga cataagcagt ttgtttgggc aaagaattga ggtcaaggag    4800
aatttcagca tgggagagtt tcttctggac ttgaggccgg caacagcctg gtcactgtac    4860
gctgtgacaa cagcggtcct cactccactg ctaaagcatt tgatcacgtc agattacatc    4920
```

```
aacacctcat tgacctcaat aaacgttcag gcaagtgcac tattcacact cgcgcgaggc    4980 ttcccttcg tcgatgttgg agtgtcggct ctcctgctag cagccggatg ctggggacaa    5040
gtcaccctca ccgttacggt aacagcggca acactccttt tttgccacta tgcctacatg    5100
gttcccggtt ggcaagctga ggcaatgcgc tcagcccagc ggcggacagc ggccggaatc    5160
atgaagaacg ctgtagtgga tggcatcgtg gccacggacg tcccagaatt agagcgcacc    5220
acacccatca tgcagaagaa agttggacag atcatgctga tcttggtgtc tctagctgca    5280
gtagtagtga acccgtctgt gaagacagta cgagaagccg aattttgat cacggccgca    5340 gcggtgacgc tttgggagaa tggagcaagc tctgtttgga acgcaacaac tgccatcgga    5400
ctctgccaca tcatgcgtgg gggttggttg tcatgtctat ccataacatg gacactcata    5460
aagaacatgg aaaaccagg actaaaaaga ggtggggcaa aaggacgcac cttgggagag    5520
gtttggaaag aaagactcaa ccagatgaca aaagaagagt tcactaggta ccgcaaagag    5580
gccatcatcg aagtcgatcg ctcagcagca aaacacgcca ggaaagaagg caatgtcact    5640
ggagggcatc cagtctctag gggcacagca aaactgagat ggctggtcga acggaggttt    5700
ctcgaaccgg tcggaaaagt gattgacctt ggatgtggaa gaggcggttg gtgttactat    5760
atggcaaccc aaaaaagagt ccaagaagtc agagggtaca caaagggcgg tcccggacat    5820
gaagagcccc aactagtgca aagttatgga tggaacattg tcaccatgaa gagtggggtg    5880
gatgtgttct acagaccttc tgagtgttgt gacaccctcc tttgtgacat cggagagtcc    5940
tcgtcaagtg ctgaggttga agagcatagg acgattcggg tccttgaaat ggttgaggac    6000
tggctgcacc gagggccaag ggaattttgc gtgaaggtgc tctgcccta catgccgaaa    6060 gtcatagaga agatggagct gctccaacgc cggtatgggg gggactggt cagaaaccca    6120 ctctcacgga attccacgca cgagatgtat tgggtgagtc gagcttcagg caatgtggta    6180
cattcagtga atatgaccag ccaggtgctc ctaggaagaa tggaaaaaag gacctggaag    6240
ggaccccaat acgaggaaga tgtaaacttg ggaagtggaa ccagggcggt gggaaaaccc    6300
ctgctcaact cagacaccag taaaatcaag aacaggattg aacgactcag gcgtgagtac    6360
agttcgacgt ggcaccacga tgagaaccac ccatatagaa cctggaacta tcacggcagt    6420
tatgatgtga agcccacagg ctccgccagt tcgctggtca atggagtggt caggctcctc    6480
tcaaaaccat gggacaccat cacgaatgtt accaccatgg ccatgactga cactactccc    6540
ttcgggcagc agcgagtgtt caaagagaag gtggacacga aagctcctga accgccagaa    6600
ggagtgaagt acgtgctcaa cgagaccacc aactggttgt gggcgttttt ggccagagaa    6660
aaacgtccca gaatgtgctc tcgagaggaa ttcataagaa aggtcaacag caatgcagct    6720
ttgggtgcca tgtttgaaga gcagaatcaa tggaggagcg ccagagaggc agttgaagat    6780
ccaaaatttt gggagatggt ggatgaggag cgcgaggcac atctgcgggg ggaatgtcac    6840
acttgcattt acaacatgat gggaaagaga gagaaaaaac ccggagagtt cggaaaggcc    6900
aagggaagca gagccatttg gttcatgtgg ctcggagctc gctttctgga gttcgaggct    6960
ctgggttttc tcaatgaaga ccactggctt ggaagaaaga actcaggagg aggtgtcgag    7020
ggcttgggcc tccaaaaact gggttacatc ctgcgtgaag ttggcacccg gcctgggggc    7080
aagatctatg ctgatgacac agctggctgg gacacccgca tcacgagagc tgacttggaa    7140
aatgaagcta aggtgcttga gctgcttgat ggggaacatc ggcgtcttgc cagggccatc    7200
attgagctca cctatcgtca caaagttgtg aaagtgatgc gcccggctgc tgatggaaga    7260
accgtcatgg atgttatctc cagagaagat cagaggggga gtggacaagt tgtcacctac    7320
```

-continued

```
gccctaaaca ctttcaccaa cctggccgtc cagctggtga ggatgatgga aggggaagga    7380
gtgattggcc cagatgatgt ggagaaactc acaaaaggga aggacccaa agtcaggacc    7440 tggctgtttg agaatgggga agaaagactc agccgcatgg ctgtcagtgg agatgactgt    7500
gtggtaaagc ccctggacga tcgctttgcc acctcgctcc acttcctcaa tgctatgtca    7560
aaggttcgca agacatcca agagtggaaa ccgtcaactg gatggtatga ttggcagcag    7620
gttccatttt gctcaaacca tttcactgaa ttgatcatga agatggaag aacactggtg    7680 gttccatgcc gaggacagga tgaattggta ggcagagctc gcatatctcc aggggccgga    7740
tggaacgtcc gcgacactgc ttgtctggct aagtcttatg cccagatgtg gctgcttctg    7800
tacttccaca gaagagacct gcggctcatg gccaacgcca tttgctccgc tgtccctgtg    7860
aattgggtcc ctaccggaag aaccacgtgg tccatccatg caggaggaga gtggatgaca    7920
acagaggaca tgttggaggt ctggaaccgt gtttggatag aggagaatga atggatggaa    7980
gacaaaaccc cagtggagaa atggagtgac gtcccatatt caggaaaacg agaggacatc    8040
tggtgtggca gcctgattgg cacaagagcc cgagccacgt gggcagaaaa catccaggtg    8100
gctatcaacc aagtcagagc aatcatcgga gatgagaagt atgtggatta catgagttca    8160
ctaaagagat atgaagacac aactttggtt gaggacacag tactgtagat atttaatcaa    8220
ttgtaaatag acaatataag tatgcataaa agtgtagttt tatagtagta tttagtggtg    8280
ttagtgtaaa tagttaagaa aattttgagg agaaagtcag gccgggaagt tcccgccacc    8340
ggaagttgag tagacggtgc tgcctgcgac tcaaccccag gaggactggg tgaacaaagc    8400
cgcgaagtga tccatgtaag ccctcagaac cgtctcggaa ggaggacccc acatgttgta    8460
acttcaaagc ccaatgtcag accacgctac ggcgtgctac tctgcggaga gtgcagtctg    8520
cgatagtgcc ccaggaggac tgggttaaca aaggcaaacc aacgccccac gcggccctag    8580
ccccggtaat ggcgttaacc agggcgaaag gactagaggt tagaggagac cccgcggttt    8640
aaagtgcacg gcccagcctg gctgaagctg taggtcaggg gaaggactag aggttagtgg    8700 agacccgtg ccacaaaaca ccacaacaaa acagcatatt gacacctggg atagactagg    8760
agatcttctg ctctgcacaa ccagccacac ggcacagtgc ccgacaatg gtggctggtg    8820 gtgcgagaac acaggatct                                                8839
```

<210> SEQ ID NO 2
<211> LENGTH: 2703
<212> TYPE: PRT
<213> ORGANISM: West Nile virus

<400> SEQUENCE: 2

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Met
            20                  25                  30

Gly Ile Asn Ala Arg Asp Arg Ser Ile Ala Leu Thr Phe Leu Ala Val
        35                  40                  45

Gly Gly Val Leu Leu Phe Leu Ser Val Asn Val His Ala Asp Thr Gly
    50                  55                  60

Cys Ala Ile Asp Ile Ser Arg Gln Glu Leu Arg Cys Gly Ser Gly Val
65                  70                  75                  80

Phe Ile His Asn Asp Val Glu Ala Trp Met Asp Arg Tyr Lys Tyr Tyr
                85                  90                  95
```

-continued

```
Pro Glu Thr Pro Gln Gly Leu Ala Lys Ile Ile Gln Lys Ala His Lys
                100                 105                 110

Glu Gly Val Cys Gly Leu Arg Ser Val Ser Arg Leu Glu His Gln Met
            115                 120                 125

Trp Glu Ala Val Lys Asp Glu Leu Asn Thr Leu Leu Lys Glu Asn Gly
        130                 135                 140

Val Asp Leu Ser Val Val Glu Lys Gln Glu Gly Met Tyr Lys Ser
145                 150                 155                 160

Ala Pro Lys Arg Leu Thr Ala Thr Thr Glu Lys Leu Glu Ile Gly Trp
                165                 170                 175

Lys Ala Trp Gly Lys Ser Ile Leu Phe Ala Pro Glu Leu Ala Asn Asn
            180                 185                 190

Thr Phe Val Val Asp Gly Pro Glu Thr Lys Glu Cys Pro Thr Gln Asn
        195                 200                 205

Arg Ala Trp Asn Ser Leu Glu Val Glu Asp Phe Gly Phe Gly Leu Thr
210                 215                 220

Ser Thr Arg Met Phe Leu Lys Val Arg Glu Ser Asn Thr Thr Glu Cys
225                 230                 235                 240

Asp Ser Lys Ile Ile Gly Thr Ala Val Lys Asn Asn Leu Ala Ile His
                245                 250                 255

Ser Asp Leu Ser Tyr Trp Ile Glu Ser Arg Leu Asn Asp Thr Trp Lys
            260                 265                 270

Leu Glu Arg Ala Val Leu Gly Glu Val Lys Ser Cys Thr Trp Pro Glu
        275                 280                 285

Thr His Thr Leu Trp Gly Asp Gly Ile Leu Glu Ser Asp Leu Ile Ile
        290                 295                 300

Pro Val Thr Leu Ala Gly Pro Arg Ser Asn His Asn Arg Arg Pro Gly
305                 310                 315                 320

Tyr Lys Thr Gln Asn Gln Gly Pro Trp Asp Glu Gly Arg Val Glu Ile
                325                 330                 335

Asp Phe Asp Tyr Cys Pro Gly Thr Thr Val Thr Leu Ser Glu Ser Cys
            340                 345                 350

Gly His Arg Gly Pro Ala Thr Arg Thr Thr Glu Ser Gly Lys Leu
        355                 360                 365

Ile Thr Asp Trp Cys Cys Arg Ser Cys Thr Leu Pro Pro Leu Arg Tyr
370                 375                 380

Gln Thr Asp Ser Gly Cys Trp Tyr Gly Met Glu Ile Arg Pro Gln Arg
385                 390                 395                 400

His Asp Glu Lys Thr Leu Val Gln Ser Gln Val Asn Ala Tyr Asn Ala
                405                 410                 415

Asp Met Ile Asp Pro Phe Gln Leu Gly Leu Leu Val Val Phe Leu Ala
            420                 425                 430

Thr Gln Glu Val Leu Arg Lys Arg Trp Thr Ala Lys Ile Ser Met Pro
        435                 440                 445

Ala Ile Leu Ile Ala Leu Leu Val Leu Val Phe Gly Gly Ile Thr Tyr
450                 455                 460

Thr Asp Val Leu Arg Tyr Val Ile Leu Val Gly Ala Ala Phe Ala Glu
465                 470                 475                 480

Ser Asn Ser Gly Gly Asp Val Val His Leu Ala Leu Met Ala Thr Phe
                485                 490                 495

Lys Ile Gln Pro Val Phe Met Val Ala Ser Phe Leu Lys Ala Arg Trp
            500                 505                 510

Thr Asn Gln Glu Asn Ile Leu Leu Met Leu Ala Ala Val Phe Phe Gln
```

```
            515                 520                 525
Met Ala Tyr His Asp Ala Arg Gln Ile Leu Leu Trp Glu Ile Pro Asp
    530                 535                 540

Val Leu Asn Ser Leu Ala Val Ala Trp Met Ile Leu Arg Ala Ile Thr
545                 550                 555                 560

Phe Thr Thr Thr Ser Asn Val Val Pro Leu Leu Ala Leu Leu Thr
                    565                 570                 575

Pro Gly Leu Arg Cys Leu Asn Leu Asp Val Tyr Arg Ile Leu Leu Leu
                580                 585                 590

Met Val Gly Ile Gly Ser Leu Ile Arg Glu Lys Arg Ser Ala Ala Ala
                595                 600                 605

Lys Lys Lys Gly Ala Ser Leu Leu Cys Leu Ala Leu Ala Ser Thr Gly
    610                 615                 620

Leu Phe Asn Pro Met Ile Leu Ala Ala Gly Leu Ile Thr Cys Asp Pro
625                 630                 635                 640

Asn Arg Lys Arg Gly Trp Pro Ala Thr Glu Val Met Thr Ala Val Gly
                645                 650                 655

Leu Met Phe Ala Ile Val Gly Gly Leu Ala Glu Leu Asp Ile Asp Ser
                660                 665                 670

Met Ala Ile Pro Met Thr Ile Ala Gly Leu Met Phe Ala Ala Phe Val
    675                 680                 685

Ile Ser Gly Lys Ser Thr Asp Met Trp Ile Glu Arg Thr Ala Asp Ile
690                 695                 700

Ser Trp Glu Ser Asp Ala Glu Ile Thr Gly Ser Ser Glu Arg Val Asp
705                 710                 715                 720

Val Arg Leu Asp Asp Asp Gly Asn Phe Gln Leu Met Asn Asp Pro Gly
                725                 730                 735

Ala Pro Trp Lys Ile Trp Met Leu Arg Met Val Cys Leu Ala Ile Ser
                740                 745                 750

Ala Tyr Thr Pro Trp Ala Ile Leu Pro Ser Val Gly Phe Trp Ile
                755                 760                 765

Thr Leu Gln Tyr Thr Lys Arg Gly Gly Val Leu Trp Asp Thr Pro Ser
    770                 775                 780

Pro Lys Glu Tyr Lys Lys Gly Asp Thr Thr Thr Gly Val Tyr Arg Ile
785                 790                 795                 800

Met Thr Arg Gly Leu Leu Gly Ser Tyr Gln Ala Gly Ala Gly Val Met
                805                 810                 815

Val Glu Gly Val Phe His Thr Leu Trp His Thr Thr Lys Gly Ala Ala
                820                 825                 830

Leu Met Ser Gly Glu Gly Arg Leu Asp Pro Tyr Trp Gly Ser Val Lys
    835                 840                 845

Glu Asp Arg Leu Cys Tyr Gly Gly Pro Trp Lys Leu Gln His Lys Trp
    850                 855                 860

Asn Gly Gln Asp Glu Val Gln Met Ile Val Val Glu Pro Gly Lys Asn
865                 870                 875                 880

Val Lys Asn Val Gln Thr Lys Pro Gly Val Phe Lys Thr Pro Glu Gly
                885                 890                 895

Glu Ile Gly Ala Val Thr Leu Asp Phe Pro Thr Gly Thr Ser Gly Ser
                900                 905                 910

Pro Ile Val Asp Lys Asn Gly Asp Val Ile Gly Leu Tyr Gly Asn Gly
                915                 920                 925

Val Ile Met Pro Asn Gly Ser Tyr Ile Ser Ala Ile Val Gln Gly Glu
    930                 935                 940
```

```
Arg Met Asp Glu Pro Ile Pro Ala Gly Phe Glu Pro Glu Met Leu Arg
945                 950                 955                 960

Lys Lys Gln Ile Thr Val Leu Asp Leu His Pro Gly Ala Gly Lys Thr
            965                 970                 975

Arg Arg Ile Leu Pro Gln Ile Ile Lys Glu Ala Ile Asn Arg Arg Leu
        980                 985                 990

Arg Thr Ala Val Leu Ala Pro Thr Arg Val Val Ala Ala Glu Met Ala
    995                 1000                1005

Glu Ala Leu Arg Gly Leu Pro Ile Arg Tyr Gln Thr Ser Ala Val
    1010                1015                1020

Pro Arg Glu His Asn Gly Asn Glu Ile Val Asp Val Met Cys His
    1025                1030                1035

Ala Thr Leu Thr His Arg Leu Met Ser Pro His Arg Val Pro Asn
    1040                1045                1050

Tyr Asn Leu Phe Val Met Asp Glu Ala His Phe Thr Asp Pro Ala
    1055                1060                1065

Ser Ile Ala Ala Arg Gly Tyr Ile Ser Thr Lys Val Glu Leu Gly
    1070                1075                1080

Glu Ala Ala Ile Phe Met Thr Ala Thr Pro Pro Gly Thr Ser
    1085                1090                1095

Asp Pro Phe Pro Glu Ser Asn Ser Pro Ile Ser Asp Leu Gln Thr
    1100                1105                1110

Glu Ile Pro Asp Arg Ala Trp Asn Ser Gly Tyr Glu Trp Ile Thr
    1115                1120                1125

Glu Tyr Thr Gly Lys Thr Val Trp Phe Val Pro Ser Val Lys Met
    1130                1135                1140

Gly Asn Glu Ile Ala Leu Cys Leu Gln Arg Ala Gly Lys Lys Val
    1145                1150                1155

Val Gln Leu Asn Arg Lys Ser Tyr Glu Thr Glu Tyr Pro Lys Cys
    1160                1165                1170

Lys Asn Asp Asp Trp Asp Phe Val Ile Thr Thr Asp Ile Ser Glu
    1175                1180                1185

Met Gly Ala Asn Phe Lys Ala Ser Arg Val Ile Asp Ser Arg Lys
    1190                1195                1200

Ser Val Lys Pro Thr Ile Ile Thr Glu Gly Glu Gly Arg Val Ile
    1205                1210                1215

Leu Gly Glu Pro Ser Ala Val Thr Ala Ala Ser Ala Ala Gln Arg
    1220                1225                1230

Arg Gly Arg Ile Gly Arg Asn Pro Ser Gln Val Gly Asp Glu Tyr
    1235                1240                1245

Cys Tyr Gly Gly His Thr Asn Glu Asp Asp Ser Asn Phe Ala His
    1250                1255                1260

Trp Thr Glu Ala Arg Ile Met Leu Asp Asn Ile Asn Met Pro Asn
    1265                1270                1275

Gly Leu Ile Ala Gln Phe Tyr Gln Pro Glu Arg Glu Lys Val Tyr
    1280                1285                1290

Thr Met Asp Gly Glu Tyr Arg Leu Arg Gly Glu Glu Arg Lys Asn
    1295                1300                1305

Phe Leu Glu Leu Leu Arg Thr Ala Asp Leu Pro Val Trp Leu Ala
    1310                1315                1320

Tyr Lys Val Ala Ala Ala Gly Val Ser Tyr His Asp Arg Arg Trp
    1325                1330                1335
```

```
Cys Phe Asp Gly Pro Arg Thr Asn Thr Ile Leu Glu Asp Asn Asn
    1340            1345                1350

Glu Val Glu Val Ile Thr Lys Leu Gly Glu Arg Lys Ile Leu Arg
    1355            1360                1365

Pro Arg Trp Ile Asp Ala Arg Val Tyr Ser Asp His Gln Ala Leu
    1370            1375                1380

Lys Ala Phe Lys Asp Phe Ala Ser Gly Lys Arg Ser Gln Ile Gly
    1385            1390                1395

Leu Ile Glu Val Leu Gly Lys Met Pro Glu His Phe Met Gly Lys
    1400            1405                1410

Thr Trp Glu Ala Leu Asp Thr Met Tyr Val Val Ala Thr Ala Glu
    1415            1420                1425

Lys Gly Gly Arg Ala His Arg Met Ala Leu Glu Glu Leu Pro Asp
    1430            1435                1440

Ala Leu Gln Thr Ile Ala Leu Ile Ala Leu Leu Ser Val Met Thr
    1445            1450                1455

Met Gly Val Phe Phe Leu Leu Met Gln Arg Lys Gly Ile Gly Lys
    1460            1465                1470

Ile Gly Leu Gly Gly Ala Val Leu Gly Val Ala Thr Phe Phe Cys
    1475            1480                1485

Trp Met Ala Glu Val Pro Gly Thr Lys Ile Ala Gly Met Leu Leu
    1490            1495                1500

Leu Ser Leu Leu Leu Met Ile Val Leu Ile Pro Glu Pro Glu Lys
    1505            1510                1515

Gln Arg Ser Gln Thr Asp Asn Gln Leu Ala Val Phe Leu Ile Cys
    1520            1525                1530

Val Met Thr Leu Val Ser Ala Val Ala Ala Asn Glu Met Gly Trp
    1535            1540                1545

Leu Asp Lys Thr Lys Ser Asp Ile Ser Ser Leu Phe Gly Gln Arg
    1550            1555                1560

Ile Glu Val Lys Glu Asn Phe Ser Met Gly Glu Phe Leu Leu Asp
    1565            1570                1575

Leu Arg Pro Ala Thr Ala Trp Ser Leu Tyr Ala Val Thr Thr Ala
    1580            1585                1590

Val Leu Thr Pro Leu Leu Lys His Leu Ile Thr Ser Asp Tyr Ile
    1595            1600                1605

Asn Thr Ser Leu Thr Ser Ile Asn Val Gln Ala Ser Ala Leu Phe
    1610            1615                1620

Thr Leu Ala Arg Gly Phe Pro Phe Val Asp Val Gly Val Ser Ala
    1625            1630                1635

Leu Leu Leu Ala Ala Gly Cys Trp Gly Gln Val Thr Leu Thr Val
    1640            1645                1650

Thr Val Thr Ala Ala Thr Leu Leu Phe Cys His Tyr Ala Tyr Met
    1655            1660                1665

Val Pro Gly Trp Gln Ala Glu Ala Met Arg Ser Ala Gln Arg Arg
    1670            1675                1680

Thr Ala Ala Gly Ile Met Lys Asn Ala Val Val Asp Gly Ile Val
    1685            1690                1695

Ala Thr Asp Val Pro Glu Leu Glu Arg Thr Thr Pro Ile Met Gln
    1700            1705                1710

Lys Lys Val Gly Gln Ile Met Leu Ile Leu Val Ser Leu Ala Ala
    1715            1720                1725

Val Val Val Asn Pro Ser Val Lys Thr Val Arg Glu Ala Gly Ile
```

```
              1730                1735                1740
Leu Ile Thr Ala Ala Ala Val Thr Leu Trp Glu Asn Gly Ala Ser
         1745                1750                1755

Ser Val Trp Asn Ala Thr Thr Ala Ile Gly Leu Cys His Ile Met
         1760                1765                1770

Arg Gly Gly Trp Leu Ser Cys Leu Ser Ile Thr Trp Thr Leu Ile
         1775                1780                1785

Lys Asn Met Glu Lys Pro Gly Leu Lys Arg Gly Ala Lys Gly
         1790                1795                1800

Arg Thr Leu Gly Glu Val Trp Lys Glu Arg Leu Asn Gln Met Thr
         1805                1810                1815

Lys Glu Glu Phe Thr Arg Tyr Arg Lys Glu Ala Ile Ile Glu Val
         1820                1825                1830

Asp Arg Ser Ala Ala Lys His Ala Arg Lys Glu Gly Asn Val Thr
         1835                1840                1845

Gly Gly His Pro Val Ser Arg Gly Thr Ala Lys Leu Arg Trp Leu
         1850                1855                1860

Val Glu Arg Arg Phe Leu Glu Pro Val Gly Lys Val Ile Asp Leu
         1865                1870                1875

Gly Cys Gly Arg Gly Gly Trp Cys Tyr Tyr Met Ala Thr Gln Lys
         1880                1885                1890

Arg Val Gln Glu Val Arg Gly Tyr Thr Lys Gly Gly Pro Gly His
         1895                1900                1905

Glu Glu Pro Gln Leu Val Gln Ser Tyr Gly Trp Asn Ile Val Thr
         1910                1915                1920

Met Lys Ser Gly Val Asp Val Phe Tyr Arg Pro Ser Glu Cys Cys
         1925                1930                1935

Asp Thr Leu Leu Cys Asp Ile Gly Glu Ser Ser Ser Ser Ala Glu
         1940                1945                1950

Val Glu Glu His Arg Thr Ile Arg Val Leu Glu Met Val Glu Asp
         1955                1960                1965

Trp Leu His Arg Gly Pro Arg Glu Phe Cys Val Lys Val Leu Cys
         1970                1975                1980

Pro Tyr Met Pro Lys Val Ile Glu Lys Met Glu Leu Leu Gln Arg
         1985                1990                1995

Arg Tyr Gly Gly Gly Leu Val Arg Asn Pro Leu Ser Arg Asn Ser
         2000                2005                2010

Thr His Glu Met Tyr Trp Val Ser Arg Ala Ser Gly Asn Val Val
         2015                2020                2025

His Ser Val Asn Met Thr Ser Gln Val Leu Leu Gly Arg Met Glu
         2030                2035                2040

Lys Arg Thr Trp Lys Gly Pro Gln Tyr Glu Glu Asp Val Asn Leu
         2045                2050                2055

Gly Ser Gly Thr Arg Ala Val Gly Lys Pro Leu Leu Asn Ser Asp
         2060                2065                2070

Thr Ser Lys Ile Lys Asn Arg Ile Glu Arg Leu Arg Arg Glu Tyr
         2075                2080                2085

Ser Ser Thr Trp His His Asp Glu Asn His Pro Tyr Arg Thr Trp
         2090                2095                2100

Asn Tyr His Gly Ser Tyr Asp Val Lys Pro Thr Gly Ser Ala Ser
         2105                2110                2115

Ser Leu Val Asn Gly Val Val Arg Leu Leu Ser Lys Pro Trp Asp
         2120                2125                2130
```

```
Thr Ile Thr Asn Val Thr Thr Met Ala Met Thr Asp Thr Thr Pro
2135                2140                2145

Phe Gly Gln Gln Arg Val Phe Lys Glu Lys Val Asp Thr Lys Ala
2150                2155                2160

Pro Glu Pro Pro Glu Gly Val Lys Tyr Val Leu Asn Glu Thr Thr
2165                2170                2175

Asn Trp Leu Trp Ala Phe Leu Ala Arg Glu Lys Arg Pro Arg Met
2180                2185                2190

Cys Ser Arg Glu Glu Phe Ile Arg Lys Val Asn Ser Asn Ala Ala
2195                2200                2205

Leu Gly Ala Met Phe Glu Gln Asn Gln Trp Arg Ser Ala Arg
2210                2215                2220

Glu Ala Val Glu Asp Pro Lys Phe Trp Glu Met Val Asp Glu Glu
2225                2230                2235

Arg Glu Ala His Leu Arg Gly Glu Cys His Thr Cys Ile Tyr Asn
2240                2245                2250

Met Met Gly Lys Arg Glu Lys Lys Pro Gly Glu Phe Gly Lys Ala
2255                2260                2265

Lys Gly Ser Arg Ala Ile Trp Phe Met Trp Leu Gly Ala Arg Phe
2270                2275                2280

Leu Glu Phe Glu Ala Leu Gly Phe Leu Asn Glu Asp His Trp Leu
2285                2290                2295

Gly Arg Lys Asn Ser Gly Gly Gly Val Glu Gly Leu Gly Leu Gln
2300                2305                2310

Lys Leu Gly Tyr Ile Leu Arg Glu Val Gly Thr Arg Pro Gly Gly
2315                2320                2325

Lys Ile Tyr Ala Asp Asp Thr Ala Gly Trp Asp Thr Arg Ile Thr
2330                2335                2340

Arg Ala Asp Leu Glu Asn Glu Ala Lys Val Leu Glu Leu Leu Asp
2345                2350                2355

Gly Glu His Arg Arg Leu Ala Arg Ala Ile Ile Glu Leu Thr Tyr
2360                2365                2370

Arg His Lys Val Val Lys Val Met Arg Pro Ala Ala Asp Gly Arg
2375                2380                2385

Thr Val Met Asp Val Ile Ser Arg Glu Asp Gln Arg Gly Ser Gly
2390                2395                2400

Gln Val Val Thr Tyr Ala Leu Asn Thr Phe Thr Asn Leu Ala Val
2405                2410                2415

Gln Leu Val Arg Met Met Glu Gly Glu Gly Val Ile Gly Pro Asp
2420                2425                2430

Asp Val Glu Lys Leu Thr Lys Gly Lys Gly Pro Lys Val Arg Thr
2435                2440                2445

Trp Leu Phe Glu Asn Gly Glu Glu Arg Leu Ser Arg Met Ala Val
2450                2455                2460

Ser Gly Asp Asp Cys Val Val Lys Pro Leu Asp Asp Arg Phe Ala
2465                2470                2475

Thr Ser Leu His Phe Leu Asn Ala Met Ser Lys Val Arg Lys Asp
2480                2485                2490

Ile Gln Glu Trp Lys Pro Ser Thr Gly Trp Tyr Asp Trp Gln Gln
2495                2500                2505

Val Pro Phe Cys Ser Asn His Phe Thr Glu Leu Ile Met Lys Asp
2510                2515                2520
```

| | | | | | | | | | | |
|---|---|---|---|---|---|---|---|---|---|---|
| Gly | Arg | Thr | Leu | Val | Val | Pro | Cys | Arg | Gly | Gln | Asp | Glu | Leu | Val |
| | 2525 | | | | 2530 | | | | 2535 | | | | | |
| Gly | Arg | Ala | Arg | Ile | Ser | Pro | Gly | Ala | Gly | Trp | Asn | Val | Arg | Asp |
| | 2540 | | | | 2545 | | | | 2550 | | | | | |
| Thr | Ala | Cys | Leu | Ala | Lys | Ser | Tyr | Ala | Gln | Met | Trp | Leu | Leu | Leu |
| | 2555 | | | | 2560 | | | | 2565 | | | | | |
| Tyr | Phe | His | Arg | Arg | Asp | Leu | Arg | Leu | Met | Ala | Asn | Ala | Ile | Cys |
| | 2570 | | | | 2575 | | | | 2580 | | | | | |
| Ser | Ala | Val | Pro | Val | Asn | Trp | Val | Pro | Thr | Gly | Arg | Thr | Thr | Trp |
| | 2585 | | | | 2590 | | | | 2595 | | | | | |
| Ser | Ile | His | Ala | Gly | Gly | Glu | Trp | Met | Thr | Thr | Glu | Asp | Met | Leu |
| | 2600 | | | | 2605 | | | | 2610 | | | | | |
| Glu | Val | Trp | Asn | Arg | Val | Trp | Ile | Glu | Glu | Asn | Glu | Trp | Met | Glu |
| | 2615 | | | | 2620 | | | | 2625 | | | | | |
| Asp | Lys | Thr | Pro | Val | Glu | Lys | Trp | Ser | Asp | Val | Pro | Tyr | Ser | Gly |
| | 2630 | | | | 2635 | | | | 2640 | | | | | |
| Lys | Arg | Glu | Asp | Ile | Trp | Cys | Gly | Ser | Leu | Ile | Gly | Thr | Arg | Ala |
| | 2645 | | | | 2650 | | | | 2655 | | | | | |
| Arg | Ala | Thr | Trp | Ala | Glu | Asn | Ile | Gln | Val | Ala | Ile | Asn | Gln | Val |
| | 2660 | | | | 2665 | | | | 2670 | | | | | |
| Arg | Ala | Ile | Ile | Gly | Asp | Glu | Lys | Tyr | Val | Asp | Tyr | Met | Ser | Ser |
| | 2675 | | | | 2680 | | | | 2685 | | | | | |
| Leu | Lys | Arg | Tyr | Glu | Asp | Thr | Thr | Leu | Val | Glu | Asp | Thr | Val | Leu |
| | 2690 | | | | 2695 | | | | 2700 | | | | | |

```
<210> SEQ ID NO 3
<211> LENGTH: 8681
<212> TYPE: DNA
<213> ORGANISM: Yellow fever virus

<400> SEQUENCE: 3
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aactcgcgaa acatgacaat gtccatgagc atgatcttgg taggagtgat     240
catgatgttt ttgtctctag gagttggggc ggatcaagga tgcgccatca actttggcaa     300
gagagagctc aagtgcggag atggtatctt catatttaga gactctgatg actggctgaa     360
caagtactca tactatccag aagatcctgt gaagcttgca tcaatagtga aagcctcttt     420
tgaagaaggg aagtgtggcc taaattcagt tgactcccct gagcatgaga gtggagaag     480
cagggcagat gagatcaatg ccatttttga ggaaaacgag gtggacattt ctgttgtcgt     540
gcaggatcca aagaatgttt accagagagg aactcatcca ttttccagaa ttcgggatgg     600
tctgcagtat ggttggaaga cttggggtaa gaaccttgtg ttctcccag ggaggaagaa     660
tggaagcttc atcatagatg gaaagtccag gaaagaatgc ccgttttcaa accgggtctg     720
gaattctttc agatagagg agtttgggac gggagtgttc accacacgcg tgtacatgga     780
cgcagtcttt gaatacacca tagactgcga tggatctatc ttgggtgcag cggtgaacgg     840
aaaaaagagt gcccatggct ctccaacatt ttggatggga agtcatgaag taaatgggac     900
atggatgatc cacaccttgg aggcattaga ttacaaggag tgtgagtggc cactgacaca     960
tacgattgga acatcagttg aagagagtga atgttcatg ccgagatcaa tcggaggccc    1020
agttagctct cacaatcata tccctggata caaggttcag acgaacggac cttggatgca    1080
```

```
ggtaccacta gaagtgaaga gagaagcttg cccagggact agcgtgatca ttgatggcaa    1140
ctgtgatgga cggggaaaat caaccagatc caccacggat agcggaaaag ttattcctga    1200
atggtgttgc cgctcctgca caatgccgcc tgtgagcttc catggtagtg atgggtgttg    1260
gtatcccatg gaaattaggc caaggaaaac gcatgaaagc catctggtgc gctcctgggt    1320
tacagctgga gaaatacatg ctgtcccttt tggtttggtg agcatgatga tagcaatgga    1380
agtggtccta aggaaaagac agggaccaaa gcaaatgttg gttggaggag tagtgctctt    1440
gggagcaatg ctggtcgggc aagtaactct ccttgatttg ctgaaactca cagtggctgt    1500
gggattgcat ttccatgaga tgaacaatgg aggagacgcc atgtatatgg cgttgattgc    1560
tgccttttca atcagaccag ggctgctcat cggctttggg ctcaggaccc tatggagccc    1620
tcgggaacgc cttgtgctga ccctaggagc agccatggtg gagattgcct ggggtggcgt    1680
gatgggcggc ctgtggaagt atctaaatgc agtttctctc tgcatcctga caataaatgc    1740
tgttgcttct aggaaagcat caaataccat cttgcccctc atggctctgt tgacacctgt    1800
cactatggct gaggtgagac ttgccgcaat gttcttttgt gccgtggtta tcataggggt    1860
ccttcaccag aatttcaagg acacctccat gcagaagact atacctctgg tggccctcac    1920
actcacatct tacctgggct tgacacaacc ttttttgggc ctgtgtgcat ttctggcaac    1980
ccgcatattt gggcgaagga gtatcccagt gaatgaggca ctcgcagcag ctggtctagt    2040
gggagtgctg gcaggactgg cttttcagga gatggagaac ttccttggtc cgattgcagt    2100
tggaggactc ctgatgatgc tggttagcgt ggctgggagg gtggatgggc tagagctcaa    2160
gaagcttggt gaagtttcat gggaagagga ggcggagatc agcgggagtt ccgcccgcta    2220
tgatgtggca ctcagtgaac aaggggagtt caagctgctt tctgaagaga agtgccatg    2280 ggaccaggtt gtgatgacct cgctggcctt ggttggggct gccctccatc catttgcact    2340
tctgctggtc cttgctgggt ggctgtttca tgtcagggga gctaggagaa gtggggatgt    2400
cttgtgggat attcccactc ctaagatcat cgaggaatgt gaacatctgg aggatgggat    2460
ttatggcata ttccagtcaa ccttcttggg ggcctcccag cgaggagtgg gagtggcaca    2520
gggaggggtg ttccacacaa tgtggcatgt cacaagagga gctttccttg tcaggaatgg    2580
caagaagttg attccatctt gggcttcagt aaaggaagac cttgtcgcct atggtggctc    2640
atggaagttg gaaggcagat gggatggaga ggaagaggtc cagttgatcg cggctgttcc    2700
aggaaagaac gtggtcaacg tccagacaaa accgagcttg ttcaaagtga ggaatgggg    2760 agaaatcggg gctgtcgctc ttgactatcc gagtggcact tcaggatctc ctattgttaa    2820
caggaacgga gaggtgattg gctgtacgg caatggcatc cttgtcggtg acaactcctt    2880
cgtgtccgcc atatcccaga ctgaggtgaa ggaagaagga aaggaggagc tccaagagat    2940
cccgacaatg ctaaagaaag gaatgacaac tgtccttgat tttcatcctg gagctgggaa    3000
gacaagacgt ttcctcccac agatcttggc cgagtgcgca cggagacgct tgcgcactct    3060
tgtgttggcc cccaccaggg ttgttctttc tgaaatgaag gaggcttttc acggcctgga    3120
cgtgaaattc cacacacagg cttttttccgc tcacggcagc gggagagaag tcattgatgc    3180
catgtgccat gccaccctaa cttacaggat gttggaacca actaggggtg ttaactggga    3240
agtgatcatt atggatgaag cccatttttt ggatccagct agcatagccg ctagaggttg    3300
ggcagcgcac agagctaggg caaatgaaag tgcaacaatc ttgatgacag ccacaccgcc    3360
tgggactagt gatgaatttc cacattcaaa tggtgaaata gaagatgttc aaacggacat    3420
```

```
acccagtgag ccctggaaca cagggcatga ctggatccta gctgacaaaa ggcccacggc    3480
atggttcctt ccatccatca gagctgcaaa tgtcatggct gcctctttgc gtaaggctgg    3540
aaagagtgtg gtggtcctga acaggaaaac ctttgagaga gaatacccca cgataaagca    3600
gaagaaacct gactttatat tggccactga catagctgaa atgggagcca acctttgcgt    3660
ggagcgagtg ctggattgca ggacggcttt taagcctgtg cttgtggatg aagggaggaa    3720
ggtggcaata aaagggccac ttcgtatctc cgcatcctct gctgctcaaa ggaggggcg    3780 cattgggaga atcccaaca gagatggaga ctcatactac tattctgagc ctacaagtga    3840
aaataatgcc caccacgtct gctggttgga ggcctcaatg ctcttggaca acatggaggt    3900
gaggggtgga atggtcgccc cactctatgg cgttgaagga actaaaacac cagtttcccc    3960
tggtgaaatg agactgaggg atgaccagag gaaagtcttc agagaactag tgaggaattg    4020
tgacctgccc gtttggcttt cgtggcaagt ggccaaggct ggtttgaaga cgaatgatcg    4080
taagtggtgt tttgaaggcc ctgaggaaca tgagatcttg aatgacacgc gtgaaacagt    4140
gaagtgcagg gctcctggag gagcaaagaa gcctctgcgc ccaaggtggt gtgatgaaag    4200
ggtgtcatct gaccagagtg cgctgtctga atttattaag tttgctgaag gtaggagggg    4260
agctgctgaa gtgctagttg tgctgagtga actccctgat ttcctggcta aaaaaggtgg    4320
agaggcaatg gataccatca gtgtgttct ccactctgag gaaggctcta gggcttaccg    4380
caatgcacta tcaatgatgc ctgaggcaat gacaatagtc atgctgttta tactggctgg    4440
actactgaca tcgggaatgg tcatcttttt catgtctccc aaaggcatca gtagaatgtc    4500
tatggcgatg gcacaatgg ccggctgtgg atatctcatg ttccttggag gcgtcaaacc    4560
cactcacatc tcctatatca tgctcatatt ctttgtcctg atggtggttg tgatccccga    4620
gccagggcaa caaaggtcca tccaagacaa ccaagtggca tacctcatta ttggcatcct    4680
gacgctggtt tcagcggtgg cagccaacga gctaggcatg ctggagaaaa ccaaagagga    4740 cctcttggg aagaagaact taattccatc tagtgcttca ccctggagtt ggccggatct    4800
tgacctgaag ccaggagctg cctggacagt gtacgttggc attgttacaa tgctctctcc    4860
aatgttgcac cactggatca aagtcgaata tggcaacctg tctctgtctg aatagcccca    4920
gtcagcctca gtccttctt tcatggacaa ggggatacca ttcatgaaga tgaatatctc    4980
ggtcataatg ctgctggtca gtggctggaa ttcaataaca gtgatgcctc tgctctgtgg    5040 cataggggtgc gccatgctcc actggtctct cattttacct ggaatcaaag cgcagcagtc    5100
aaagcttgca cagagaaggg tgttccatgg cgttgccaag aaccctgtgg ttgatgggaa    5160
tccaacagtt gacattgagg aagctcctga aatgcctgcc ctttatgaga gaaactggc    5220 tctatatctc cttcttgctc tcagcctagc ttctgttgcc atgtgcagaa cgcccttttc    5280
attggctgaa ggcattgtcc tagcatcagc tgccttaggg ccgctcatag agggaaacac    5340
cagccttctt tggaatggac ccatggctgt ctccatgaca ggagtcatga ggggaatca    5400 ctatgctttt gtgggagtca tgtacaatct atggaagatg aaaactggac gccgggggag    5460
cgcgaatgga aaaactttgg gtgaagtctg gaagagggaa ctgaatctgt ggacaagcg    5520 acagtttgag ttgtataaaa ggaccgacat tgtgaggtg gatcgtgata cggcacgcag    5580
gcatttggcc gaagggaagg tggacaccgg ggtggcggtc tccaggggga ccgcaaagtt    5640
aaggtggttc catgagcgtg gctatgtcaa gctggaaggt agggtgattg acctggggtg    5700
tggccgcgga ggctggtgtt actacgctgc tgcgcaaaag gaagtgagtg gggtcaaagg    5760
atttactctt ggaagagacg gccatgagaa acccatgaat gtgcaaagtc tgggatggaa    5820
```

```
catcatcacc ttcaaggaca aaactgatat ccaccgccta gaaccagtga aatgtgacac    5880 cctttgtgt gacattggag agtcatcatc gtcatcggtc acagagggg aaaggaccgt    5940 gagagttctt gatactgtag aaaatggct ggcttgtggg gttgacaact tctgtgtgaa    6000
ggtgttagct ccatacatgc cagatgttct cgagaaactg gaattgctcc aaaggaggtt    6060
tggcggaaca gtgatcagga accctctctc caggaattcc actcatgaaa tgtactacgt    6120
gtctggagcc cgcagcaatg tcacatttac tgtgaaccaa acatcccgcc tcctgatgag    6180
gagaatgagg cgtccaactg aaaagtgac cctggaggct gacgtcatcc tcccaattgg    6240
gacacgcagt gttgagacag acaagggacc cctggacaaa gaggccatag aagaaagggt    6300
tgagaggata aaatctgagt acatgacctc ttggttttat gacaatgaca cccctacag    6360 gacctggcac tactgtggct cctatgtcac aaaaacctca ggaagtgcgg cgagcatggt    6420
aaatggtgtt attaaaattc tgacatatcc atgggacagg atagaggagg tcacaagaat    6480
ggcaatgact gacacaaccc cttttggaca gcaaagagtg tttaaagaaa aagttgacac    6540
cagagcaaag gatccaccag cgggaactag gaagatcatg aaagttgtca caggtggct    6600 gttccgccac ctggccagag aaaagaaccc cagactgtgc acaaaggaag aatttattgc    6660
aaaagtccga agtcatgcag ccattggagc ttacctggaa gaacaagaac agtggaagac    6720
tgccaatgag gctgtccaag acccaaagtt ctgggaactg gtggatgaag aaaggaagct    6780
gcaccaacaa ggcaggtgtc ggacttgtgt gtacaacatg atggggaaaa gagagaagaa    6840
gctgtcagag tttgggaaag caaagggaag ccgtgccata tggtatatgt ggctgggagc    6900
gcggtatctt gagtttgagg ccctgggatt cctgaatgag gaccattggg cttccaggga    6960
aaactcagga ggaggagtgg aaggcattgg cttacaatac ctaggatatg tgatcagaga    7020
cctggctgca atggatggtg gtggattcta cgcggatgac accgctggat gggacacgcg    7080
catcacagag gcagaccttg atgatgaaca ggagatcttg aactacatga gcccacatca    7140 caaaaactg gcacaagcag tgatggaaat gacatacaag aacaaagtgg tgaaagtgtt    7200
gagaccagcc ccaggaggga aagcctacat ggatgtcata agtcgacgag accagagagg    7260
atccgggcag gtagtgactt atgctctgaa caccatcacc aacttgaaag tccaattgat    7320
cagaatggca gaagcagaga tggtgataca tcaccaacat gttcaagatt gtgatgaatc    7380
agttctgacc aggctggagg catggctcac tgagcacgga tgtaacagac tgaagagat    7440 ggcggtgagt ggagacgact gtgtggtccg gcccatcgat gacaggttcg gcctggccct    7500
gtcccatctc aacgccatgt ccaaggttag aaaggacata tctgaatggc agccatcaaa    7560
agggtggaat gattgggaga atgtgccctt ctgttcccac cacttccatg aactacagct    7620
gaaggatggc aggaggattg tggtgccttg ccgagaacag gacgagctca ttgggagagg    7680
aagggtgtct ccaggaaacg gctggatgat caaggaaaca gcttgcctca gcaaagccta    7740
tgccaacatg tggtcactga tgtatttcca caaagggac atgaggctac tgtcattggc    7800
tgtttcctca gctgttccca cctcatgggt tccacaagga cgcacaacat ggtcgattca    7860
tgggaagggg agtggatga ccacggaaga catgcttgag gtgtggaaca gagtatggat    7920
aaccaacaac ccacacatgc aggacaagac aatggtgaaa aatgagagag atgtccctta    7980
tctaaccaag agacaagaca agctgtgcgg atcactgatt ggaatgacca ataggggccac    8040 ctgggcctcc cacatccatt tagtcatcca tcgtatccga acgctgattg acaggagaa    8100 atacactgac tacctaacag tcatggacag gtattctgtg gatgctgacc tgcaactggg    8160
```

-continued

```
tgagcttatc tgaaacacca tctaacagga ataaccggga tacaaaccac gggtggagaa       8220
ccggactccc cacaacctga aaccgggata taaaccacgg ctggagaacc ggactccgca       8280
cttaaaatga aacagaaacc gggataaaaa ctacggatgg agaaccggac tccacacatt       8340
gagacagaag aagttgtcag cccagaaccc cacacgagtt ttgccactgc taagctgtga       8400
ggcagtgcag gctgggacag ccgacctcca ggttgcgaaa aacctggttt ctgggacctc       8460 ccacccccaga gtaaaaagaa cggagcctcc gctaccaccc tcccacgtgg tggtagaaag       8520
acggggtcta gaggttagag aagaccctcc agggaacaaa tagtgggacc atattgacgc       8580
cagggaaaga ccggagtggt tctctgcttt tcctccagag gtctgtgagc acagtttgct       8640
caagaataag cagacctttg gatgacaaac acaaaaccac t                          8681
```

<210> SEQ ID NO 4
<211> LENGTH: 2684
<212> TYPE: PRT
<213> ORGANISM: Yellow fever virus

<400> SEQUENCE: 4

```
Met Ser Gly Arg Lys Ala Gln Gly Lys Thr Leu Gly Val Asn Met Val
1               5                   10                  15

Arg Arg Gly Val Arg Ser Leu Ser Asn Ser Arg Asn Met Thr Met Ser
            20                  25                  30

Met Ser Met Ile Leu Val Gly Val Ile Met Met Phe Leu Ser Leu Gly
        35                  40                  45

Val Gly Ala Asp Gln Gly Cys Ala Ile Asn Phe Gly Lys Arg Glu Leu
    50                  55                  60

Lys Cys Gly Asp Gly Ile Phe Ile Phe Arg Asp Ser Asp Asp Trp Leu
65                  70                  75                  80

Asn Lys Tyr Ser Tyr Tyr Pro Glu Asp Pro Val Lys Leu Ala Ser Ile
                85                  90                  95

Val Lys Ala Ser Phe Glu Glu Gly Lys Cys Gly Leu Asn Ser Val Asp
            100                 105                 110

Ser Leu Glu His Glu Met Trp Arg Ser Arg Ala Asp Glu Ile Asn Ala
        115                 120                 125

Ile Phe Glu Glu Asn Glu Val Asp Ile Ser Val Val Val Gln Asp Pro
    130                 135                 140

Lys Asn Val Tyr Gln Arg Gly Thr His Pro Phe Ser Arg Ile Arg Asp
145                 150                 155                 160

Gly Leu Gln Tyr Gly Trp Lys Thr Trp Gly Lys Asn Leu Val Phe Ser
                165                 170                 175

Pro Gly Arg Lys Asn Gly Ser Phe Ile Ile Asp Gly Lys Ser Arg Lys
            180                 185                 190

Glu Cys Pro Phe Ser Asn Arg Val Trp Asn Ser Phe Gln Ile Glu Glu
        195                 200                 205

Phe Gly Thr Gly Val Phe Thr Thr Arg Val Tyr Met Asp Ala Val Phe
    210                 215                 220

Glu Tyr Thr Ile Asp Cys Asp Gly Ser Ile Leu Gly Ala Ala Val Asn
225                 230                 235                 240

Gly Lys Lys Ser Ala His Gly Ser Pro Thr Phe Trp Met Gly Ser His
                245                 250                 255

Glu Val Asn Gly Thr Trp Met Ile His Thr Leu Glu Ala Leu Asp Tyr
            260                 265                 270

Lys Glu Cys Glu Trp Pro Leu Thr His Thr Ile Gly Thr Ser Val Glu
        275                 280                 285
```

```
Glu Ser Glu Met Phe Met Pro Arg Ser Ile Gly Pro Val Ser Ser
    290             295                 300

His Asn His Ile Pro Gly Tyr Lys Val Gln Thr Asn Gly Pro Trp Met
305             310                 315                 320

Gln Val Pro Leu Glu Val Lys Arg Glu Ala Cys Pro Gly Thr Ser Val
                325                 330                 335

Ile Ile Asp Gly Asn Cys Asp Gly Arg Gly Lys Ser Thr Arg Ser Thr
                340                 345                 350

Thr Asp Ser Gly Lys Val Ile Pro Glu Trp Cys Cys Arg Ser Cys Thr
            355                 360                 365

Met Pro Pro Val Ser Phe His Gly Ser Asp Gly Cys Trp Tyr Pro Met
    370                 375                 380

Glu Ile Arg Pro Arg Lys Thr His Glu Ser His Leu Val Arg Ser Trp
385                 390                 395                 400

Val Thr Ala Gly Glu Ile His Ala Val Pro Phe Gly Leu Val Ser Met
                405                 410                 415

Met Ile Ala Met Glu Val Val Leu Arg Lys Arg Gln Gly Pro Lys Gln
                420                 425                 430

Met Leu Val Gly Val Val Leu Leu Gly Ala Met Leu Val Gly Gln
                435                 440                 445

Val Thr Leu Leu Asp Leu Leu Lys Leu Thr Val Ala Val Gly Leu His
            450                 455                 460

Phe His Glu Met Asn Asn Gly Gly Asp Ala Met Tyr Met Ala Leu Ile
465                 470                 475                 480

Ala Ala Phe Ser Ile Arg Pro Gly Leu Leu Ile Gly Phe Gly Leu Arg
                485                 490                 495

Thr Leu Trp Ser Pro Arg Glu Arg Leu Val Leu Thr Leu Gly Ala Ala
                500                 505                 510

Met Val Glu Ile Ala Leu Gly Gly Val Met Gly Gly Leu Trp Lys Tyr
            515                 520                 525

Leu Asn Ala Val Ser Leu Cys Ile Leu Thr Ile Asn Ala Val Ala Ser
    530                 535                 540

Arg Lys Ala Ser Asn Thr Ile Leu Pro Leu Met Ala Leu Leu Thr Pro
545                 550                 555                 560

Val Thr Met Ala Glu Val Arg Leu Ala Ala Met Phe Phe Cys Ala Val
                565                 570                 575

Val Ile Ile Gly Val Leu His Gln Asn Phe Lys Asp Thr Ser Met Gln
                580                 585                 590

Lys Thr Ile Pro Leu Val Ala Leu Thr Leu Thr Ser Tyr Leu Gly Leu
            595                 600                 605

Thr Gln Pro Phe Leu Gly Leu Cys Ala Phe Leu Ala Thr Arg Ile Phe
    610                 615                 620

Gly Arg Arg Ser Ile Pro Val Asn Glu Ala Leu Ala Ala Gly Leu
625                 630                 635                 640

Val Gly Val Leu Ala Gly Leu Ala Phe Gln Glu Met Glu Asn Phe Leu
                645                 650                 655

Gly Pro Ile Ala Val Gly Gly Leu Leu Met Met Leu Val Ser Val Ala
                660                 665                 670

Gly Arg Val Asp Gly Leu Glu Leu Lys Lys Leu Gly Glu Val Ser Trp
            675                 680                 685

Glu Glu Glu Ala Glu Ile Ser Gly Ser Ser Ala Arg Tyr Asp Val Ala
690                 695                 700
```

-continued

Leu Ser Glu Gln Gly Glu Phe Lys Leu Leu Ser Glu Lys Val Pro
705                 710                 715                 720

Trp Asp Gln Val Val Met Thr Ser Leu Ala Leu Val Gly Ala Ala Leu
                725                 730                 735

His Pro Phe Ala Leu Leu Leu Val Leu Ala Gly Trp Leu Phe His Val
            740                 745                 750

Arg Gly Ala Arg Arg Ser Gly Asp Val Leu Trp Asp Ile Pro Thr Pro
        755                 760                 765

Lys Ile Ile Glu Glu Cys Glu His Leu Glu Asp Gly Ile Tyr Gly Ile
770                 775                 780

Phe Gln Ser Thr Phe Leu Gly Ala Ser Gln Arg Gly Val Gly Val Ala
785                 790                 795                 800

Gln Gly Gly Val Phe His Thr Met Trp His Val Thr Arg Gly Ala Phe
                805                 810                 815

Leu Val Arg Asn Gly Lys Lys Leu Ile Pro Ser Trp Ala Ser Val Lys
            820                 825                 830

Glu Asp Leu Val Ala Tyr Gly Gly Ser Trp Lys Leu Glu Gly Arg Trp
        835                 840                 845

Asp Gly Glu Glu Glu Val Gln Leu Ile Ala Ala Val Pro Gly Lys Asn
850                 855                 860

Val Val Asn Val Gln Thr Lys Pro Ser Leu Phe Lys Val Arg Asn Gly
865                 870                 875                 880

Gly Glu Ile Gly Ala Val Ala Leu Asp Tyr Pro Ser Gly Thr Ser Gly
                885                 890                 895

Ser Pro Ile Val Asn Arg Asn Gly Glu Val Ile Gly Leu Tyr Gly Asn
            900                 905                 910

Gly Ile Leu Val Gly Asp Asn Ser Phe Val Ser Ala Ile Ser Gln Thr
        915                 920                 925

Glu Val Lys Glu Glu Gly Lys Glu Glu Leu Gln Glu Ile Pro Thr Met
930                 935                 940

Leu Lys Lys Gly Met Thr Thr Val Leu Asp Phe His Pro Gly Ala Gly
945                 950                 955                 960

Lys Thr Arg Arg Phe Leu Pro Gln Ile Leu Ala Glu Cys Ala Arg Arg
                965                 970                 975

Arg Leu Arg Thr Leu Val Leu Ala Pro Thr Arg Val Val Leu Ser Glu
            980                 985                 990

Met Lys Glu Ala Phe His Gly Leu Asp Val Lys Phe His Thr Gln Ala
        995                 1000                1005

Phe Ser Ala His Gly Ser Gly Arg Glu Val Ile Asp Ala Met Cys
    1010                1015                1020

His Ala Thr Leu Thr Tyr Arg Met Leu Glu Pro Thr Arg Val Val
    1025                1030                1035

Asn Trp Glu Val Ile Ile Met Asp Glu Ala His Phe Leu Asp Pro
    1040                1045                1050

Ala Ser Ile Ala Ala Arg Gly Trp Ala Ala His Arg Ala Arg Ala
    1055                1060                1065

Asn Glu Ser Ala Thr Ile Leu Met Thr Ala Thr Pro Pro Gly Thr
    1070                1075                1080

Ser Asp Glu Phe Pro His Ser Asn Gly Glu Ile Glu Asp Val Gln
    1085                1090                1095

Thr Asp Ile Pro Ser Glu Pro Trp Asn Thr Gly His Asp Trp Ile
    1100                1105                1110

Leu Ala Asp Lys Arg Pro Thr Ala Trp Phe Leu Pro Ser Ile Arg

```
            1115                1120                1125

Ala Ala Asn Val Met Ala Ala Ser Leu Arg Lys Ala Gly Lys Ser
            1130                1135                1140

Val Val Val Leu Asn Arg Lys Thr Phe Glu Arg Glu Tyr Pro Thr
            1145                1150                1155

Ile Lys Gln Lys Lys Pro Asp Phe Ile Leu Ala Thr Asp Ile Ala
            1160                1165                1170

Glu Met Gly Ala Asn Leu Cys Val Glu Arg Val Leu Asp Cys Arg
            1175                1180                1185

Thr Ala Phe Lys Pro Val Leu Val Asp Glu Gly Arg Lys Val Ala
            1190                1195                1200

Ile Lys Gly Pro Leu Arg Ile Ser Ala Ser Ser Ala Ala Gln Arg
            1205                1210                1215

Arg Gly Arg Ile Gly Arg Asn Pro Asn Arg Asp Gly Asp Ser Tyr
            1220                1225                1230

Tyr Tyr Ser Glu Pro Thr Ser Glu Asn Asn Ala His His Val Cys
            1235                1240                1245

Trp Leu Glu Ala Ser Met Leu Leu Asp Asn Met Glu Val Arg Gly
            1250                1255                1260

Gly Met Val Ala Pro Leu Tyr Gly Val Glu Gly Thr Lys Thr Pro
            1265                1270                1275

Val Ser Pro Gly Glu Met Arg Leu Arg Asp Asp Gln Arg Lys Val
            1280                1285                1290

Phe Arg Glu Leu Val Arg Asn Cys Asp Leu Pro Val Trp Leu Ser
            1295                1300                1305

Trp Gln Val Ala Lys Ala Gly Leu Lys Thr Asn Asp Arg Lys Trp
            1310                1315                1320

Cys Phe Glu Gly Pro Glu Glu His Glu Ile Leu Asn Asp Ser Gly
            1325                1330                1335

Glu Thr Val Lys Cys Arg Ala Pro Gly Gly Ala Lys Lys Pro Leu
            1340                1345                1350

Arg Pro Arg Trp Cys Asp Glu Arg Val Ser Ser Asp Gln Ser Ala
            1355                1360                1365

Leu Ser Glu Phe Ile Lys Phe Ala Glu Gly Arg Arg Gly Ala Ala
            1370                1375                1380

Glu Val Leu Val Val Leu Ser Glu Leu Pro Asp Phe Leu Ala Lys
            1385                1390                1395

Lys Gly Gly Glu Ala Met Asp Thr Ile Ser Val Phe Leu His Ser
            1400                1405                1410

Glu Glu Gly Ser Arg Ala Tyr Arg Asn Ala Leu Ser Met Met Pro
            1415                1420                1425

Glu Ala Met Thr Ile Val Met Leu Phe Ile Leu Ala Gly Leu Leu
            1430                1435                1440

Thr Ser Gly Met Val Ile Phe Phe Met Ser Pro Lys Gly Ile Ser
            1445                1450                1455

Arg Met Ser Met Ala Met Gly Thr Met Ala Gly Cys Gly Tyr Leu
            1460                1465                1470

Met Phe Leu Gly Gly Val Lys Pro Thr His Ile Ser Tyr Ile Met
            1475                1480                1485

Leu Ile Phe Phe Val Leu Met Val Val Ile Pro Glu Pro Gly
            1490                1495                1500

Gln Gln Arg Ser Ile Gln Asp Asn Gln Val Ala Tyr Leu Ile Ile
            1505                1510                1515
```

-continued

```
Gly Ile Leu Thr Leu Val Ser Ala Val Ala Asn Glu Leu Gly
        1520                1525                1530

Met Leu Glu Lys Thr Lys Glu Asp Leu Phe Gly Lys Lys Asn Leu
        1535                1540                1545

Ile Pro Ser Ser Ala Ser Pro Trp Ser Trp Pro Asp Leu Asp Leu
        1550                1555                1560

Lys Pro Gly Ala Ala Trp Thr Val Tyr Val Gly Ile Val Thr Met
        1565                1570                1575

Leu Ser Pro Met Leu His His Trp Ile Lys Val Glu Tyr Gly Asn
        1580                1585                1590

Leu Ser Leu Ser Gly Ile Ala Gln Ser Ala Ser Val Leu Ser Phe
        1595                1600                1605

Met Asp Lys Gly Ile Pro Phe Met Lys Met Asn Ile Ser Val Ile
        1610                1615                1620

Met Leu Leu Val Ser Gly Trp Asn Ser Ile Thr Val Met Pro Leu
        1625                1630                1635

Leu Cys Gly Ile Gly Cys Ala Met Leu His Trp Ser Leu Ile Leu
        1640                1645                1650

Pro Gly Ile Lys Ala Gln Gln Ser Lys Leu Ala Gln Arg Arg Val
        1655                1660                1665

Phe His Gly Val Ala Lys Asn Pro Val Val Asp Gly Asn Pro Thr
        1670                1675                1680

Val Asp Ile Glu Glu Ala Pro Glu Met Pro Ala Leu Tyr Glu Lys
        1685                1690                1695

Lys Leu Ala Leu Tyr Leu Leu Leu Ala Leu Ser Leu Ala Ser Val
        1700                1705                1710

Ala Met Cys Arg Thr Pro Phe Ser Leu Ala Glu Gly Ile Val Leu
        1715                1720                1725

Ala Ser Ala Ala Leu Gly Pro Leu Ile Glu Gly Asn Thr Ser Leu
        1730                1735                1740

Leu Trp Asn Gly Pro Met Ala Val Ser Met Thr Gly Val Met Arg
        1745                1750                1755

Gly Asn His Tyr Ala Phe Val Gly Val Met Tyr Asn Leu Trp Lys
        1760                1765                1770

Met Lys Thr Gly Arg Arg Gly Ser Ala Asn Gly Lys Thr Leu Gly
        1775                1780                1785

Glu Val Trp Lys Arg Glu Leu Asn Leu Leu Asp Lys Arg Gln Phe
        1790                1795                1800

Glu Leu Tyr Lys Arg Thr Asp Ile Val Glu Val Asp Arg Asp Thr
        1805                1810                1815

Ala Arg Arg His Leu Ala Glu Gly Lys Val Asp Thr Gly Val Ala
        1820                1825                1830

Val Ser Arg Gly Thr Ala Lys Leu Arg Trp Phe His Glu Arg Gly
        1835                1840                1845

Tyr Val Lys Leu Glu Gly Arg Val Ile Asp Leu Gly Cys Gly Arg
        1850                1855                1860

Gly Gly Trp Cys Tyr Tyr Ala Ala Ala Gln Lys Glu Val Ser Gly
        1865                1870                1875

Val Lys Gly Phe Thr Leu Gly Arg Asp Gly His Glu Lys Pro Met
        1880                1885                1890

Asn Val Gln Ser Leu Gly Trp Asn Ile Ile Thr Phe Lys Asp Lys
        1895                1900                1905
```

```
Thr Asp Ile His Arg Leu Glu Pro Val Lys Cys Asp Thr Leu Leu
1910                1915                1920

Cys Asp Ile Gly Glu Ser Ser Ser Ser Val Thr Glu Gly Glu
1925                1930                1935

Arg Thr Val Arg Val Leu Asp Thr Val Glu Lys Trp Leu Ala Cys
1940                1945                1950

Gly Val Asp Asn Phe Cys Val Lys Val Leu Ala Pro Tyr Met Pro
1955                1960                1965

Asp Val Leu Glu Lys Leu Glu Leu Leu Gln Arg Arg Phe Gly Gly
1970                1975                1980

Thr Val Ile Arg Asn Pro Leu Ser Arg Asn Ser Thr His Glu Met
1985                1990                1995

Tyr Tyr Val Ser Gly Ala Arg Ser Asn Val Thr Phe Thr Val Asn
2000                2005                2010

Gln Thr Ser Arg Leu Leu Met Arg Arg Met Arg Pro Thr Gly
2015                2020                2025

Lys Val Thr Leu Glu Ala Asp Val Ile Leu Pro Ile Gly Thr Arg
2030                2035                2040

Ser Val Glu Thr Asp Lys Gly Pro Leu Asp Lys Glu Ala Ile Glu
2045                2050                2055

Glu Arg Val Glu Arg Ile Lys Ser Glu Tyr Met Thr Ser Trp Phe
2060                2065                2070

Tyr Asp Asn Asp Asn Pro Tyr Arg Thr Trp His Tyr Cys Gly Ser
2075                2080                2085

Tyr Val Thr Lys Thr Ser Gly Ser Ala Ala Ser Met Val Asn Gly
2090                2095                2100

Val Ile Lys Ile Leu Thr Tyr Pro Trp Asp Arg Ile Glu Glu Val
2105                2110                2115

Thr Arg Met Ala Met Thr Asp Thr Thr Pro Phe Gly Gln Gln Arg
2120                2125                2130

Val Phe Lys Glu Lys Val Asp Thr Arg Ala Lys Asp Pro Pro Ala
2135                2140                2145

Gly Thr Arg Lys Ile Met Lys Val Val Asn Arg Trp Leu Phe Arg
2150                2155                2160

His Leu Ala Arg Glu Lys Asn Pro Arg Leu Cys Thr Lys Glu Glu
2165                2170                2175

Phe Ile Ala Lys Val Arg Ser His Ala Ala Ile Gly Ala Tyr Leu
2180                2185                2190

Glu Glu Gln Glu Gln Trp Lys Thr Ala Asn Glu Ala Val Gln Asp
2195                2200                2205

Pro Lys Phe Trp Glu Leu Val Asp Glu Glu Arg Lys Leu His Gln
2210                2215                2220

Gln Gly Arg Cys Arg Thr Cys Val Tyr Asn Met Met Gly Lys Arg
2225                2230                2235

Glu Lys Lys Leu Ser Glu Phe Gly Lys Ala Lys Gly Ser Arg Ala
2240                2245                2250

Ile Trp Tyr Met Trp Leu Gly Ala Arg Tyr Leu Glu Phe Glu Ala
2255                2260                2265

Leu Gly Phe Leu Asn Glu Asp His Trp Ala Ser Arg Glu Asn Ser
2270                2275                2280

Gly Gly Gly Val Glu Gly Ile Gly Leu Gln Tyr Leu Gly Tyr Val
2285                2290                2295

Ile Arg Asp Leu Ala Ala Met Asp Gly Gly Gly Phe Tyr Ala Asp
```

```
                2300                2305                2310
Asp Thr Ala Gly Trp Asp Thr Arg Ile Thr Glu Ala Asp Leu Asp
    2315                2320                2325
Asp Glu Gln Glu Ile Leu Asn Tyr Met Ser Pro His His Lys Lys
    2330                2335                2340
Leu Ala Gln Ala Val Met Glu Met Thr Tyr Lys Asn Lys Val Val
    2345                2350                2355
Lys Val Leu Arg Pro Ala Pro Gly Gly Lys Ala Tyr Met Asp Val
    2360                2365                2370
Ile Ser Arg Arg Asp Gln Arg Gly Ser Gly Gln Val Val Thr Tyr
    2375                2380                2385
Ala Leu Asn Thr Ile Thr Asn Leu Lys Val Gln Leu Ile Arg Met
    2390                2395                2400
Ala Glu Ala Glu Met Val Ile His His Gln His Val Gln Asp Cys
    2405                2410                2415
Asp Glu Ser Val Leu Thr Arg Leu Glu Ala Trp Leu Thr Glu His
    2420                2425                2430
Gly Cys Asn Arg Leu Lys Arg Met Ala Val Ser Gly Asp Asp Cys
    2435                2440                2445
Val Val Arg Pro Ile Asp Asp Arg Phe Gly Leu Ala Leu Ser His
    2450                2455                2460
Leu Asn Ala Met Ser Lys Val Arg Lys Asp Ile Ser Glu Trp Gln
    2465                2470                2475
Pro Ser Lys Gly Trp Asn Asp Trp Glu Asn Val Pro Phe Cys Ser
    2480                2485                2490
His His Phe His Glu Leu Gln Leu Lys Asp Gly Arg Arg Ile Val
    2495                2500                2505
Val Pro Cys Arg Glu Gln Asp Glu Leu Ile Gly Arg Gly Arg Val
    2510                2515                2520
Ser Pro Gly Asn Gly Trp Met Ile Lys Glu Thr Ala Cys Leu Ser
    2525                2530                2535
Lys Ala Tyr Ala Asn Met Trp Ser Leu Met Tyr Phe His Lys Arg
    2540                2545                2550
Asp Met Arg Leu Leu Ser Leu Ala Val Ser Ser Ala Val Pro Thr
    2555                2560                2565
Ser Trp Val Pro Gln Gly Arg Thr Thr Trp Ser Ile His Gly Lys
    2570                2575                2580
Gly Glu Trp Met Thr Thr Glu Asp Met Leu Glu Val Trp Asn Arg
    2585                2590                2595
Val Trp Ile Thr Asn Asn Pro His Met Gln Asp Lys Thr Met Val
    2600                2605                2610
Lys Lys Trp Arg Asp Val Pro Tyr Leu Thr Lys Arg Gln Asp Lys
    2615                2620                2625
Leu Cys Gly Ser Leu Ile Gly Met Thr Asn Arg Ala Thr Trp Ala
    2630                2635                2640
Ser His Ile His Leu Val Ile His Arg Ile Arg Thr Leu Ile Gly
    2645                2650                2655
Gln Glu Lys Tyr Thr Asp Tyr Leu Thr Val Met Asp Arg Tyr Ser
    2660                2665                2670
Val Asp Ala Asp Leu Gln Leu Gly Glu Leu Ile
    2675                2680

<210> SEQ ID NO 5
```

<211> LENGTH: 22
<212> TYPE: PRT
<213> ORGANISM: Unknown
<220> FEATURE:
<221> NAME/KEY: source
<223> OTHER INFORMATION: /note="Description of Unknown: 2A peptide
      sequence"

<400> SEQUENCE: 5

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 6
<211> LENGTH: 33
<212> TYPE: PRT
<213> ORGANISM: Unknown
<220> FEATURE:
<221> NAME/KEY: source
<223> OTHER INFORMATION: /note="Description of Unknown: 2A peptide
      sequence"

<400> SEQUENCE: 6

Phe Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 7
<211> LENGTH: 25
<212> TYPE: PRT
<213> ORGANISM: Unknown
<220> FEATURE:
<221> NAME/KEY: source
<223> OTHER INFORMATION: /note="Description of Unknown: 2A peptide
      sequence"

<400> SEQUENCE: 7

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 8
<211> LENGTH: 23
<212> TYPE: PRT
<213> ORGANISM: Unknown
<220> FEATURE:
<221> NAME/KEY: source
<223> OTHER INFORMATION: /note="Description of Unknown: 2A peptide
      sequence"

<400> SEQUENCE: 8

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 9
<211> LENGTH: 21
<212> TYPE: PRT
<213> ORGANISM: Unknown
<220> FEATURE:
<221> NAME/KEY: source
<223> OTHER INFORMATION: /note="Description of Unknown: 2A peptide
      sequence"

<400> SEQUENCE: 9

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 10
<211> LENGTH: 576
<212> TYPE: DNA
<213> ORGANISM: Encephalomyocarditis virus

<400> SEQUENCE: 10

| cccccccta acgttactgg ccgaagccgc ttggaataag gccggtgtgc gtttgtctat | 60 |
| atgttatttt ccaccatatt gccgtctttt ggcaatgtga gggcccggaa acctggccct | 120 |
| gtcttcttga cgagcattcc tagggtctt tcccctctcg ccaaaggaat gcaaggtctg | 180 |
| ttgaatgtcg tgaaggaagc agttcctctg gaagcttctt gaagacaaac aacgtctgta | 240 |
| gcgacccttt gcaggcagcg gaaccccca cctggcgaca ggtgcctctg cggccaaaag | 300 |
| ccacgtgtat aagatacacc tgcaaaggcg gcacaacccc agtgccacgt tgtgagttgg | 360 |
| atagttgtgg aaagagtcaa atggctctcc tcaagcgtat tcaacaaggg gctgaaggat | 420 |
| gcccagaagg tacccattg tatgggatct gatctgggc ctcggtgcac atgctttaca | 480 |
| tgtgtttagt cgaggttaaa aaacgtctag gccccccgaa ccacggggac gtggttttcc | 540 |
| tttgaaaaac acgatgataa tatggccaca accatg | 576 |

<210> SEQ ID NO 11
<211> LENGTH: 746
<212> TYPE: DNA
<213> ORGANISM: Encephalomyocarditis virus

<400> SEQUENCE: 11

| ttaaaacagc tgtgggttgt tcccacccac agggcccact gggcgctagc actctgattt | 60 |
| tacgaaatcc ttgtgcgcct gttttatatc ccttccctaa ttcgaaacgt agaagcaatg | 120 |
| cgcaccactg atcaatagta ggcgtaacgc gccagttacg tcatgatcaa gcatatctgt | 180 |
| tcccccggac tgagtatcaa tagactgctt acgcggttga aggagaaaac gttcgttatc | 240 |
| cggctaacta cttcgagaag cccagtaaca ccatggaagc tgcagggtgt ttcgctcagc | 300 |
| acttcccccg tgtagatcag gtcgatgagc cactgcaatc cccacaggtg actgtggcag | 360 |
| tggctgcgtt ggcggcctgc ctatggggag acccatagga cgctctaatg tggacatggt | 420 |
| gcgaagagcc tattgagcta gttagtagtc ctccggcccc tgaatgcggc taatcctaac | 480 |
| tgcggagcac atgccttcaa cccagagggt agtgtgtcgt aatgggcaac tctgcagcgg | 540 |
| aaccgactac tttgggtgtc cgtgtttctt tttattctta tattggctgc ttatggtgac | 600 |
| aattacagaa ttgttaccat atagctattg gattggccat ccggtgtgta atagagctgt | 660 |
| tatataccta tttgttggct ttgtaccact aactttaaaa tctataacta ccctcaactt | 720 |
| tatattaacc ctcaatacag ttgaac | 746 |

<210> SEQ ID NO 12
<211> LENGTH: 360
<212> TYPE: DNA
<213> ORGANISM: Hepatitis C virus

<400> SEQUENCE: 12

```
gccagccccc gattgggggc gacactccac catagatcac tccccctgtga ggaactactg    60
tcttcacgca gaaagcgtct agccatggcg ttagtatgag tgtcgtgcag cctccaggcc   120
ccccctccc gggagagcca tagtggtctg cggaaccggt gagtacaccg gaattgccag   180
gacgaccggg tcctttcttg gatcaatccc gctcaatgcc tggagatttg ggcgtgcccc   240
cgcgagactg ctagccgagt agtgttgggt cgcgaaaggc cttgtggtac tgcctgatag   300
ggtgcttgcg agtgccccgg gaggtctcgt agaccgtgca ccatgagcac gaatcctaaa   360
```

<210> SEQ ID NO 13
<211> LENGTH: 211
<212> TYPE: DNA
<213> ORGANISM: Cricket paralysis virus

<400> SEQUENCE: 13

```
ctaaaaagca aaatgtgat cttgcttgta aatacaattt tgagaggtta ataaattaca    60
agtagtgcta ttttttgtatt taggttagct atttagcttt acgttccagg atgcctagtg   120
gcagccccac aatatccagg aagccctctc tgcggttttt cagattaggt agtcgaaaaa   180
cctaagaaat ttacctgcta catttcaaga t                                   211
```

<210> SEQ ID NO 14
<211> LENGTH: 618
<212> TYPE: DNA
<213> ORGANISM: Human rhinovirus

<400> SEQUENCE: 14

```
ttaaaactgg gagtgggttg ttcccactca ctccacccat gcggtgttgt actctgttat    60
tacggtaact ttgtacgcca gttttttccca cccttcccca taatgtaact tagaagtttg   120
tacaatatga ccaataggtg acaatcatcc agactgtcaa aggtcaagca cttctgtttc   180
cccggtcaat gaggatatgc tttacccaag gcaaaaacct tagagatcgt tatccccaca   240
ctgcctacac agagcccagt accattttg atataattgg gttggtcgct ccctgcaaac   300
ccagcagtag acctggcaga tgaggctgga cattccccac tggcgacagt ggtccagcct   360
gcgtggctgc ctgctcaccc ttcttgggtg agaagcctaa ttattgacaa ggtgtgaaga   420
gccgcgtgtg ctcagtgtgc ttcctccggc ccctgaatgt ggctaacctt aaccctgcag   480
ccgttgccca taatccaatg ggtttgcggt cgtaatgcgt aagtgcggga tgggaccaac   540
tactttgggt gtccgtgttt cctgtttttc ttttgattgc attttatggt gacaatttat   600
agtgtataga ttgtcatc                                                 618
```

<210> SEQ ID NO 15
<211> LENGTH: 741
<212> TYPE: DNA
<213> ORGANISM: Coxsackievirus

<400> SEQUENCE: 15

```
ttaaaacagc ctgtggggttg ttcccaccca caggcccatt gggcgctagc actctggtat    60
cacggtacct ttgtgcgcct gttttacatc ccctcccaa attgtaattt agaagtttca   120
cacaccgatc attagcaagc gtggcacacc agccatgttt tgatcaagca cttctgttac   180
cccggactga gtatcaatag accgctaacg cggttgaagg agaaaacgtt cgttacccgg   240
ccaactactt cgaaaaacct agtaacacca tggaagttgc ggagtgtttc gctcagcact   300
accccagtgt agatcaggtc gatgagtcac cgcgttcccc acgggcgacc gtggcggtgg   360
```

```
ctgcgttggc ggcctgccta cggggaaacc cgtaggacgc tctaatacag acatggtgcg      420
aagagtctat tgagctagtt ggtaatcctc cggcccctga atgcggctaa tcctaactgc      480
ggagcacata ccctcaaacc aggggggcagt gtgtcgtaac gggcaactct gcagcggaac     540
cgactacttt gggtgtccgt gtttcatttt attcctatac tggctgctta tggtgacaat      600
tgacaggttg ttaccatata gttattggat tggccatccg gtgactaaca gagcaattat      660
atatctcttt gttgggttta taccacttag cttgaaagag gttaaaacac tacatctcat      720
cattaaacta aatacaacaa a                                                741

<210> SEQ ID NO 16
<211> LENGTH: 279
<212> TYPE: DNA
<213> ORGANISM: West Nile virus

<400> SEQUENCE: 16
agtagttcgc ctgtgtgagc tgacaaactt agtagtgttt gtgaggatta acaacaatta       60
acacagtgcg agctgtttct tagcacgaag atctcgatgt ctaagaaacc aggagggccc      120
ggcaagagcc gggctgtcaa tatgctaaaa cgcggaatgc cccgcgtgtt gtccttgatt      180
ggacttaaga tgggcatcaa tgctcgtgat aggtccatag ctctcacgtt tctcgcagtt      240
ggaggagttc tgctcttcct ctccgtgaac gtgcacgct                             279

<210> SEQ ID NO 17
<211> LENGTH: 271
<212> TYPE: DNA
<213> ORGANISM: Yellow fever virus

<400> SEQUENCE: 17
agtaaatcct gtgtgctaat tgaggtgcat tggtctgcaa atcgagttgc taggcaataa       60
acacatttgg attaattttta atcgttcgtt gagcgattag cagagaactg accagaaacat    120 gtctggtcgt aaagctcagg gaaaaaccct gggcgtcaat atggtacgac gaggagttcg     180
ctccttgtca aactcgcgaa acatgacaat gtccatgagc atgatcttgg taggagtgat     240
catgatgttt ttgtctctag gagttggggc g                                    271

<210> SEQ ID NO 18
<211> LENGTH: 90
<212> TYPE: DNA
<213> ORGANISM: West Nile virus

<400> SEQUENCE: 18
atgggcatca atgctcgtga taggtccata gctctcacgt ttctcgcagt tggaggagtt       60
ctgctcttcc tctccgtgaa cgtgcacgct                                       90

<210> SEQ ID NO 19
<211> LENGTH: 30
<212> TYPE: PRT
<213> ORGANISM: West Nile virus

<400> SEQUENCE: 19

Met Gly Ile Asn Ala Arg Asp Arg Ser Ile Ala Leu Thr Phe Leu Ala
1               5                   10                  15

Val Gly Gly Val Leu Leu Phe Leu Ser Val Asn Val His Ala
            20                  25                  30

<210> SEQ ID NO 20
```

```
<211> LENGTH: 74
<212> TYPE: DNA
<213> ORGANISM: Yellow fever virus

<400> SEQUENCE: 20
gaaacatgac aatgtccatg agcatgatct tggtaggagt gatcatgatg tttttgtctc      60
taggagttgg ggcg                                                       74

<210> SEQ ID NO 21
<211> LENGTH: 24
<212> TYPE: PRT
<213> ORGANISM: Yellow fever virus

<400> SEQUENCE: 21

Asn Met Thr Met Ser Met Ser Met Ile Leu Val Gly Val Ile Met Met
1               5                   10                  15

Phe Leu Ser Leu Gly Val Gly Ala
            20

<210> SEQ ID NO 22
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
taatacgact cactataga                                                  19

<210> SEQ ID NO 23
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
taatacgact cactattaa                                                  19

<210> SEQ ID NO 24
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
taatacgact cactataaa                                                  19

<210> SEQ ID NO 25
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
taatacgact cactatta                                                   18
```

```
<210> SEQ ID NO 26
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
taatacgact cactataa                                                 18

<210> SEQ ID NO 27
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
gatctctaga t                                                        11
```

FLAVIVIRUS REPLICONS

This application is a U.S. National Phase filing of International Application No. PCT/IB2016/051045 filed 25 Feb. 2016, which claims priority to EP Application No. 15157068.6 filed 27 Feb. 2015, the contents of which are incorporated herein by reference in their entirety.

FIELD OF THE INVENTION

This invention relates to, inter alia, improved replicons and replicon-encoding vectors for expression of heterologous proteins and related methods of using the same.

BACKGROUND OF THE INVENTION

Self-replicating ribonucleic acids (RNAs), e.g., derived from viral replicons, are useful for expression of proteins, such as heterologous proteins, for a variety of purposes, such as expression of therapeutic proteins and expression of antigens for vaccines. A desirable property of such replicons is the ability for sustained expression of the protein.

WO 99/28487 A1 (Queensland Dept. Health) and Varnayski et al., *Virology* 255, 366-375 (1999) disclose a nucleic acid sequence encoding a(+) strand self-replicating RNA, which includes a Kunjin Virus replicase-coding sequence, a protein-coding sequence coding for a portion of a flavivirus core protein and a flavivirus 5' untranslated region (UTR). The replicons could be packaged into viral replicon particles (VRPs) and used as vaccines.

Herd et al., "Recombinant Kunjin virus replicon vaccines induce protective T-cell immunity against human papillomavirus 16 E7-expressing tumour", *Virology* 319: 237-248 (2004) discloses a nucleic acid sequence encoding a(+) strand self-replicating RNA, which includes a Kunjin Virus replicase-coding sequence and a protein-coding sequence coding for a human papilloma virus (HPV) epitope to be used as vaccine.

Alcaraz-Estrada et al., "Construction of self-replicating subgenomic West Nile virus replicons for screening antiviral compounds", *Methods Mol. Biol.* 1030: 283-299 (2013) discloses a nucleic acid sequence encoding a(+) strand self-replicating RNA, which includes a West Nile Virus strain 956 replicase-coding sequence and a reporter gene.

WO 2006/086838 A1 (Queensland Inst. Med. Res.) discloses a (+) strand self-replicating RNA, which includes a Kunjin Virus replicase-coding sequence and a protein-coding sequence for a GM-CSF protein for use in tumor therapy. The '838 patent application also discloses the use of West Nile Virus and Yellow Fever Virus.

Queiroz et al., "Construction of yellow fever virus subgenomic replicons by yeast-based homologous recombination cloning technique", *Anais da Academia Brasileira de Ciências* 85: 159-168 (2010) discloses a nucleic acid sequence encoding a(+) strand self-replicating RNA, which includes a Yellow Fever Virus strain 170 replicase-coding sequence and a reporter gene.

Jones et al., "Construction and applications of yellow fever virus replicons", *Virology* 331: 247-259 (2005) discloses Yellow Fever Virus replicons encoding various reporter genes.

SUMMARY OF THE INVENTION

The invention provides, inter alia, improved replicons and vectors encoding them, where the replicons provide sustained expression of an encoded protein. These replicons comprise flavivirus replicases and heterologous protein coding sequences. The heterologous protein coding sequences are flanked by separation sequences for improved efficacy. These nucleic acids provided by the invention, including self-replicating RNAs provided by the invention, are useful in methods of protein expression, such as for vaccines (e.g., for methods of immunization), as well as expression of therapeutic proteins, such as antibodies (e.g., for methods of treatment).

BRIEF DESCRIPTION OF THE FIGURES

This invention is further illustrated by the following examples, which should not be construed as limiting. The examples refer to the following figures:

FIG. 1 is a schematic representation of replicons WNV001 and Y030. WNV001 contains an XbaI site for template linearization prior to in vitro transcription; unwanted nucleotides on the template strand are polished off with an exonuclease to generate a run-off template. Y030 contains a SapI site for linearization prior to in vitro transcription and yields a run-off template immediately after digestion. UTR=Untranslated Region, C*=Remaining sequence of capsid structural protein after engineered deletions to preserve cyclization sequence. E*=Remaining sequence of envelope structural protein after engineered deletions to preserve NS1 signal sequence. NS1-NS5=nonstructural WNV proteins.

FIG. 2A: Cells electroporated with A609 RNA reacting positively to immunohistochemistry (IHC). FIG. 2B: Cells electroporated with WNV001 RNA show few cells reacting positively to IHC. FIG. 2C: Mock electroporation yields no IHC positive cells.

FIG. 3 is a bar graph summarizing flow-cytometry analysis of Y030 RNA in BHK cells. Briefly, BHK cells were electroporated with 1 μg of RNA and analyzed for the presence of YFV antigen 24 hr post-electroporation. A mock electroporation was performed as a negative control.

FIGS. 4A-4B provide schematics of different WNV replicons and transcription schemes. FIG. 4A: Sense or antisense hepatitis delta virus ribozyme (S-HDVR or AS-HDVR) sequence were added immediately following the 3'UTR of WNV001 to generate second-generation replicons WNV006 and WNV007 containing the sense or anti-sense HDVR, respectively. FIG. 4B: The addition of ribozyme sequence eliminates the need for exonucleonuclease polishing on the template strand. FIG. 4B is adapted from Shi et al. *Virology* 296, 213-233 (2002).

FIG. 5 is a bar graph illustrating that the addition of HDVR significantly improves WNV replicon potency. Briefly, 0.25 μg-4 μg of WNV001, WNV006, or WNV007 RNA was electroporated into BHK cells. Cells were analyzed for the presence of WNV antigen via flow cytometry 48 hr post-electroporation. The results indicate that the sense HDVR, contained in WNV006, yields the most potent WNV replicon RNA at all ranges tested.

FIG. 8 provides modified T7 promoters driving transcription of flavivirus replicon RNA. FIG. 8A: Various promoter modifications added to WNV008 or Y042 replicon to generate replicon RNA initiated via ATP. The nucleotide at which transcription is initiated is in bold, and the first nucleotide of the authentic 5' UTR of flavivirus is underlined. OL=overlapping promoter–last nucleotide of promoter overlaps with first nucleotide of flavivirus 5' UTR sequence. *WNV008 is equivalent to WNV006 with a silent mutation present in the structural deleted region to generate an AflII cloning site. FIG. 8B: Yields of WNV RNA generated after in vitro transcription using modified promoters under the same in vitro transcription. The traditional T7 promoter f6.5 promoter driving transcription of WNV008 yields the most RNA. Modified promoters of driving transcription WNV017 and WNV026 have significantly decreased RNA yields. Modified promoters driving transcription of WNV027 and WNV028 reduce RNA yield by approximately 0.66-0.75 fold. RNA yields are normalized to RNA yield of WNV008. FIG. 8C: Example yields of YFV replicon RNA generated after in vitro transcription using modified promoters under the same in vitro transcription conditions.

FIG. 9 is a bar graph illustrating that modified T7 promoters driving transcription of WNV replicon RNA significantly enhance replicon potency. Briefly, 100 ng of WNV008, WNV017, WNV026, WNV027, or WNV028 was electroporated into BHK cells and analyzed for the presence of WNV antigen 24 h post electroporation. The data indicates that ATP-initiated T7 promoter f2.5 (OL) and T7 promoter f6.5 mut (OL) driving transcription of replicon RNA in WNV027 and WNV028, respectively, enhanced potency by approximately 15-fold over WNV RNA generated from a traditional T7 promoter f6.5 in WNV008.

FIG. 10 is a bar graph illustrating that modified T7 promoters driving transcription of YFV replicon RNA slightly enhance potency. Briefly, 100 ng of Y037, Y042, Y043, Y044, or Y045 RNA was electroporated into BHK cells and analyzed for the presence of YFV antigen 24 h post electroporation. The data indicates that ATP-initiated T7 promoter f2.5 and T7 promoter f6.5 mut driving transcription of replicon RNA in Y042 and Y043, respectively, enhanced potency by approximately 2-fold over YFV RNA generated from a traditional T7 promoter f6.5 in Y037.

FIG. 12 is a bar graph illustrating that optimized WNV and YFV replicons are potent. Briefly, 250 ng of each RNA was transfected into BHK or Hela cells and potency was observed via FACS analysis of GFP positive cells at 24, 48, or 72 hr post transfection. WNV has similar potency to TC83 replicon while YFV has lower potency.

FIG. 14 is a bar graph illustrating that WNV and YFV replicons are able to express GFP over 72 hr. Briefly, 250 ng of each RNA was transfected into BHK or Hela cells and expression was determined by mean fluorescent intensity at 24, 48, or 72 hr post transfection.

FIG. 15 is a bar graph illustrating that addition of HDVR significantly improves WNV replicon potency. Briefly, 0.25 μg-4 μg of WNV001 (RNA derived from XbaI/Mung Bean Template), WNV006 (RNA derived from sense-HDVR template), or WNV007 (RNA derived from antisense-HDVR template) RNA was electroporated into BHK cells. Cells were analyzed for the presence of WNV antigen via flow cytometry 48 hr post-electroporation.

FIG. 16 is a bar graph illustrating that RNA generated using ribozymes was still more potent than RNA generated using the run-off template. Template DNA of WNV006 was developed using PCR to generate a perfect run-off end without the need for Mung-bean nuclease treatment to trim non-native nucleotides from the template strand. RNA from the PCR generated template was evaluated against RNA that was generated with ribozyme assistance. Theoretically, all RNA transcripts should yield the same final product.

FIGS. 19A-19C summarize in vitro testing of WNV010, WNV011, and WNV012. FIG. 19A: Fluorescence microscopy images of cells transfected with reporter constructs. Briefly, 4 μg of each RNA was electroporated into BHK cells and observed for reporter function via GFP expression. Images were taken 72 hr post-electroporation. GFP expression was readily seen at ~48 hr in cells electroporated with RNA from WNV010 and WNV011, however, cells electroporated with RNA from WNV012 did not demonstrate observable GFP expression until 72 hr post-electroporation. FIG. 19B: Flow cytometry data. Briefly, BHK cells were electroporated with 4 µg of each RNA. Cells were harvested 72 hr post-electroporation and analyzed for the presence of WNV antigen or GFP expression via flow cytometry. The data demonstrates that WNV008 RNA alone yields a potency of ~19.5% as determined by the WNV antigen+ population. Potency drops to approximately 8% and 4% when cells were electroporated WNV010 and WNV011 RNA, respectively. Potency of the WNV012 was almost negligible. The flow cytometry data also indicates that GFP expression increases linearly with WNV antigen presence, which would be expected. FIG. 19C: Anti-FLAG western blot of BHK cell lysates. Briefly, BHK cells were electroporated with 4 µg of each construct and lysates were harvested and analyzed via an anti-FLAG antibody 48 hr post-electroporation; a VEE replicon expressing FLFPD.RSVF-'FLAG+FurinF2A+GFP'FLAG was used as a positive control (A611). A611 lysates clearly show an uncleaved FLFPD.RSVF'FLAG+FurinF2A+GFP'FLAG polypeptide as well as RSVF'FLAG and GFP'FLAG. Lysate from cells electroporated with WNV008 showed no signal as expected. In lysates of cells transfected with WNV010 and WNV011 RNA, a faint band of uncleaved reporter can be seen as well as GFP'FLAG+FurinGSGP2A peptide as expected since cytosolic GFP would not be cleaved by furin, however, cleaved RSFV'FLAG overlaps with background reactivity and cannot be clearly seen. No detectable anti-FLAG signal was observed in lysate of WNV012 presumably because of the very poor expression of the reporter from this construct.

FIGS. 21A-21B provide schematics of constructs and photograph of Western blot results. FIG. 21A is a schematic of addition of GFP'FLAG reporter into YFV replicon with no self-cleaving 2A sites (Y037 or Y040), with one C-terminal P2A site (Y038), or with N-terminal F2A and C-terminal P2A sites. FIG. 21B is a photograph of anti-FLAG western blot reveals full separation of GFP'FLAG reporter from viral polypeptide chain when GFP'FLAG is flanked by N-terminal P2A and C-terminal F2A (Y039).

FIGS. 23A-23B are bar graphs summarizing experimental results. FIG. 23A) In vitro potency assay of optimized WNV replicon with no reporters (WNV028) compared against GFP'FLAG or FLUC expressing derivatives (WNV029 and WNV030). Potency assay results indicate that potency is reduced by approximately 0.5× with the introduction of the reporter cassette. FIG. 23B) In vitro potency assay of GFP'FLAG expressing replicon (WNV029) compared to scFv-hFc expressing replicons (WNV038 and WNV039). Potency assay results indicate that scFv-hFc expressing replicons experience a further potency drop.

FIG. 24A: Anti-FLAG western blot of cell lysates from BHK cells electroporated with RNA from WNV028, WNV029, or a mock electroporation. FIG. 24A: ~32 kb band is visible in WNV029 lysate lane corresponding to the size of GFP'FLAG after 2A site processing FIG. 24B) Luciferase data from BHK cell lysates. Cells were electroporated with WNV028 (negative control; leftmost), WNV030 (luciferase expressing WNV, center) or A1007 (luciferase expressing TC83 positive control, rightmost) and harvested 24 hr or 48 hr post-electroporation. Data demonstrates WNV030 is capable of expressing luciferase. FIG. 24C: Anti-hFc western blot of cell supernatants from BHK cells electroporated with RNA from WNV038, WNV039, or A612 (scFv-hFc expressing control). Blot demonstrates that scFv-hFv is being expressed in cells electroporated with WNV038 or WNV039 and is of the appropriate size and is being secreted from the cell.

FIG. 25A: Potency assay of optimized, GFP expressing TC83, WNV, or YFV replicons (A750, WNV029, Y042 respectively) via GFP expression in BHK cells over time. BHK cells were transfected using cationic transfection reagents instead of electroporation for this particular assay. The data demonstrates that all replicons are capable of expressing GFP via flow-cytometry analysis. FIG. 25B: Potency assay of optimized, scFv-hFc expressing TC83, WNV, or YFV replicons (A612-A613, WNV038-WNV039, and Y046-Y047, respectively). BHK cells were electroporated with RNA and potency was determined by replicon specific antigen presence (dsRNA staining detected TC83 replicon presence, anti-WNV MHIAF detected WNV presence, anti-YFV MHIAF detected YFV presence. FIG. 25C: Anti-hFc western blot of cell supernatants from BHK cells electroporated with RNA from Y046, Y047, or A612 (scFv-hFc expressing control). Blot demonstrates that scFv-hFv is being expressed in cells electroporated with Y046 or Y047 and is of the appropriate size and is being secreted from the cell.

DETAILED DESCRIPTION OF THE INVENTION

Figure 2:
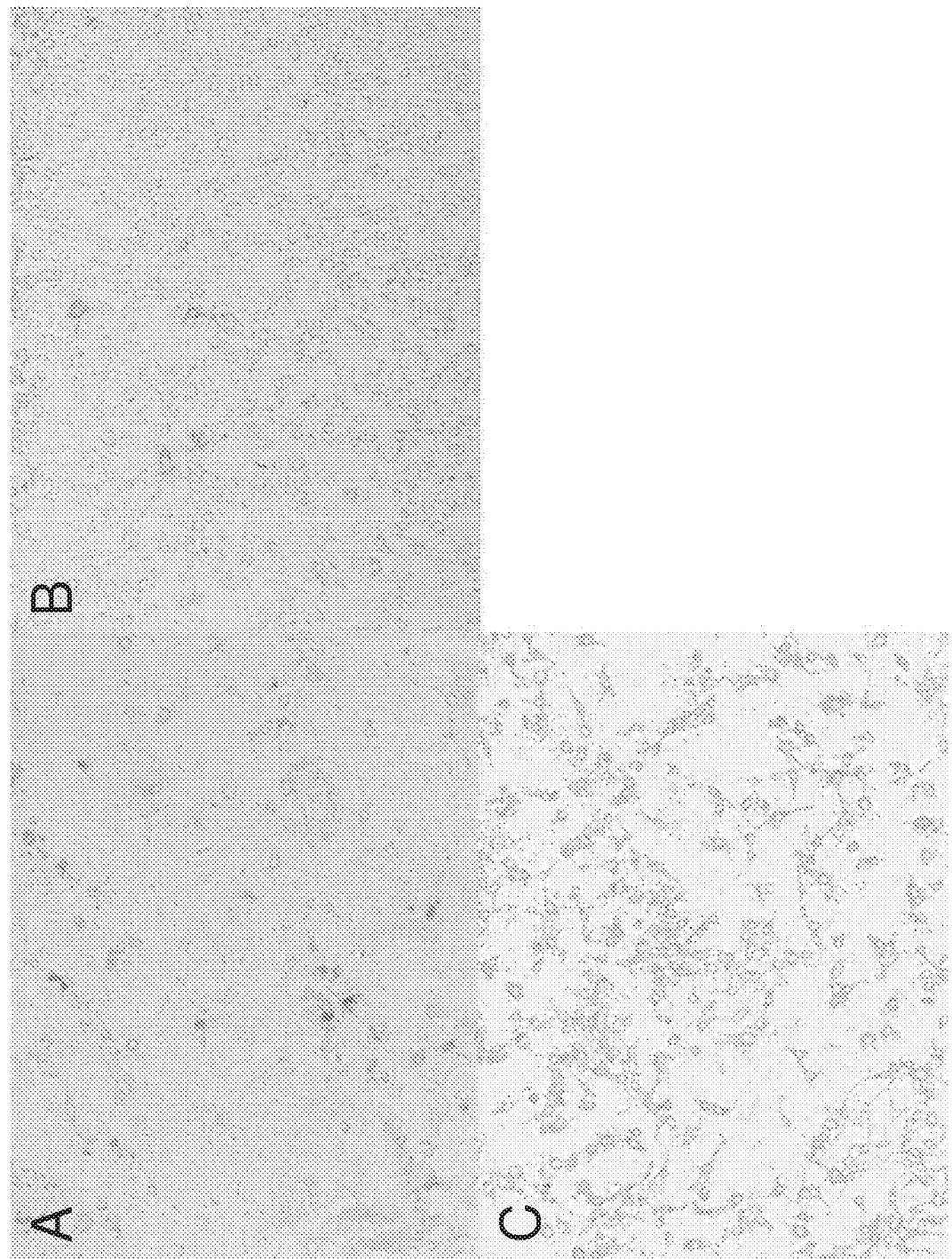
FIGS. 2A-2C provide micrographs from an immunohistochemical analysis of WNV001 RNA in BHK cells. Briefly, BHK cells were electroporated with 4 μg of RNA; cells were fixed, permeabilzied, and analyzed for the presence of WNV antigen 48 hr post-electroporation. RNA from alphavirus replicon expressing WNV-NS1 (A609) was used as a positive control.

In a first embodiment, the invention provides isolated nucleic acids comprising a sequence encoding a (+) strand self-replicating RNA, the self-replicating RNA comprising a flavivirus replicase-coding sequence and a heterologous protein-coding sequence, the heterologous protein coding sequence being disposed between at least two flanking separation sequences, the self-replicating RNA lacking coding sequence for viral structural proteins capable of forming viral particles.

A "flavivirus replicase" comprises the minimal machinery (e.g., protein and/or nucleotide factors) necessary for viral RNA replication in a suitable expression system, e.g., with transcriptional machinery, translational machinery, or transcriptional machinery and translational machinery. Exemplary expression systems include host cells, such as insect host cells or mammalian host cells. In some embodiments, the flavivirus replicase comprises NSPs (non-structural proteins; also called NSs) 3-5 (e.g., optionally including NS1, NS2 (including NS2A, NS2B, or both NS2A and NS2B), or NS1 and NS2) of one or more flaviviruses, including naturally occurring sequences, chimeric sequences, and synthetic derivatives.

In a second embodiment, the invention provides a nucleic acid according to the first embodiment, wherein the flavivirus replicase is a West Nile Virus (WNV) replicase.

In a third embodiment, the invention provides a nucleic acid according to the second embodiment, wherein the WNV is selected from WNV NY99, WN NY 2000-crow3356, HNY1999, NY99flamingo38299, IS98STD, goose-Hungary/03, Italy1998Equine, RO9750, VLG4, LEIV-VIg99-27889, PaH001, PaAn001, Eg101, Chin-01, Sarafend, B956 (WNFCG), goshawk-Hungary/04, LEIV-Krnd88-190, Nea Santa-Greece 2010, Goshawk-Hungary/04, Greece/2012/Kavala.39.1, Italy/2013/Rovigo/32.1, Austria/2008-gh, more particularly wherein the strain is selected from WNV NY99, WN NY 2000-crow3356, or HNY1999.

In a fourth embodiment, the invention provides a nucleic acid according to any of the previous embodiments, wherein the replicase comprises an amino acid sequence with at least 60% homology to SEQ ID NO: 2. In some other embodiments, the flavivirus replicase is at least about 60% (e.g., about: 50, 55, 60, 65, 70, 75, 80, 85, 90, 91, 92, 93, 94, 95, 96, 97, 98, 99, 99.9%, or more) homologous to a YFV or WNV sequence given by, for example SEQ ID NO:2 or SEQ ID NO:4, or portions thereof corresponding to NSs3-5, or more particularly, further including NS1, NS2 (including NS2A, NS2B, or both NS2A and NS2B), or NS1 and NS2 Additional sequences for flavivirus replicases are provided in NCBI reference accession no. ABU54838, which provides boundaries for the given NSP in the viral polyprotein. Corresponding sequences from other strains of WNV, YFV, or other flaviviruses (such as groups: Aroa, Dengue, Japanese encephalitis (which includes WNV), Kokobera, Ntaya, Spondweni, Yellow fever, Entebbe, Modic, and Rio Bravo) can be used in the invention and can be readily identified by annotations in publically-available sequences as well as by alignment to reference sequences provided herein (e.g., by BLAST). Additional strains are provided in Tables A and B. Further strains are described in Bakonyi et al. *Emerg. Infect. Dis.* 12(4):618-23 (April 2006); Hernandez-Triana et al. *Front. Public Health* 2:271. doi: 10.3389/fpubh.2014.00271; Wang, et al., *J. of General Virology* 78:1349-1352 (1997); Wang et al. *Virology* 225: 274-281 (1996), each of which is incorporated by reference for these descriptions.

In a fifth embodiment, the invention provides a nucleic acid according to the first embodiment, wherein the flavivirus replicase is a Yellow Fever Virus (YFV) replicase.

In a sixth embodiment, the invention provides a nucleic acid according to the fifth embodiment, wherein the YFV is 17D vaccine strain, Asibi strain, Uganda481, Angola71, 17D-204, 17DD, 17D-213, Uganda2010, 88/1999; more particularly where the strain is 17D vaccine strain or Asibi strain.

In a seventh embodiment, the invention provides a nucleic acid according to the fifth or sixth embodiment, wherein the replicase comprises an amino acid sequence with at least 60% homology to SEQ ID NO: 4. In some other embodiments, the replicase comprises an amino acid sequence with at least 60% homology (e.g., about 50, 55, 60, 65, 70, 75, 80, 85, 90, 91, 92, 93, 94, 95, 96, 97, 98, 99, 99.9%, or more) to SEQ ID NO: 4.

In an eighth embodiment, the invention provides a nucleic acid according to any one of the preceding embodiments, wherein the separation sequences are viral 2A sequences. Exemplary 2A sequences are provided in Table 1, infra, and can also readily be identified by the skilled artisan.

In a ninth embodiment, the invention provides a nucleic acid according to the eighth embodiment, wherein the two flanking separation sequences are selected from foot-and-mouth virus 2A, porcine teschovirus 2A, or a picornavirus 2A.

In a tenth embodiment, the invention provides a nucleic acid according to any one of the preceding embodiments, wherein the at least two flanking separation sequences do not recombine.

In an eleventh embodiment, the invention provides a nucleic acid according to any one of the preceding embodiments, wherein the self-replicating RNA retains a functional 5' UTR corresponding to a natural starting sequence of viral isolates. A functional 5' UTR comprises a minimal sequence necessary for the RNA to self-replicate in the presence of a suitable expression system. A natural starting sequence of a viral isolate corresponds to naturally occurring 5' UTRs, and in some embodiments comprises the first about 20, 25, 30, 35, 40, 45, 50, 55, 60, 65 or 70 nucleotides, or more, of 5' viral sequence.

In a twelfth embodiment, the invention provides a nucleic acid according to any one of the preceding embodiments, wherein the synthesis of the self-replicating RNA is driven by a promoter selected from T7, SPC6, CMV, or a functional fragment of any of the foregoing. In certain other embodiments, the self-replicating RNA is in operative association with (e.g., its expression is driven by) a promoter selected from T7, SPC6, CMV, or a functional fragment of any of the foregoing.

In a thirteenth embodiment, the invention provides a nucleic acid according to any one of the preceding embodiments, wherein the nucleic acid includes a sequence downstream of the self-replicating RNA for producing a functional 3' UTR.

In a fourteenth embodiment, the invention provides a nucleic acid according to the thirteenth embodiment, wherein the sequence for producing a functional 3' UTR encodes a ribozyme. Ribozymes are RNA-cleaving RNA sequences. Ribozymes useful in the invention cleave the self-replicating RNAs provided by the invention to retain function of the self-replicating RNA, e.g., by retaining functional 3' UTR sequences, i.e., sequence such cyclization sequences recognized by viral proteins and necessary for virus formation. In some particular embodiments, the invention provides a nucleic acid that encodes a ribozyme useful in producing naturally occurring 3' UTRs.

In a fifteenth embodiment, the invention provides a nucleic acid according to the fourteenth embodiment, wherein the ribozyme is a Hepatitis Delta Virus (HDV) ribozyme or a functional mutant thereof. A "functional mutant" of HDV ribozyme, or any other ribozyme useful in the invention, contains nucleotide substitutions, but retains functionality, e.g., by also mutating the nucleotide it base pairs with in the tertiary structure to preserve tertiary base pairings.

In a sixteenth embodiment, the invention provides a nucleic acid according to the thirteenth embodiment, wherein the downstream sequence is a restriction enzyme recognition sequence, such as, e.g., a BspQI site.

In a seventeenth embodiment, the invention provides a nucleic acid according to any one of the preceding embodiments, the nucleic acid comprises a sequence at least about: 60, 65, 60, 75, 80, 85, 90, 91, 92, 93, 94, 95, 96, 97, 98, 99 or 99.9% identical to SEQ ID NO: 1 or 3.

In an eighteenth embodiment, the invention provides a nucleic acid according to any one of the preceding embodiments, wherein the nucleic acid is a plasmid, optionally wherein the plasmid is a low-copy number plasmid. Exemplary low-copy number plasmids include p15A origin of replication-containing plasmids (e.g., pACYC (from NEB), pACNR (derived from pACYC177 from NEB, see Bredenbeek et al., *J. Gen. Virol.* 84: 1261-68 (2003))), BR322 origin of replication-containing plasmids (e.g., pBR322, from SIGMA), SC101 origin of replication-containing plasmids (e.g., pSC101 (from ATCC)), and the like.

In a related aspect, the invention also provides a host cell comprising a nucleic acid provided by the invention.

Thus, in a nineteenth embodiment, the invention provides a host cell comprising the nucleic acid according to any one of the preceding embodiments; optionally wherein the host is selected from XL10Gold® ultracompetent cells (Tet$^r$Δ

(mcrA)183 Δ(mcrCB-hsdSMR-mrr)173 endA1 supE44 thi-1 recA1 gyrA96 relA1 lac Hte [F' proAB lacI$^q$ZΔM15 Tn10 (Tet$^r$) Amy Cam$^r$] cells) and STELLAR cells (F-, endA1, supE44, thi-1, recA1, relA1, gyrA96, phoA, ϕ80d lacZΔ M15, Δ (lacZYA-argF) U169, Δ (mrr-hsdRMS-mcrBC), ΔmcrA, λ-cells).

In another related aspect the invention provides self-replicating RNAs, e.g., as encoded by any of the nucleic acids provided by the invention or as may be expressed (e.g., transcribed) from any nucleic acid provided by the invention. In a twentieth embodiment, the invention provides a self-replicating RNA encoded by the nucleic acid of any one of the preceding embodiments. In some other embodiments, the invention provides a self-replicating RNA comprising a sequence encoding a flavivirus replicase and a heterologous protein-coding sequence, the heterologous protein coding sequence being disposed between at least two flanking separation sequences, the self-replicating RNA lacking viral structural proteins capable of forming viral particles.

In a twenty-first embodiment, the invention provides a self-replicating RNA comprising a sequence encoding a flavivirus replicase and a heterologous protein-coding sequence, the heterologous protein coding sequence being disposed between at least two flanking separation sequences, the self-replicating RNA lacking viral structural proteins capable of forming viral particles.

In a twenty-second embodiment, the invention provides a nucleic acid according to any one of the preceding embodiments, wherein the heterologous protein coding sequence is an antigenic protein.

In a twenty-third embodiment, the invention provides a nucleic acid according to the twenty-second embodiment, wherein the antigenic protein, when administered to a mammalian subject, raises an immune response to a pathogen, optionally wherein the pathogen is bacterial, viral, fungal, protozoan, or cancerous, optionally more particularly wherein the antigenic protein is expressed on the outer surface of the pathogen.

In a twenty-fourth embodiment, the invention provides a nucleic acid according to any one of first to twenty-first embodiments, wherein the heterologous protein coding sequence is a therapeutic protein, optionally wherein the therapeutic protein is selected from a growth factor, cytokine, antibody, or antigen-binding fragment of an antibody.

In a twenty-fifth embodiment, the invention provides a nucleic acid according to any one of previous embodiments, wherein the nucleic acid is complexed with a delivery system, optionally wherein the delivery system is selected from a viral replicon particle (VRP), a lipid nanoparticle (LNP), a cationic nanoemulsion, or a biodegradeable polymer.

In a twenty-sixth embodiment, the invention provides a composition comprising the nucleic acid of any one of the preceding embodiments.

In a twenty-seventh embodiment, the invention provides a composition according to the twenty-sixth embodiment, wherein the nucleic acid is the nucleic acid the twenty, further comprising an adjuvant; optionally wherein the adjuvant is a metal salt.

In a twenty-eighth embodiment, the invention provides a composition according to the twenty-sixth or twenty-seventh embodiment, further comprising a TLR agonist; optionally wherein the TLR agonist is a TLR7 agonist; further optionally wherein the TLR7 agonist is a benzonapthyridine compound.

In a twenty-ninth embodiment, the invention provides a method of expressing a protein of interest, or a nucleic acid encoding the protein of interest, comprising contacting a nucleic acid of any one of the preceding claims with an expression system comprising transcriptional machinery, translational machinery, or transcriptional machinery and translational machinery, wherein the heterologous protein-coding sequence of the nucleic acid is the protein of interest.

In a thirtieth embodiment, the invention provides a method according to the twenty-ninth embodiment, wherein the expression system is a cell-free in vitro transcription system; optionally wherein the nucleic acid is a DNA sequence encoding the self-replicating RNA.

In a thirty-first embodiment, the invention provides a method according to the twenty-ninth embodiment, wherein the expression system comprises a translation system, optionally wherein the nucleic acid is the self-replicating RNA.

In a thirty-second embodiment, the invention provides a method according to any one of twenty-ninth to thirty-first embodiments, wherein the expression system is a eukaryotic cell.

In a thirty-third embodiment, the invention provides a method according to the thirty-second embodiment, wherein the eukaryotic cell is an insect cell.

In a thirty-fourth embodiment, the invention provides a method according to the thirty-second embodiment, wherein the eukaryotic cell is a mammalian cell.

In a thirty-fifth embodiment, the invention provides a method according to the thirty-fourth embodiment, wherein the mammalian cell is a CHO or COS cell.

In a thirty-sixth embodiment, the invention provides a method of raising an immune response to an antigenic protein in a mammalian subject, comprising administering the nucleic acid of the twenty-second embodiment to the subject.

In a thirty-seventh embodiment, the invention provides a method of administering a therapeutic protein to a mammalian subject, comprising administering the nucleic acid to the subject.

In a thirty-eighth embodiment, the invention provides a method according to the thirty-sixth or thirty-seventh embodiments, wherein the mammalian subject is a human.

TABLE A

West Nile Virus strains

| Strain | Accession no. |
|---|---|
| HNY 1999 | AF202541 |
| NY99flamingo38299 | AF196835 |
| IS98STD | AF481864 |
| goose-Hungary/03 | DQ118127 |
| Italy 1998Equine | AF404757 |
| RO9750 | AF260969 |
| VLG4 | AF317203 |
| LEIV-VIg99-27889 | AY277252 |
| PaH001 | AY268133 |
| PaAn001 | AY268132 |
| Eg101 | AF260968 |
| Chin-01 | AY490240 |
| Sarafend | AY688948 |
| B956 (WNFCG) | NC_001563 |
| goshawk-Hungary/04 | DQ116961 |
| LEIV-Krnd88-190 | AY277251 |
| Nea Santa-Greece 2010 | HQ537483 |
| Goshawk-Hungary/04 | DQ116961 |
| Greece/2012/Kavala.39.1 | KF179639 |
| Italy/2013/Rovigo/32.1 | KF588365 |
| Austria/2008-gh | KF179640 |

TABLE B

Flavivirus strains

| Strain | Accession no. |
|---|---|
| FVV | |
| Rendu | |
| Asibi | AY640589.1 |
| Dak1279 | |
| B4.1 | |
| 17DD | U17067.1 |
| 17D-213 | U17066.1 |
| JSS | |
| 69056 | |
| MR896 | |
| TR4205 | |
| Dak1279 | |
| ArB9005 | |
| ArB883 | |
| 1337 | |
| 788379 | |
| 149 | |
| 153 | |
| Uganda481 | AY968065.1 |
| Angola71 | AY968064.1 |
| 17D-204 | KF769015.1 |
| Uganda 2010 | JN620362.1 |
| 88/1999 | KF907504.1 |
| Asibi | AY640589.1 |

Programs useful for sequence alignments and comparisons include FASTA (Lipman and Pearson, *Science*, 227: 1435-41 (1985) and Lipman and Pearson, *Proc. Natl. Acad. Sci. U.S.A.* 85: 2444-48), BLAST (McGinnis & Madden, *Nucleic Acids Res.*, 32:W20-W25 (2004) (current BLAST reference, describing, inter alia, MegaBlast); Zhang et al., *J. Comput.* 7(1-2):203-14 (2000) (describing the "greedy algorithm" implemented in MegaBlast); Altschul et al., *J. Mol. Biol.*, 215:403-410 (1990) (original BLAST publication)), Needleman-Wunsch (Needleman and Wunsch, *J. Molec. Bio.*, 48 (3): 443-53(1970)), Sellers (Sellers, *Bull. Math. Biol.*, 46:501-14 (1984), and Smith-Waterman (Smith and Waterman, *J. Molec. Bio.*, 147: 195-197 (1981)), and other algorithms (including those described in Gerhard et *Genome Res.*, 14(10b):2121-27 (2004)), which are incorporated by reference.

"Transcriptional machinery" will produce RNA transcripts in the presence of a suitable DNA sequence, e.g., promoter sequences, polymerase-binding sites, et cetera. Transcriptional machinery can include whole cells, organisms, or in vitro systems.

"Translational machinery" will produce polypeptides in the presence of a suitable RNA sequence, e.g., ribosome binding sites, et cetera. Translational machinery can include whole cells, organisms, or in vitro systems.

A "separation sequence(s)": facilitates a single transcript forming two or more polypeptides. Exemplary separation sequences include viral 2A sequences, IRES (internal ribosomal entry sites), signal sequences, and protease recognition sites. Exemplary viral 2A sequences include (optionally with or without linker sequences, such as GSG linkers): P2A, F2A, E2A, T2A, described in Table 1, picornavirus or sequences described in Szymczak-Workman et al. *Cold Spring Harbor Protoc*, 2012(2): 199-204 (2012), which is incorporated by reference. Exemplary IRES sequences are given in Table 2.

A self-replicating RNA "lacking viral structural proteins capable of forming viral particles" cannot, in the absence of complementary helper sequences, form mature viral particles (e.g., as evaluated by various techniques, such as crystal structure or electron microscopy, e.g., may lack full capsid protein encoding sequences). As used herein, however, a self-replicating RNA "lacking viral structural proteins capable of forming viral particles" can retain elements required to replicate the RNA; e.g., cyclization and signal sequences. Exemplary cyclization and signal sequences are described in Tables 3 and 4, and are further described in Khromykh et al., *J. Virol.* 75: 6719-28 (2001) and Hahn et al., *J. Mol. Biol.* 198: 33-41 (1987), both of which are incorporated by reference. For example, for WNV the N-terminal coding region of protein C (nt. 97-189, referring to reference accession no. EF530047); the corresponding RNA sequence is an essential cis-acting element and may play a role in the regulation of minus-sense RNA synthesis. The C-terminal coding sequence of E protein (nt. 2380-2469 referring to reference accession no. EF530047) was preserved as this region acts as a signal sequence guiding the translocation and processing of non-structural protein 1 (NS1) and subsequently the remaining non-structural proteins NS2-NS5. These deletions render WNV non-infectious but replication competent. Similar deletions can be performed for other flavivirus replicons, such as a YFV replicon.

Heterologous Protein Coding Sequences

In a thirty-ninth embodiment, the invention provides a method of administration (e.g., to a host, such as a mammalian subject), whereby the self-replicating RNA is translated in vivo and the heterologous protein-coding sequence is expressed and, e.g., can elicit an immune response to the heterologous protein-coding sequence in the recipient or provide a therapeutic effect, where the heterologous protein-coding sequence is a therapeutic protein.

Immunogenic Proteins

In a fortieth embodiment, the invention provides a heterologous protein coding sequence of any of the preceding aspects and embodiments, wherein the heterologous protein coding sequence is an antigenic protein or immunogen, which terms will be used interchangeably.

In a forty-first embodiment, the antigenic protein of the fortieth embodiment, when administered to a mammalian subject, raises an immune response to a pathogen, optionally wherein the pathogen is bacterial, viral, fungal, protozoan, or cancerous. In some more particular embodiments, the antigenic protein is expressed on the outer surface of the pathogen; while in other more particular embodiments, the antigen may be a non-surface antigen, e.g., useful as a T-cell epitope. The immunogen may elicit an immune response against a pathogen (e.g. a bacterium, a virus, a fungus or a parasite) but, in some other embodiments, it elicits an immune response against an allergen or a tumor antigen. The immune response may comprise an antibody response (usually including IgG) and/or a cell mediated immune response. The polypeptide immunogen will typically elicit an immune response that recognises the corresponding pathogen (or allergen or tumor) polypeptide, but in some embodiments, the polypeptide may act as a mimotope to elicit an immune response that recognises a saccharide. The immunogen will typically be a surface polypeptide e.g. an adhesin, a hemagglutinin, an envelope glycoprotein, a spike glycoprotein, etc.

The RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

In a forty-second embodiment, polypeptide immunogens (e.g., 1, 2, 3, 4, 5, 6, 7, 8, 9, 10, or more immunogens) of the fortieth or forty-first embodiment may be used, either alone or together with a RNA molecule, such as a self-replicating RNA, encoding one or more immunogens (either the same or different as the polypeptide immunogens).

In a forty-third embodiment, the immunogen of the of the fortieth, forty-first or forty-second embodiment elicits an immune response against one of these bacteria:

*Neisseria meningitidis*: useful immunogens include, but are not limited to, membrane proteins such as adhesins, autotransporters, toxins, iron acquisition proteins, and factor H binding protein. A combination of three useful polypeptides is disclosed in Giuliani et al., *Proc. Natl. Acad. Sci. U.S.A.* 103(29):10834-9 (2006).

*Streptococcus pneumoniae*: useful polypeptide immunogens are disclosed in WO2009/016515. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.

*Streptococcus pyogenes*: useful immunogens include, but are not limited to, the polypeptides disclosed in WO02/34771 and WO2005/032582.

*Moraxella catarrhalis.*

*Bordetella pertussis*: Useful pertussis immunogens include, but are not limited to, pertussis toxin or toxoid (PT), filamentous haemagglutinin (FHA), pertactin, and agglutinogens 2 and 3.

*Staphylococcus aureus*: Useful immunogens include, but are not limited to, the polypeptides disclosed in WO2010/119343, such as a haemolysin, esxA, esxB, ferrichrome-binding protein (sta006) and/or the sta011 lipoprotein.

*Clostridium tetani*: the typical immunogen is tetanus toxoid.

*Cornynebacterium diphtheriae*: the typical immunogen is diphtheria toxoid.

*Haemophilus influenzae*: Useful immunogens include, but are not limited to, the polypeptides disclosed in WO2006/110413 and WO2005/111066.

*Pseudomonas aeruginosa*

*Streptococcus agalactiae*: useful immunogens include, but are not limited to, the polypeptides disclosed in WO02/34771.

*Chlamydia trachomatis*: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in WO2005/002619). LcrE (WO2006/138004) and HtrA (WO2009/109860) are two preferred immunogens.

*Chlamydia pneumoniae*: Useful immunogens include, but are not limited to, the polypeptides disclosed in WO02/02606.

*Helicobacter pylori*: Useful immunogens include, but are not limited to, CagA, VacA, NAP, and/or urease (WO03/018054).

*Escherichia coli*: Useful immunogens include, but are not limited to, immunogens derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Useful UPEC immunogens are disclosed in WO 2006/091517 (Chiron Corp.) and WO 2008/020330 (Novartis AG). Useful MNEC immunogens are disclosed in WO 2006/089264 (Chiron Corp.). A useful immunogen for several *E. coli* types is AcfD. See, WO 2009/104092 (Novartis AG).

*Bacillus anthracis*

*Yersinia pestis*: Useful immunogens include, but are not limited to, those disclosed in WO2007/049155 and WO2009/031043.

*Staphylococcus epidermis*

*Clostridium perfringens* or *Clostridium botulinums*

*Legionella pneumophila*

*Coxiella burnetii*

*Brucella*, such as *B. abortus, B. canis, B. melitensis, B. neotomae, B. ovis, B. suis, B. pinnipediae.*

*Francisella*, such as *F. novicida, F. philomiragia, F. tularensis.*

*Neisseria gonorrhoeae*

*Treponema pallidum*

*Haemophilus ducreyi*

*Enterococcus faecalis* or *Enterococcus faecium*

*Staphylococcus saprophyticus*

*Yersinia enterocolitica*

*Mycobacterium tuberculosis*

*Rickettsia*

*Listeria monocytogenes*

*Vibrio cholerae*

*Salmonella typhi*

*Borrelia burgdorferi*

*Porphyromonas gingivalis*

*Klebsiella*

In a forty-fourth embodiment, the immunogen elicits an immune response against one of these viruses:

Orthomyxovirus: Useful immunogens can be from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: immunogens include, but are not limited to, those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles virus).

Poxviridae: immunogens include, but are not limited to, those derived from Orthopoxvirus such as *Variola vera*, including but not limited to, *Variola major* and *Variola minor.*

Picornavirus: immunogens include, but are not limited to, those derived from Picornaviruses, such as Enteroviruses, Rhinoviruses, Heparnavirus, Cardioviruses and Aphthoviruses. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: immunogens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Heparnavirus: immunogens include, but are not limited to, those derived from a Heparnavirus, such as hepatitis A virus (HAV).

Filovirus: immunogens include, but are not limited to, those derived from a filovirus, such as an Ebola virus (including a Zaire, Ivory Coast, Reston or Sudan ebolavirus) or a Marburg virus.

Togavirus: immunogens include, but are not limited to, those derived from a Togavirus, such as a Rubivirus, an Alphavirus, or an Arterivirus. This includes rubella virus.

Flavivirus: immunogens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: immunogens include, but are not limited to, those derived from a Pestivirus, such as Bovine viral diarrhea (BVDV), Classical swine fever (CSFV) or Border disease (BDV).

Hepadnavirus: immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: immunogens include, but are not limited to, those derived from a Rhabdovirus, such as a Lyssavirus (e.g. a Rabies virus) and Vesiculovirus (VSV).

Caliciviridae: immunogens include, but are not limited to, those derived from Calciviridae, such as Norwalk virus (Norovirus), and Norwalk-like Viruses, such as Hawaii Virus and Snow Mountain Virus.

Coronavirus: immunogens include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Retrovirus: immunogens include, but are not limited to, those derived from an Oncovirus, a Lentivirus (e.g. HIV-1 or HIV-2) or a Spumavirus.

Reovirus: immunogens include, but are not limited to, those derived from an Orthoreovirus, a Rotavirus, an Orbivirus, or a Coltivirus.

Parvovirus: immunogens include, but are not limited to, those derived from Parvovirus B19.

Herpesvirus: immunogens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: immunogens include those derived from serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of Atlantic salmon), landlocked salmon virus (LSV), Atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In a forty-fifth embodiment, the immunogen elicits an immune response against a parasite from the *Plasmodium* genus, such as *P. falciparum, P. vivax, P. malariae* or *P. ovale*. Thus, the invention may be used for immunising against malaria. In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi*.

In a forty-sixth embodiment, the immunogen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and *Sorghum*, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. Lepidoglyphys, Glycyphagus and Tyrophagus, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In a forty-seventh embodiment, the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

Therapeutic Proteins

In a forty-eight embodiment, heterologous protein coding sequence of any of the preceding aspects and embodiments is a therapeutic protein, optionally wherein the therapeutic protein is selected from a growth factor, cytokine, antibody, or antigen-binding fragment of an antibody.

"Antibody," as used herein, refers to an immunoglobulin or a part thereof, and encompasses any polypeptide comprising an antigen-binding site regardless of the source, species of origin, method of production, and characteristics. As a non-limiting example, the term "antibody" includes human, orangutan, mouse, rat, goat, sheep, and chicken antibodies. The term includes but is not limited to polyclonal, monoclonal, monospecific, polyspecific, non-specific, humanized, camelized, single-chain, chimeric, synthetic, recombinant, hybrid, mutated, and CDR-grafted antibodies. For the purposes of the present invention, it also includes, unless otherwise stated, antibody fragments such as Fab, F(ab')2, Fv, scFv, Fd, dAb, VHH (also referred to as nanobodies), and other antibody fragments that retain the antigen-binding function. Antibodies also refers to antigen-binding molecules that are not based on immunoglobulins, as further described below.

Antibodies can be made, for example, via traditional hybridoma techniques (Kohler and Milstein, *Nature* 256: 495-499 (1975)), recombinant DNA methods (U.S. Pat. No. 4,816,567), or phage display techniques using antibody libraries (Clackson et al., *Nature* 352: 624-628 (1991); Marks et al., *J. Mol. Biol.* 222: 581-597 (1991)). For various other antibody production techniques, see *Antibodies: A Laboratory Manual*, eds. Harlow et al., Cold Spring Harbor Laboratory, 1988.

The term "antigen-binding domain" refers to the part of an antibody molecule that comprises the area specifically binding to or complementary to a part or all of an antigen. Where an antigen is large, an antibody may only bind to a particular part of the antigen. The "epitope" or "antigenic determinant" is a portion of an antigen molecule that is responsible for specific interactions with the antigen-binding domain of an antibody. An antigen-binding domain may be provided by one or more antibody variable domains (e.g., a so-called Fd antibody fragment consisting of a VH domain). An antigen-binding domain can comprise an antibody light chain variable region (VL) and an antibody heavy chain variable region (VH). Antibodies from camels and llamas (Camelidae, camelids) include a unique kind of antibody, which is formed by heavy chains only and is devoid of light chains. The antigen-binding site of such antibodies is one single domain, referred to as VHH. These have been termed "camelized antibodies" or "nanobodies". See, e.g., U.S. Pat. Nos. 5,800,988 and 6,005,079 and International Application Publication Nos. WO 94/04678 and WO 94/25591, which are incorporated by reference. In some embodiments, the "antibody" includes an antigen-binding molecule based on a scaffold other than an immunoglobulin. For example, non-immunoglobulin scaffolds known in the art include small modular immunopharmaceuticals (see, e.g., U.S. Patent Application Publication Nos. 20080181892 and 20080227958 published Jul. 31, 2008 and Sep. 18, 2008, respectively), tetranectins, fibronectin domains (e.g., AdNectins, see U.S. Patent Application Publication No. 2007/0082365, published Apr. 12, 2007), protein A, lipocalins (see, e.g., U.S. Pat. No. 7,118,915), ankyrin repeats, and thioredoxin. Molecules based on non-immunoglobulin scaffolds are generally produced by in vitro selection of libraries by phage display (see, e.g., Hoogenboom, *Method Mol. Biol.* 178:1-37 (2002)), ribosome display (see, e.g., Hanes et al., *FEBS Lett.* 450:105-110 (1999) and He and Taussig, *J. Immunol. Methods* 297:73-82 (2005)), or other techniques known in the art (see also Binz et al., *Nat. Biotech.* 23:1257-68 (2005); Rothe et al., *FASEB J.* 20:1599-1610 (2006); and U.S. Pat. Nos. 7,270,950; 6,518,018; and 6,281,344) to identify high-affinity binding sequences.

Delivery Systems

Nucleic acids provided by the invention can be delivered by any suitable means. They may be delivered naked, in an aqueous solution (such as a buffer), or with a delivery system, such as an adjuvant delivery system. Accordingly, in another aspect, a nucleic acid provided by the invention may be complexed with a delivery system. Exemplary delivery systems include a viral replicon particle (VRP), a lipid nanoparticle (LNP), a cationic nanoemulsion (CNE), or a biodegradeable polymer. Useful delivery systems for the nucleic acids provided by the invention are described in, inter alia, for CNEs, published International patent applications WO 2012/006380, WO 2013/006837, WO 2013/006834. For LNPs, see WO 2012/006378, WO 2012/030901, WO 2012/031046, WO 2012/031043, WO 2013/033563, WO 2013/006825, WO 2011/076807, WO 2015/095340 (Novaais AG) and WO 2015/095346 (Novartis AG). For other modalities, see WO 2012/006359 or WO 2012/006376. All of the forgoing applications are incorporated by reference.

Compositions

In another aspect, the invention provides compositions comprising any nucleic acid provided by the invention, such as pharmaceutical compositions, e.g., suitable for administration to a subject, such as a human subject. Such pharmaceutical compositions may comprise suitable excipients known to the skilled artisan. In some embodiments, the nucleic acid is a self-replicating RNA provided by the invention. In some more particular embodiments, the composition further comprises an adjuvant, such as a metal salt.

In a forty-ninth embodiment, any of the compositions provided by the invention may further comprise a TLR agonist, such as a TLR7 agonist, such as a benzonapthyridine compound. TLR agonists, and formulations containing them are known in the art and are described in, inter alia, WO 2009/111337, WO 2011/049677, WO 2011/027222, WO 2011/084549, WO2012/031140, WO2013/131985, WO2012/103421, which are all incorporated by reference.

Methods of Use

In another aspect, the invention provides methods of expressing a protein of interest, or a nucleic acid encoding the protein of interest. These methods include the steps of contacting a nucleic acid provided by the invention with an expression system comprising transcriptional machinery, translational machinery, or transcriptional machinery and translational machinery, wherein the heterologous protein coding sequence of the nucleic acid is the protein of interest. In some embodiments, the expression system is a cell-free in vitro transcription system, optionally wherein the nucleic acid is a DNA sequence encoding the self-replicating RNA. In other embodiments, the expression system comprises a translation system, e.g., where the nucleic acid provided by the invention is a self-replicating RNA provided by the invention.

In a fiftieth embodiment, the expression system is a eukaryotic cell. In more particular embodiments, the eukaryotic cell is an insect cell. In other particular embodiments, the eukaryotic cell is a mammalian cell, such as a CHO cell or a COS cell.

In another aspect, the invention provides methods of raising an immune response to an antigenic protein in a mammalian subject, comprising administering a self-replicating RNA provided by the invention to the subject, where the self-replicating RNA encodes the immunogen.

In yet another aspect, the invention provides methods of administering a therapeutic protein to a mammalian subject, comprising administering a self-replicating RNA provided by the invention to the subject, wherein the self-replicating RNA encodes the therapeutic protein.

In certain particular embodiments of the methods provided by the invention, the mammalian subject is a human.

EXAMPLES

Initial Flavivirus Replicon Design and Evaluation

Figure 1:
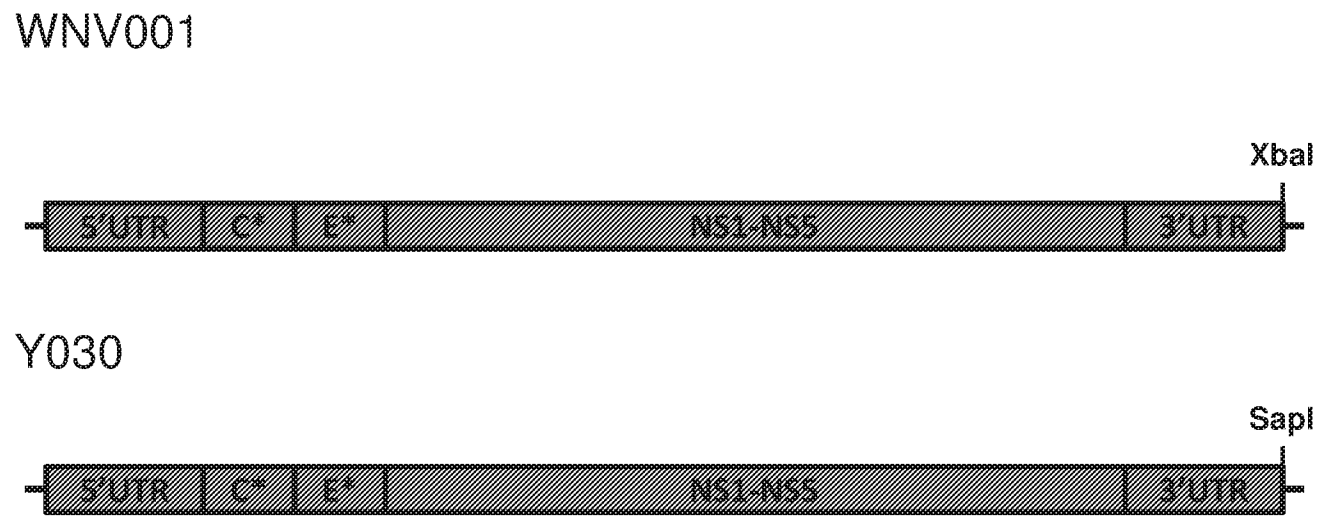

A first generation West Nile Virus (WNV) replicon was constructed from the sequence of WNV Strain 3356 (GenBank: AF404756.1). Shi P. Y., Tilgner M., Lo M., "Construction and Characterization of Subgenomic Replicons of New York Strain of West Nile Virus." *Virology* 296: 213-233 (2002). The WNV sequence, including the nt. 90-2379 deletion, was ordered in three fragments from Genewiz and assembled into a low-copy, p15A origin of replication vector using traditional cloning methods with a traditional T7 promoter sequence upstream of the WNV replicon sequence yielding WNV001 (FIG. 1). The deletion preserves the N-terminal coding region of protein C (nt. 97-189); the corresponding RNA sequence is an essential cis-acting element and may play a role in the regulation of minus-sense RNA synthesis. See Hahn, C. et al. *J. Mol. Biol.* 198, 33-41 (1987); Khromykh, A. A. and Westaway, E. G., *J. Virol.* 71(2), 1497-1505 (1997); and Westaway, E. G. *Adv. Virus Res.* 33, 45-90 (1987). The C-terminal coding sequence of E protein (nt. 2380-2469) was preserved as this region acts as a signal sequence guiding the translocation and processing of non-structural protein 1 (NS1) and subsequently the remaining non-structural proteins NS2-NS5. Both regions are required for replication of the RNA genome. These deletions render WNV non-infectious but replication competent. The full WNV replicon sequence was assembled into a low-copy plasmid vector as there is instability when the full-length WNV replicon sequence is cloned into high-copy plasmids.

A Yellow Fever vVrus (YFV) replicon was constructed using similar principles and based on the sequence of YFV 17D vaccine strain (GenBank: X15062.1) to yield replicon Y030. The YFV replicon contains structural gene deletions rendering it non-infectious but replication competent. The coding region corresponding to the 25 N-terminal amino acids of protein C and the 24 C-terminal amino acids of protein E were preserved to retain elements necessary for replicon function, similar to the WNV replicon. (FIG. 1).

WNV001 replicon RNA was functionally evaluated via electroporation into baby hamster kidney (BHK) cells followed by staining for the presence of WNV antigen using immunohistochemical (IHC) methods. Replicon RNA from a non-infectious, vaccine strain of Venezuelan equine encephalitis (VEE; see Geall, A. J. et. al., *Proc. Natl. Acad. Sci. U.S.A.* 109(36): 140604-14609 (2012)) expressing WNV-NS1 (A609) was used as a positive control. IHC was performed 48 hr post-electroporation using WNV hyperimmune mouse ascites fluid as the primary antibody (a gift from R.B. Tesh) and horseradish peroxidase conjugated goat anti-mouse IgM (H+L) as a secondary antibody. Positive cells were identified by a blue residue left upon reacting with TrueBlue peroxidase substrate. As expected, cells electroporated with A609 demonstrated a strongly IHC positive signal, however, less than 1% of cells electroporated with WNV001 demonstrated an IHC positive signal (FIG. 2).

Flow-cytometry was used to evaluate function of the yellow fever replicon via electroporation of 1 µg Y030 RNA into BHK cells followed by staining for the presence of YFV antigen. Cells were harvested 24 hr post-electroporation and stained using YFV hyperimmune mouse ascites fluid as the primary antibody (a gift from R.B. Tesh) and allophycocyanin (APC) conjugated goat anti-mouse $IgG_{2a}$. Positive cells were identified by fluorescence using the APC channel during flow-cytometric analysis. (FIG. 3)

Hepatitis Delta Virus Ribozymes Enhance WNV Replicon Potency but not YFV Replicon Potency Results with the first generation WNV001 replicon demonstrated poor potency (defined as the percent of cells expressing antigen or a reporter gene post-electroporation or transfection). To improve the potency of the replicon, sense or anti-sense hepatitis delta virus sequences (S-HDVR or AS-HDVR respectively) were added immediately downstream of the 3'UTR of WNV001, yielding second-generation replicons WNV006 and WNV007 containing the S-HDVR or AS-HDVR, respectively (FIG. 4).

Replicon RNA of WNV001, WNV006, and WNV007 was evaluated in BHK cells using flow-cytometry. A range of WNV001, WNV006, or WNV007 RNA (0.25 µg to 4 µg) was electroporated into BHK cells and 24 hr post electroporation, cells were stained with WNV hyperimmune mouse ascites fluid and allophycocyanin (APC) conjugated goat anti-mouse $IgG_{2a}$ (FIG. 5). Cells which were electroporated with second-generation WNV replicon RNA demonstrated ~5-fold to 10-fold more WNV antigen positive cells than the first generation WNV replicon, indicating that the addition of S-HDVR or AS-HDVR significantly improved potency as quantified via flow-cytometry. At all ranges tested, cells electroporated with WNV006 RNA, containing the S-HDVR, demonstrated the highest potency.

Figure 6:
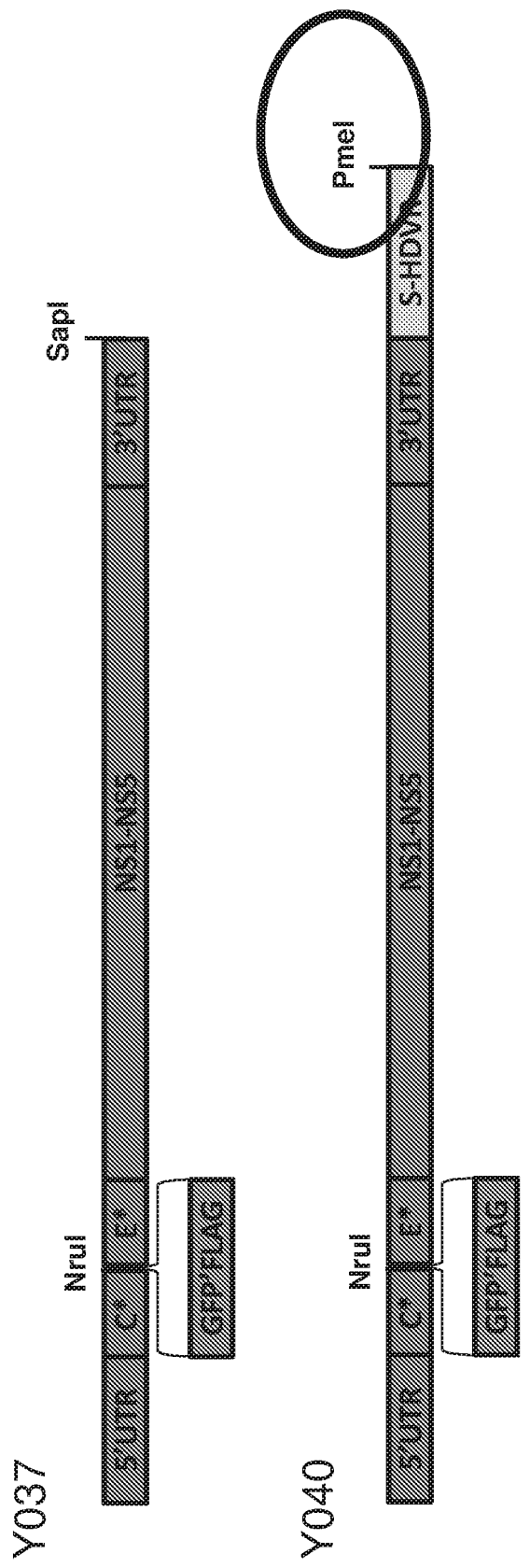
FIG. 6 is a schematic of replicons used to evaluate effects of S-HDVR on YFV replicon potency. Both replicons contained GFP with a FLAG tag reporter fused in-frame within the structural deleted region.
Figure 7:
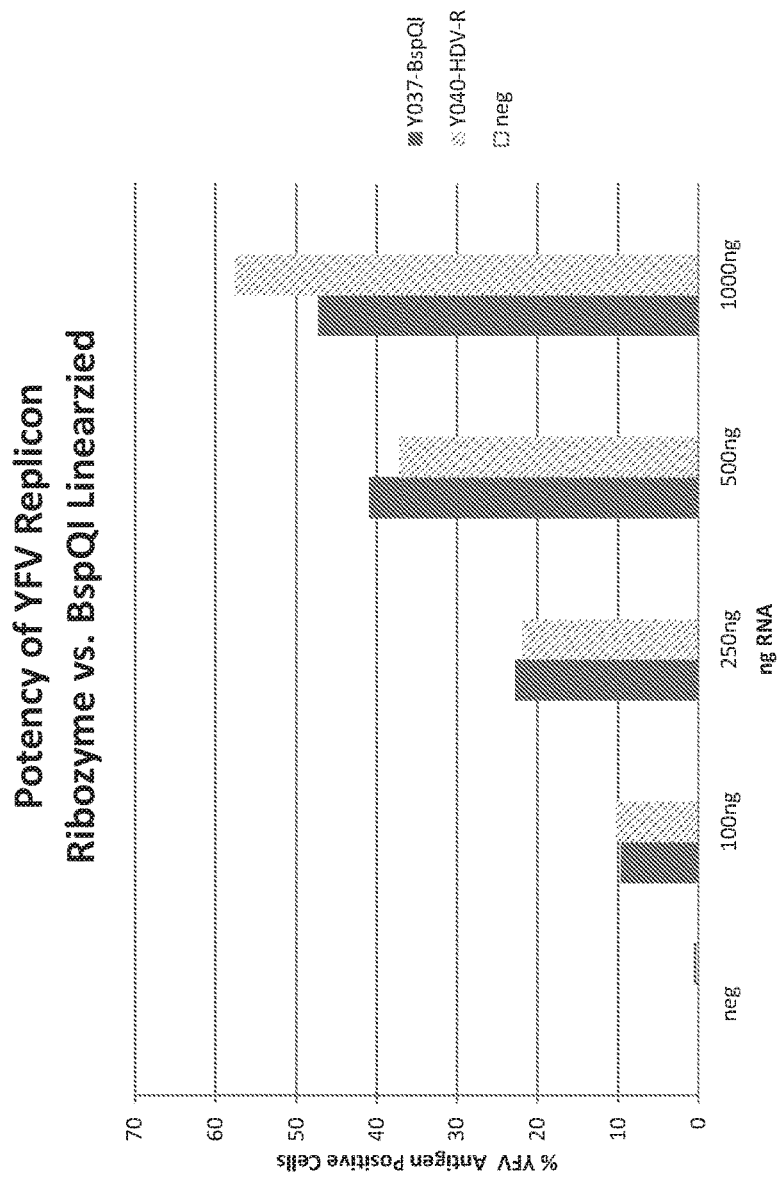
FIG. 7 is a bar graph illustrating that addition of HDV ribozyme does not enhance YFV replicon potency. Briefly, 0.1 μg-1 μg of Y037 or Y040 RNA was electroporated into BHK cells. Cells were analyzed for the presence of YFV antigen via flow cytometry 24 hr post-electroporation. The results indicate that the sense HDVR does not have a significant effect on YFV potency.

We tested whether YFV RNA potency was further improved with the addition of a HDV-R sequence following the 3'UTR based on the results obtained using WNV replicons. The ribozyme was added directly after the 3' UTR of Y037 (based on Y030 with a GFP reporter) generating Y040. (FIG. 6) To test the effect of the HDV-ribozyme on potency, BHK cells were electroporated with a range of Y037 or Y040 RNA (0.1-1 µg) and the percentages of YFV antigen positive cells were determined by flow-cytometry 24 hr post electroporation. The use of ribozyme did not appreciably improve YFV replicon RNA potency unlike the results obtained with WNV replicons. (FIG. 7)

We tested whether the mechanism by which the addition of a ribozyme sequence improves potency of the WNV replicon is that it facilitates the development of a native 3' UTR after in vitro transcription. This was evaluated this by comparing RNA generated from the following templates: (1) XbaI linearized and exonuclease polished WNV001, (2) PCR generated WNV001 template, and (3) Ribozyme containing XbaI linearized WNV006. Theoretically, all templates used to generate WNV replicon RNA yield the same sequence, however, the potency of RNA generated with the assistance of the ribozymes greatly outperformed that of RNA generated from the XbaI, exonuclease polished or PCR generated templates. See FIGS. 15-17.

In vitro transcription of WNV replicon RNA using XbaI linearized and exonuclease polished WNV001 or PCR generated WNV001 template may suffer from poor potency as many transcripts may contain non-native 3' ends due to aberrant addition of non-templated nucleotides; transcripts without a native end may be functionally impaired or nonfunctional. The addition of a ribozyme facilitates the development of precisely defined, native 3' ends perhaps explaining the superiority of WNV replicon RNA generated using this method.

The addition of HDV-R to yellow fever replicons did not have the same effect, however, the YFV replicon had a markedly high potency to begin with compared to WNV (e.g., 1 µg of YFV replicon RNA electroporated into BHK cells typically yields 60-70% YFV antigen positive cells compared to 4 µg of WNV001 or WNV006 replicon RNA yielding ~1.5% to ~9% WNV antigen positive cells respectively). Thus, the the 3' UTR of YFV replicon RNA was already effectively optimized without additional modifications.

5' ATP-Initiated Promoters Improve Flavivirus Replicon Potency

The results from the second-generation WNV replicons suggested that addition of the ribozyme aids in the generation of an authentic 3' end of the replicon RNA during in vitro transcription. We tested whether the WNV replicon potency was further enhanced through modifications that would facilitate the development of authentic 5' end of the replicon RNA. Thus far, a traditional T7 class III phi 6.5 promoter was used to drive transcription of WNV replicon RNA; this promoter is GTP-initiated, leading to the addition of one extra, non-viral guanosine to the 5' end of the replicon RNA. It has been demonstrated that flavivirus virus recovery is low when genomic viral RNA containing the extra guanosine nucleotide from transcription using a traditional T7 class III phi 6.5 promoter was used. Furthermore, the 5' end of replicon RNA is being corrected during its replication in cells to revert to the authentic sequence. See, e.g., Khromykh and Westaway, J Virol, 68(7): p. 4580-8 (1994).

To facilitate the production of WNV replicon RNA with a correct 5' end, a series of alternative T7 promoters that drive ATP-initiated transcription was generated by modifying the promoter of WNV008 (based on WNV006 but with a silent mutation between C* and E* to develop an AflII cloning site), yielding WNV replicons WNV017, WNV026, WNV027, and WNV028 (FIG. 8A) WNV017 replicon RNA was generated by T7 class II phi 2.5 promoter (Coleman et al., *Nucleic Acids Res*, 32(1): p. e14 (2004)), while WNV026 was transcribed using a mutant T7 phi 6.5 promoter which contained a G to A substitution. The overlapping promoters (OL) where the last nucleotide of these promoters overlapped with the first nucleotide of the flavivirus replicon RNA were also tested. Transcription of WNV027 was driven by T7 promoter phi 2.5 (OL) and WNV028 by T7 promoter phi 6.5 mut (OL).

Promoter modifications were first tested to determine if they were detrimental to transcription efficiency compared to the previously used T7 promoter driving transcription of WNV008. phi 2.5 and phi 6.5 mutant promoters used in WNV017 and WNV026, respectively, severely reduced RNA yield in in vitro transcription, but phi 2.5 (OL) and phi 6.5 mut (OL) promoters used in WNV027 and WNV028, respectively, did not have a significant detrimental effect on RNA yield (FIG. 8B). Potency of RNA transcribed using the modified T7 promoters was evaluated by electroporation of 100 ng of replicon RNA into BHK cells and determining the percentage of WNV antigen positive cells at 24 hr by flow cytometry (FIG. 9). The data indicated that third generation WNV replicons, driven by A-initiated, T7 promoters during transcription, were significantly more potent than the second-generation WNV replicon except for WNV026. RNA from WNV027 and WNV028 were approximately 15-fold higher in potency compared to WNV008.

The effects of using ATP-initiated, modified promoters was also evaluated in the YFV replicon system by modifying the promoter of Y037 (based on Y030 with a GFP reporter flanked by F2A and GSGP2A self-cleaving peptide sites derived from foot and mouth disease virus and porcine teschovirus, respectively). As preformed with WNV, promoter modifications were first tested to determine if they were detrimental to transcription efficiency of YFV replicons. Alternative promoters yielded 60% as much RNA compared to the traditional promoter (FIG. 8C). Potency of RNA transcribed using the modified T7 promoters was evaluated by electroporation of 100 ng of replicon RNA into BHK cells and determining the percentage of YFV antigen positive cells at 24 hr by flow cytometry (FIG. 10). The data showed that ATP-initiated promoters also improved the potency of YFV replicons; however, the maximum potency improvement using an ATP-initiated promoter was only ~2-fold greater than GTP-initiated RNA using the traditional promoter.

Optimization of Transgene Expression Site

Two different strategies of developing heterologous gene expressing flavivirus replicons were evaluated. One strategy consists of inserting an EMCV IRES driven reporter gene in an upstream region of the 3' UTR. The second strategy focused on adding the reporter gene as an in-frame replacement within the structural deleted region. Attempts to add IRES-driven reporter genes into upstream regions of the 3'UTR of WNV or YFV replicons yielded replicons with poor potency and expression of the inserted transgene. In contrast, reporter genes which were inserted in-frame into the structural-deleted deleted region of the replicons yielded potent replicons with higher expression of the reporter. See FIGS. 18-21. Optimizing the insertion of genes within this region was a future focus.

Figure 11:
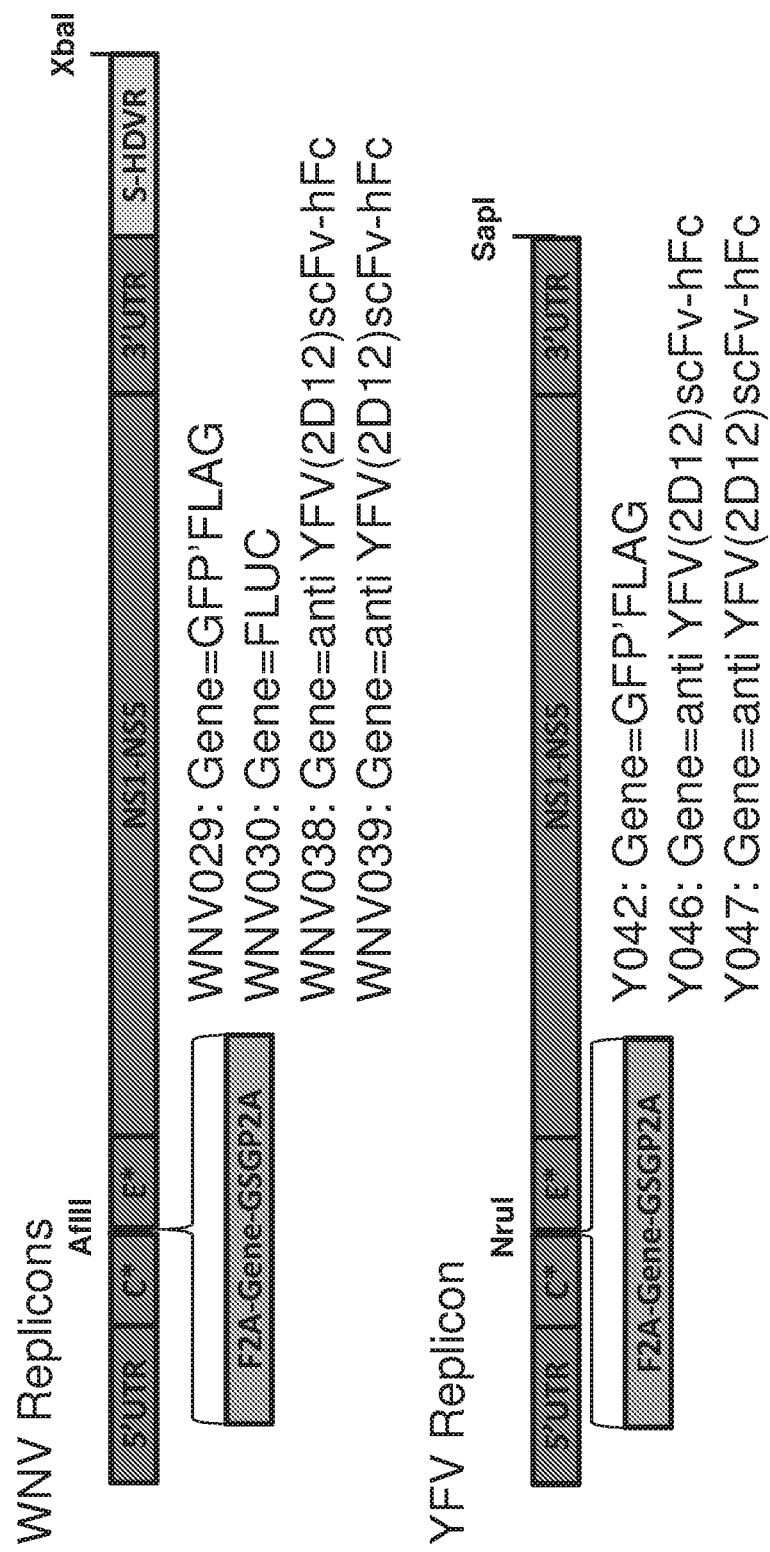
FIG. 11 provides a schematic of WNV or YFV replicons with optimized transgene expression cassettes inserted into the structural deleted region. Optimized WNV constructs contain both an overlapped ATP-initiated promoter and a ribozyme. Optimized YFV constructs contain an ATP-initiated promoter and precise linearization site.

Transgenes such as GFP with FLAG tag (GFP'FLAG), firefly luciferase (FLUC), and anti-YFV antibody fragments (scFv-hFc) were inserted into the structural deleted gene region of optimized WNV or YFV base replicons flanked by F2A and GSGP2A self-cleaving peptides (FIG. 11). GFP-'FLAG, FLUC, or scFv-hFc expressing WNV replicon RNA, and GFP'FLAG or scFv-hFc expressing YFV replicon RNA was evaluated in vitro and all were capable of expressing the transgene of interest. See FIGS. 22-25.

Flavivirus Replicons have Alternate Characteristics Compared to Alphavirus Replicons.

The properties of WNV, YFV, and TC83 based replicons across various metrics using GFP expressing replicons in multiple cell lines were evaluated.

Figure 13:
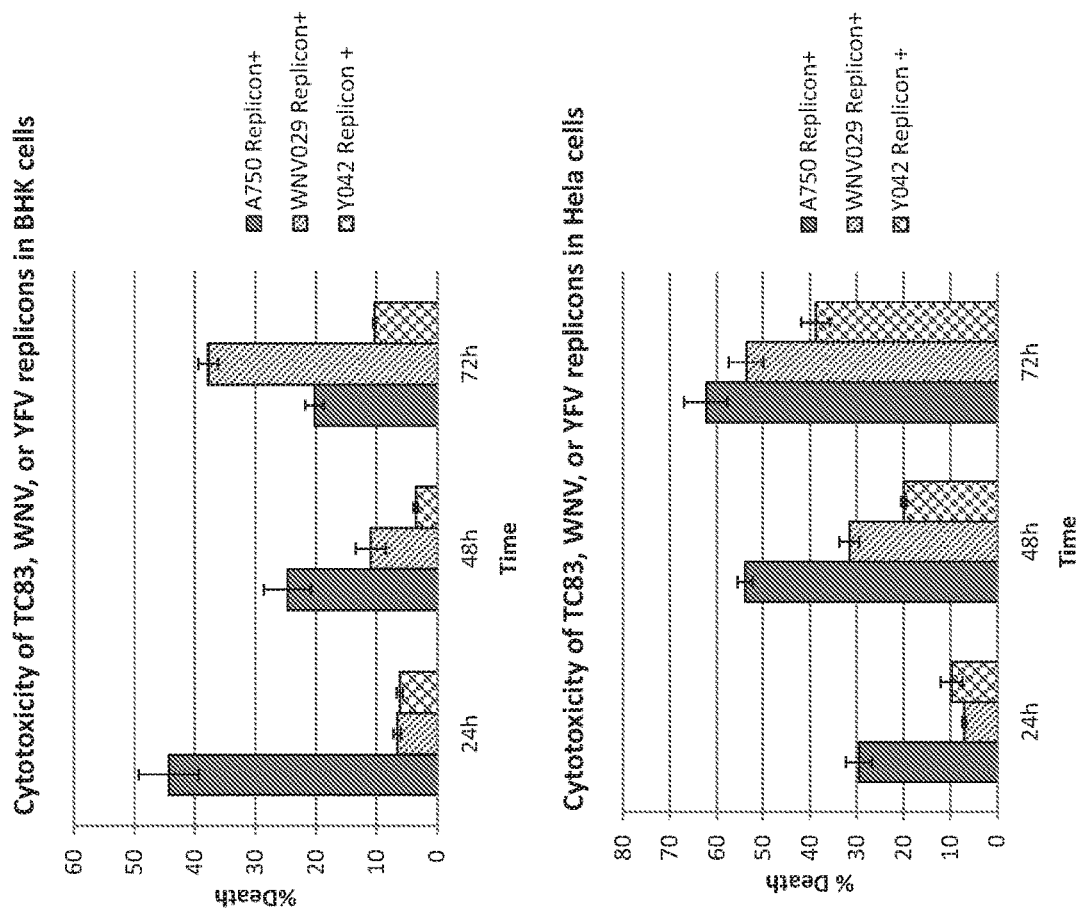
FIG. 13 is a bar graph illustrating that the YFV and WNV replicons are less cytotoxic that TC83 replicons. Briefly 250 ng of each RNA was transfected into BHK or Hela cells and cytotoxicity was determine by the percentage of dead, replicon positive cells at 24, 48, and 72 hr post transfection.
Figure 14:
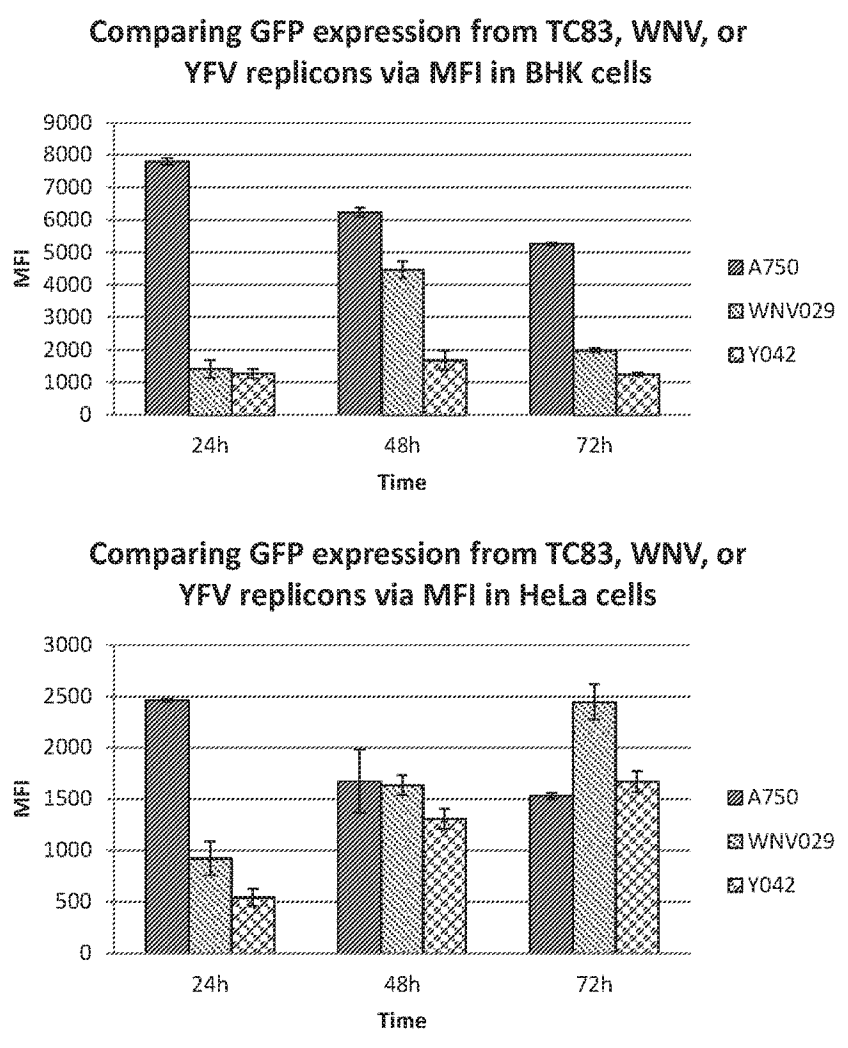

Replicon potency, cytotoxicity, and expression was determined in BHK or HeLa cells using cationic transfection reagents to better standardize transfection conditions when working with different cell lines. Briefly, 250 ng of replicon RNA from GFP expressing TC83, WNV, or YFV replicons (A750, WNV029, or Y042) were transfected onto a 80% confluent layer of BHK or HeLa cells using MIRUS mRNA transfection reagents (Mirus) in 6-well format. Supernatants and cell layers from each well were harvested at 24 hr, 48 hr, and 72 hr time points and were stained using a far-red live/dead staining reagent (Molecular Probes) which penetrates into compromised membranes of pre-apoptotic and apoptotic cells. Using flow-cytometric analysis, replicon potency was determined using the live-cell population and determining the percentage of GFP+ cells to total live cells (FIG. 12). Replicon cytotoxicity was determined using GFP+ cells and determining the percentage of dead GFP+ cells compared to total GFP+ cells (FIG. 13). Expression was determined by the mean fluorescence intensity of live, GFP+ cells (FIG. 14).

The potency results using BHK cells indicated that at 24 hr, the TC83-based replicon A750 was approximately equivalent in potency compared to WNV029. Y042 had a much lower potency than the other replicons. The data suggests that potency is retained by all three replicons in comparing 24 hr to 48 hr potency. In comparing potency at 48 hr to 72 hr, there was a drastic drop in potency in cells transfected with either the A750 or WNV029 replicon, but Y042 appears to still maintain potency at this time. Potency results using HeLa cells demonstrated that the WNV replicon is as potent as the TC83-based replicon, while the YFV-based replicon suffers from poor potency in HeLa cells. Additionally, the potency was better retained by WNV replicon transfected cells than TC83 replicon cells at 48 hr, but the potency dropped to approximately equal levels at 72 hr.

In BHK cells, the GFP expressing TC83 replicon (A750) exhibited higher levels of cytotoxicity than the GFP expressing flavivirus replicons. However, the 72 hr time-point had indicated that cells harboring a WNV replicon had a greatly increased cell death percentage from ~9% to ~54%. There are many possible reasons for this, but one major reason is that the live/dead staining system can only detect cells with compromised membranes, but not cells which have completely lysed. Cells transfected with the A750 replicon may have experienced a much more drastic level of apoptosis at earlier time points and may have been too damaged to be detected by the live/dead staining assay at the 48 hr and 72 hr marks and thus, the apparent level of cytotoxicity may be underestimated in this test condition. In contrast, the milder cytotoxicity of the WNV replicon may have introduced many cells which were membrane compromised, but not completely destroyed. Thus, there would be an increased apparent cytotoxicity in the 72 hr sample. This can be further investigated, but the results thus far and the methods by which the live-dead stain functions may indicate that the TC83-based replicons are extremely cytotoxic compared to flaviviral replicons. Cytotoxicity data using HeLa indicated that the TC83 replicon was the most cytotoxic at all time-points as expected followed by the WNV replicon and the YFV replicon. Levels of cytotoxicity increased for all replicons throughout the duration of the experiment.

Expression data in BHK cells demonstrates that GFP expression from the TC83-replicon drop over time, most likely due to the cytotoxic effect. GFP expression from the WNV replicon was initially low but increases significantly at 48 hr followed by a drop again at 72 hr. Expression of GFP from the YFV replicon appeared to be stable. In HeLa cells, GFP expression from the TC83-replicon continued to drop as it did in BHK cells, however, expression of GFP from flaviviral replicons continues to increase throughout the duration of the experiment.

The results demonstrate the different properties of flavivirus replicons compared to the TC83 replicon platform and the potential for flavivirus replicons.

FIGS. 15-25 provide supplemental data described further, infra and in their descriptors, supra.

Figure 16:
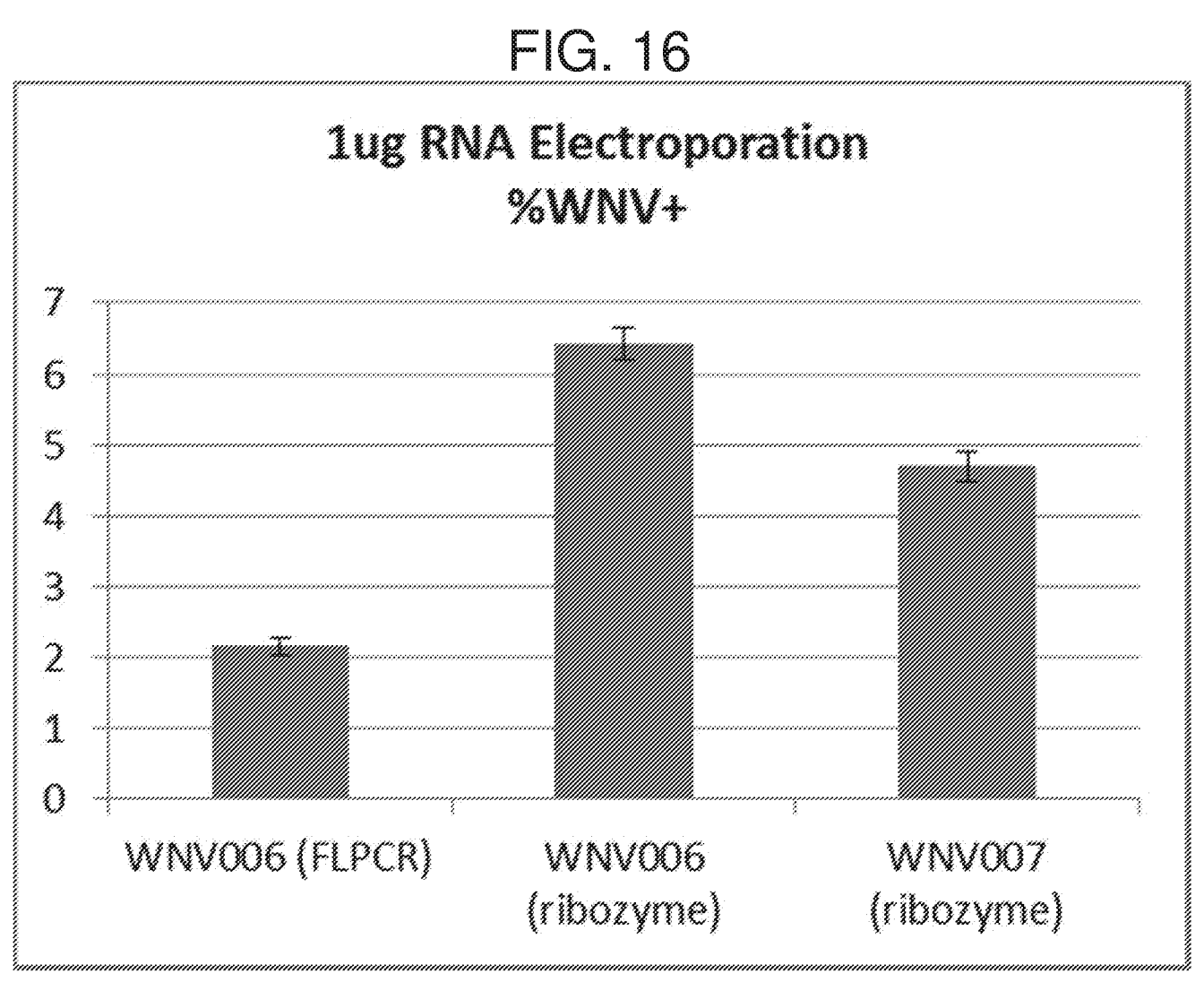
Figure 17:
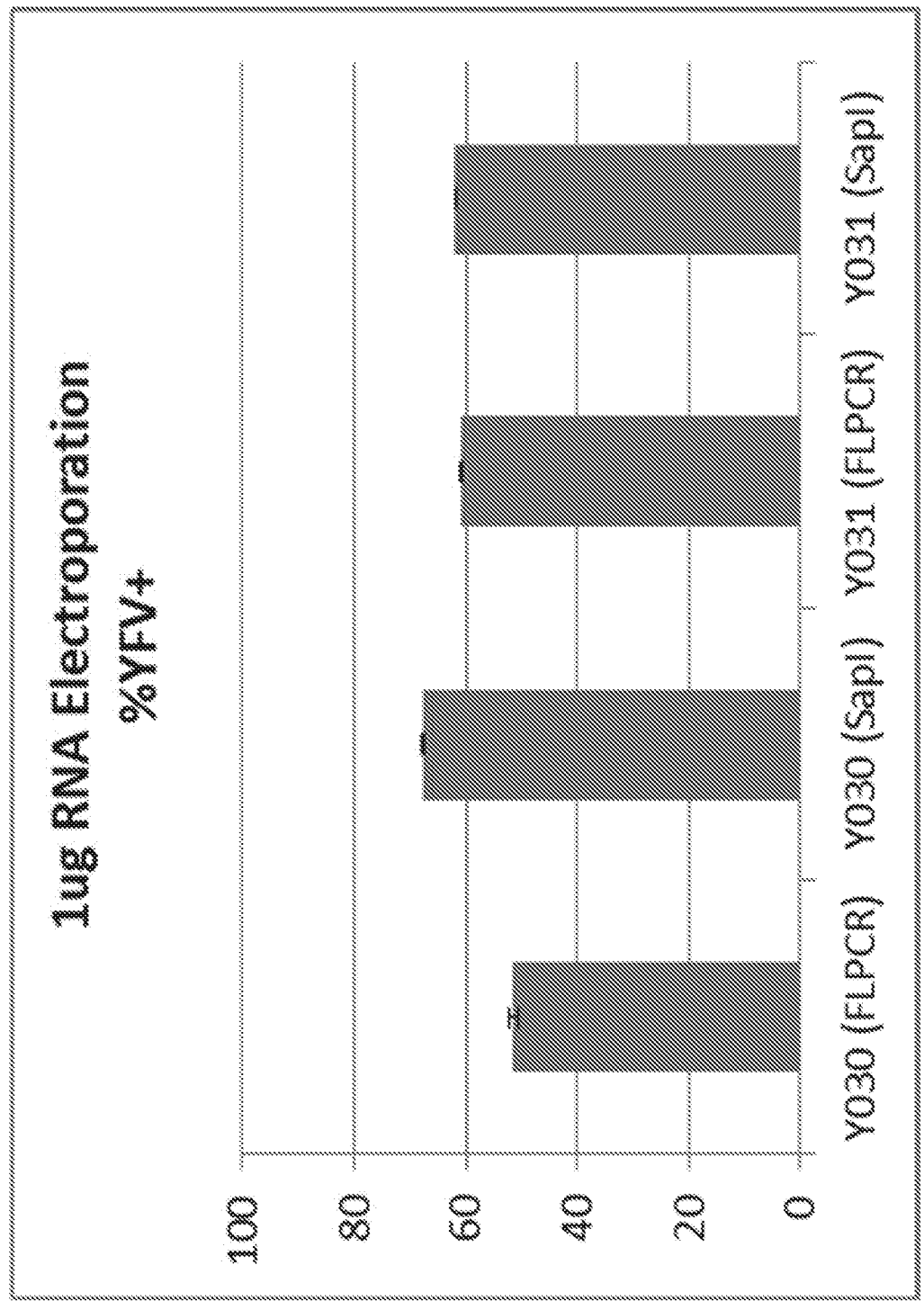
FIG. 17 is a bar graph demonstrating that YFV replicon RNA derived from DNA templates generated via PCR or SapI linearization were equivalent in potency Template DNA of Y030 or Y031 was developed using PCR to generate a perfect run-off end. Alternatively, template DNA of Y030 and Y031 was generated using an engineered SapI site to generate a perfect run-off end.

For FIGS. 15-17, WNV replicon RNA generated with the assistance of sense or anti-sense HDV-R sequence added to the 3'UTR of the template was superior to WNV replicon RNA generated from a template generated via XbaI/Mung Bean exonuclease treatment or PCR generated template.

Data Demonstrating Optimization of Reporters

In FIGS. 18-22, two different strategies of developing heterologous gene expressing flavivirus replicons were evaluated. One strategy consisted of inserting an EMCV IRES driven reporter gene in an upstream region of the 3' UTR. Shi et al. *Virology* 296, 213-233 (2002); Khromykh and Westaway *J. Virol.* 71(2), 1497-1505 (1997). Another strategy focused on adding the reporter gene as an in-frame replacement within the structural deleted region. Jones et al. *Virology* 331 247-259 (2005). In WNV replicons based on WNV006, various methods of inserting a FLFPD.RSVF-FurinF2A-GFP dual reporter cassette which would allow for efficient transgene expression were evaluated. Reporter optimization was performed on WNV replicons containing only the ribozyme 3' UTR optimization as the 5' UTR optimization was not yet discovered during these studies.

Figure 18:
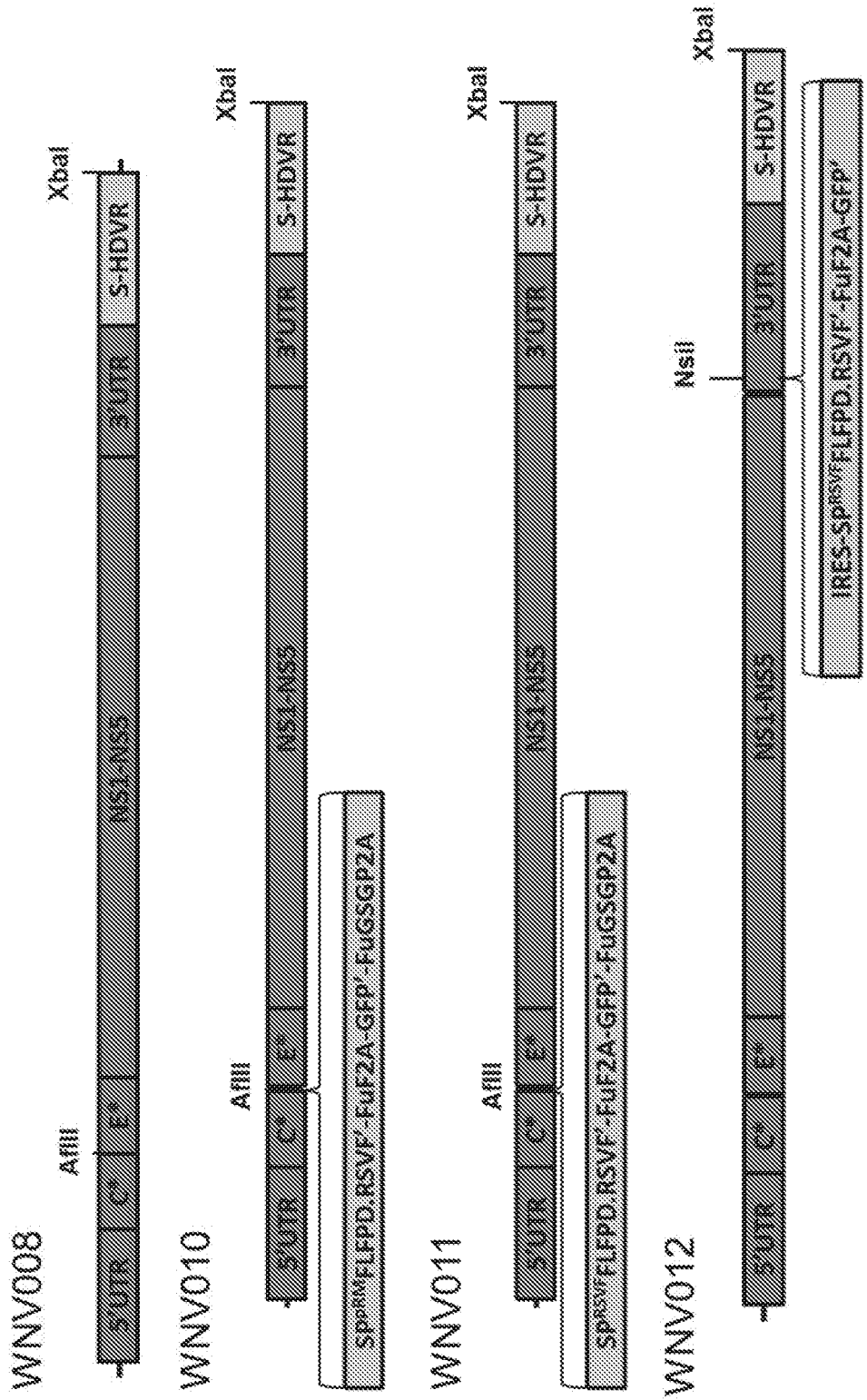
FIG. 18 shows schematics of additional constructs. Addition full-length fusion peptide respiratory syncytial virus F protein (FLFPD.RSFV) and GFP dual reporter cassette into second generation WNV008 construct derived from WNV006 (an AflII cloning site was engineered between the remaining portions of C and E protein in the structural deleted region for cloning purposes); from WNV008 (WNV replicon with no reporter cassettes added and sense-HDVR), from WNV010 (FLFPD.RSVF' and GFP' dual reporter cassette inserted into the structural deleted region. Both FLFPD.RSVF' and GFP' were tagged with a C-terminal FLAG tag represented by The native FLFPD.RSVF signal peptide was replaced by sequence from the C-terminal of structural protein C that normally acts as the signal peptide for structural protein prM. FLFPD.RSVF and GFP are both separated by a furin protease site and F2A autoproteolytic site from foot and mouth disease virus. A similar furin protease and GSGP2A autoproteolytic site from porcine teschovirus was added after GFP' to separate it from the viral polypeptide.) from WNV011 (A similar reporter was added into the structural deleted region except the native signal peptide of RSVF.FLFPD was preserved0 or from WNV012 (A similar reporter was added into an upstream region of the 3' UTR using the native NsiI site present. The reporter is the same as the one present in WNV011; however, the additional Furin+GSGP2A sequence was replaced with a stop codon instead).

Three FLFPD.RSVF-FurinF2A-GFP expressing replicons were developed. Two contained the reporter cassette in the structural deleted region. Of the replicons expressing the cassette from the structural deleted region, one contained the viral pRM signal peptide to drive processing of RSVF while the other contained the native RSVF signal peptide; both of these constructs contained an additional GSGP2A autoproteolytic cleavage site following GFP (WNV010 or WNV011]). The third replicon contained the EMCV-IRES driven FLFPD.RSVF-FurinF2A-GFP reporter cassette in an upstream region of the 3'UTR which was added using the native NsiI site (WNV012). FLAG tags were also added to the C-terminus of both RSVF and GFP reporter constructs. (FIG. 18).

Figure 19A:
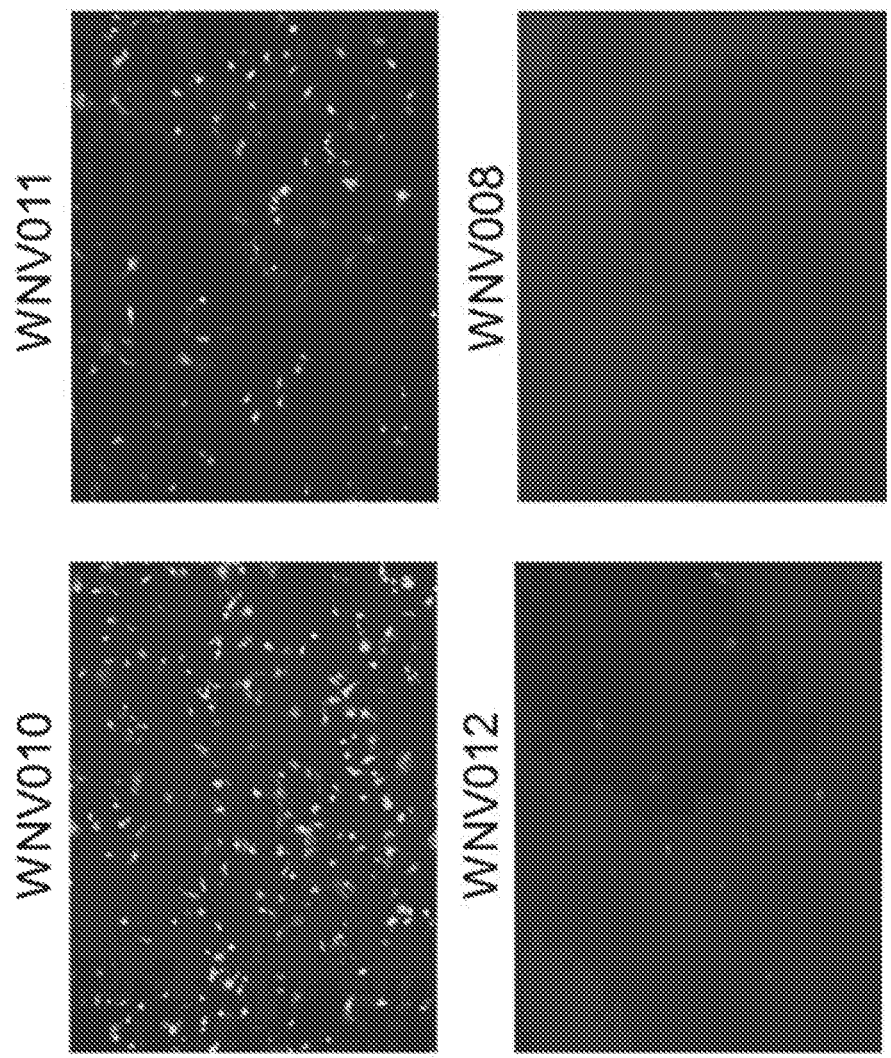
Figure 19C:
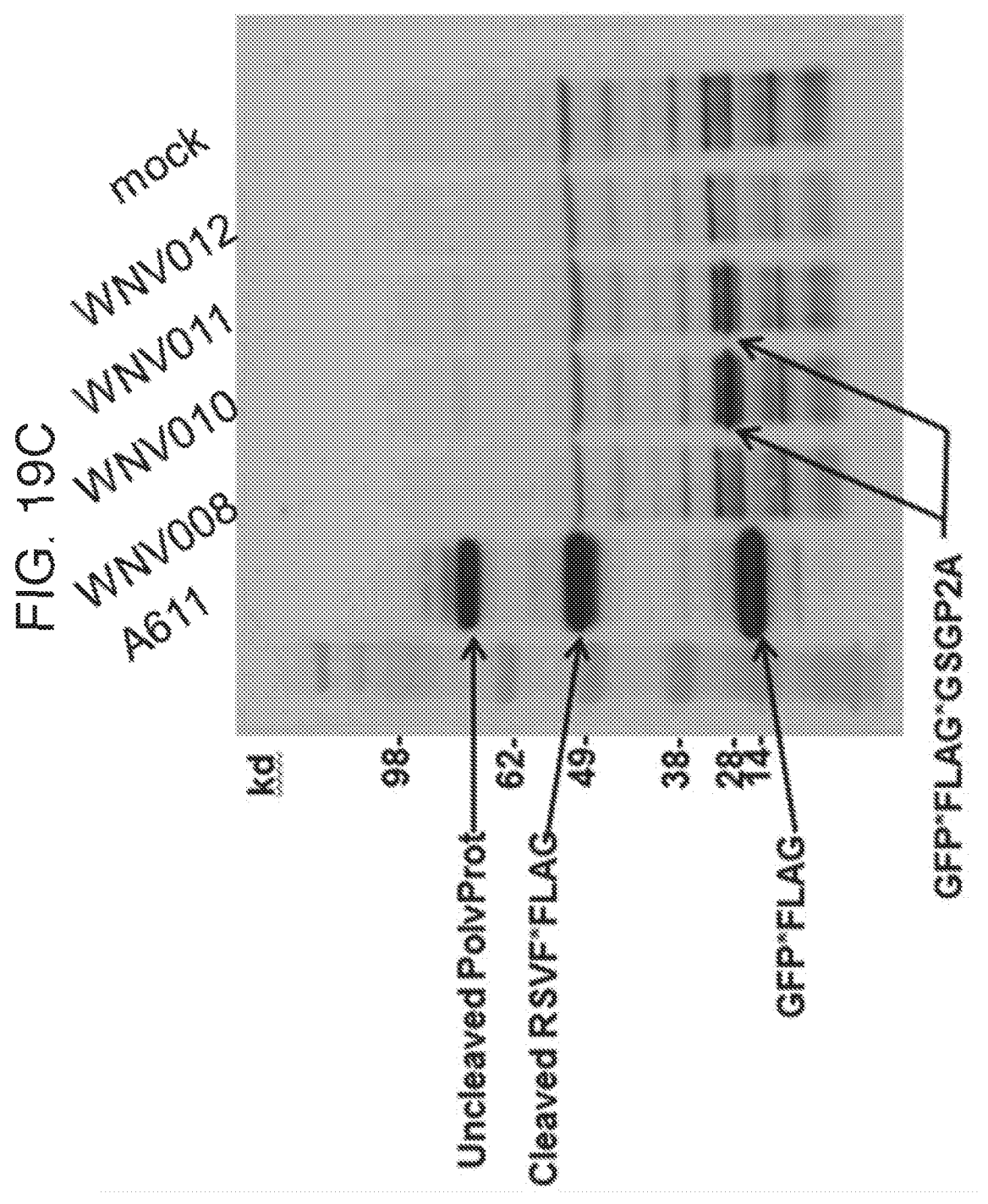
Figure 20:
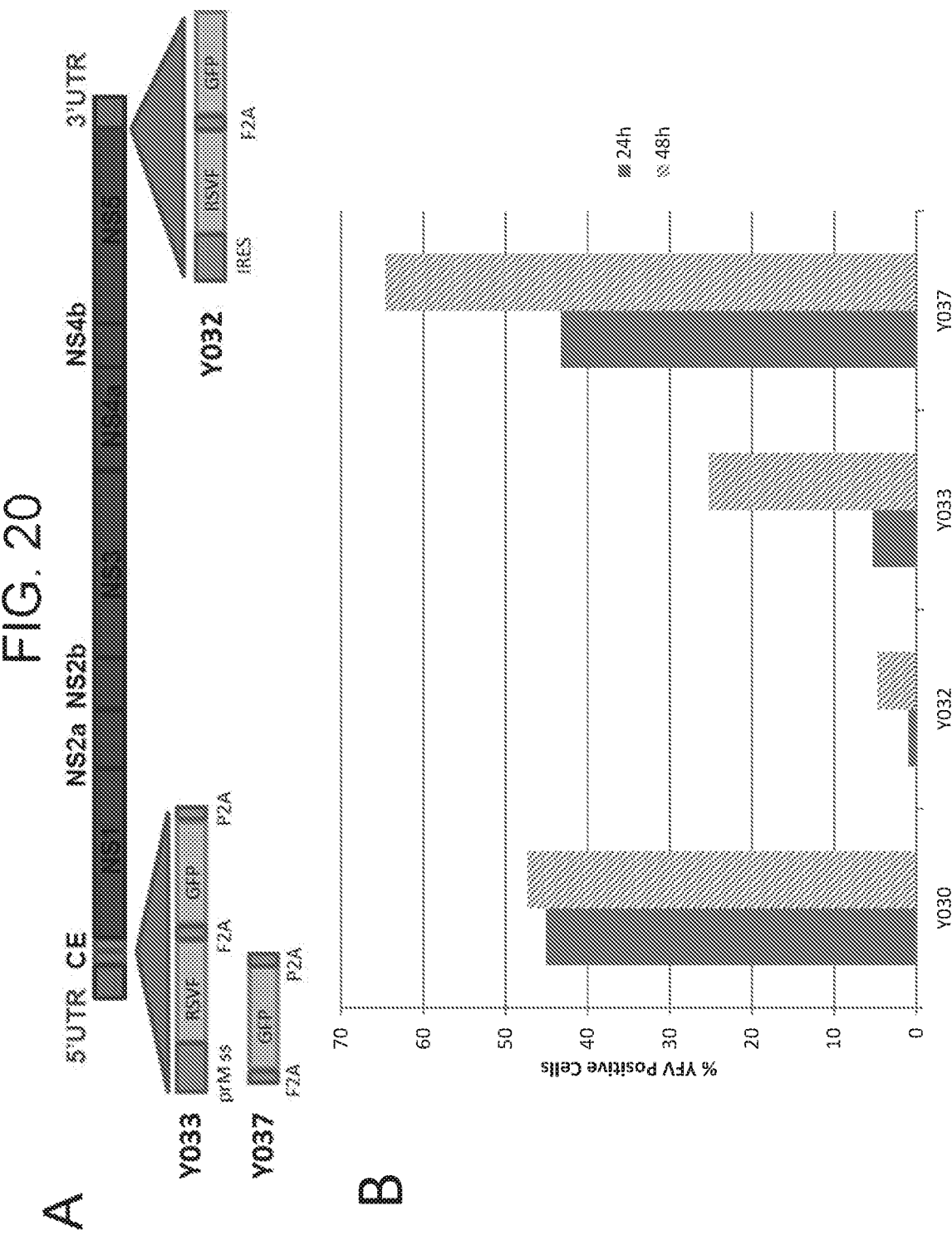
FIGS. 20A-20B provide A) schematic of YFV replicons with dual or single reporter genes and B) a bar graph summarizing testing in BHK cells.
Figure 21A:
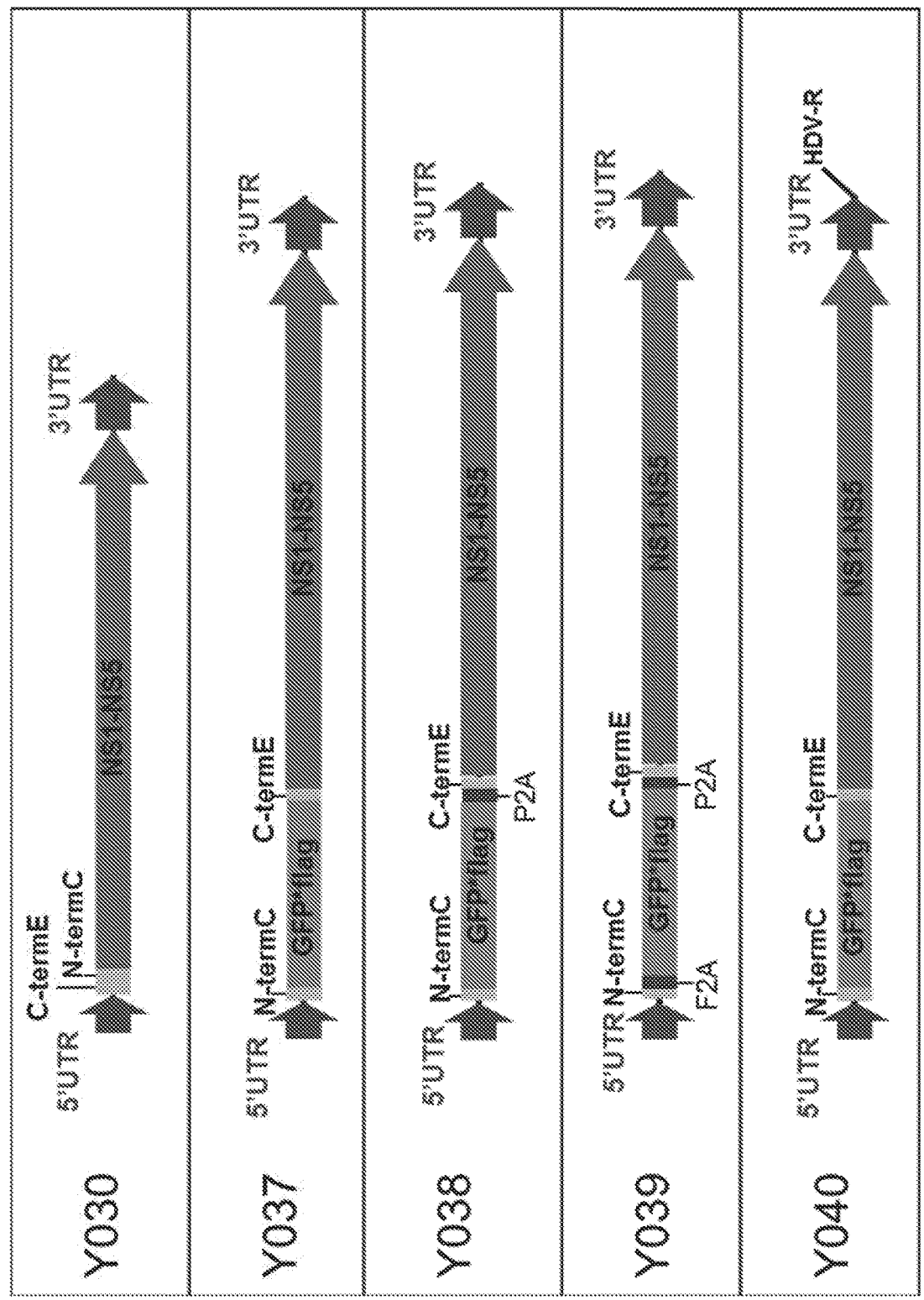
Figure 22:
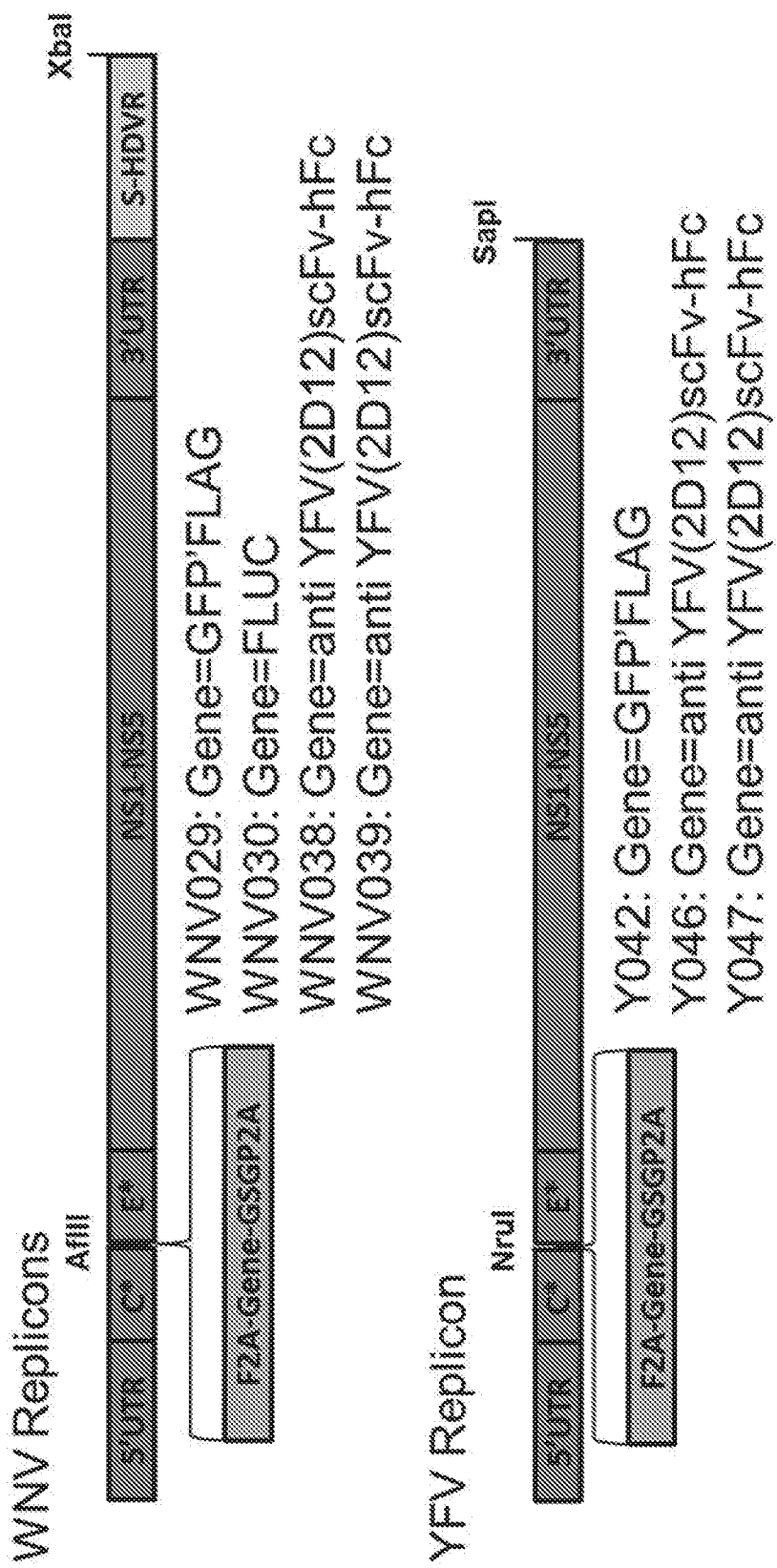
FIG. 22 provides schematics of optimized flavivirus replicons expressing GFP'FLAG, firefly luciferase (FLUC) or anti-YFV scFv-hFcs. YFV expressing FLUC was not constructed or tested at this time.
Figure 24:
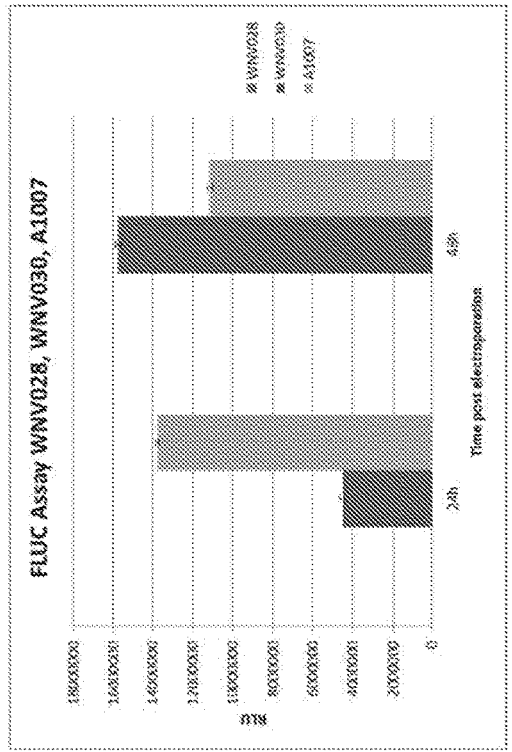
FIGS. 24A-24C demonstrate that All WNV constructs produce the reporter gene of interest.
Figure 25:
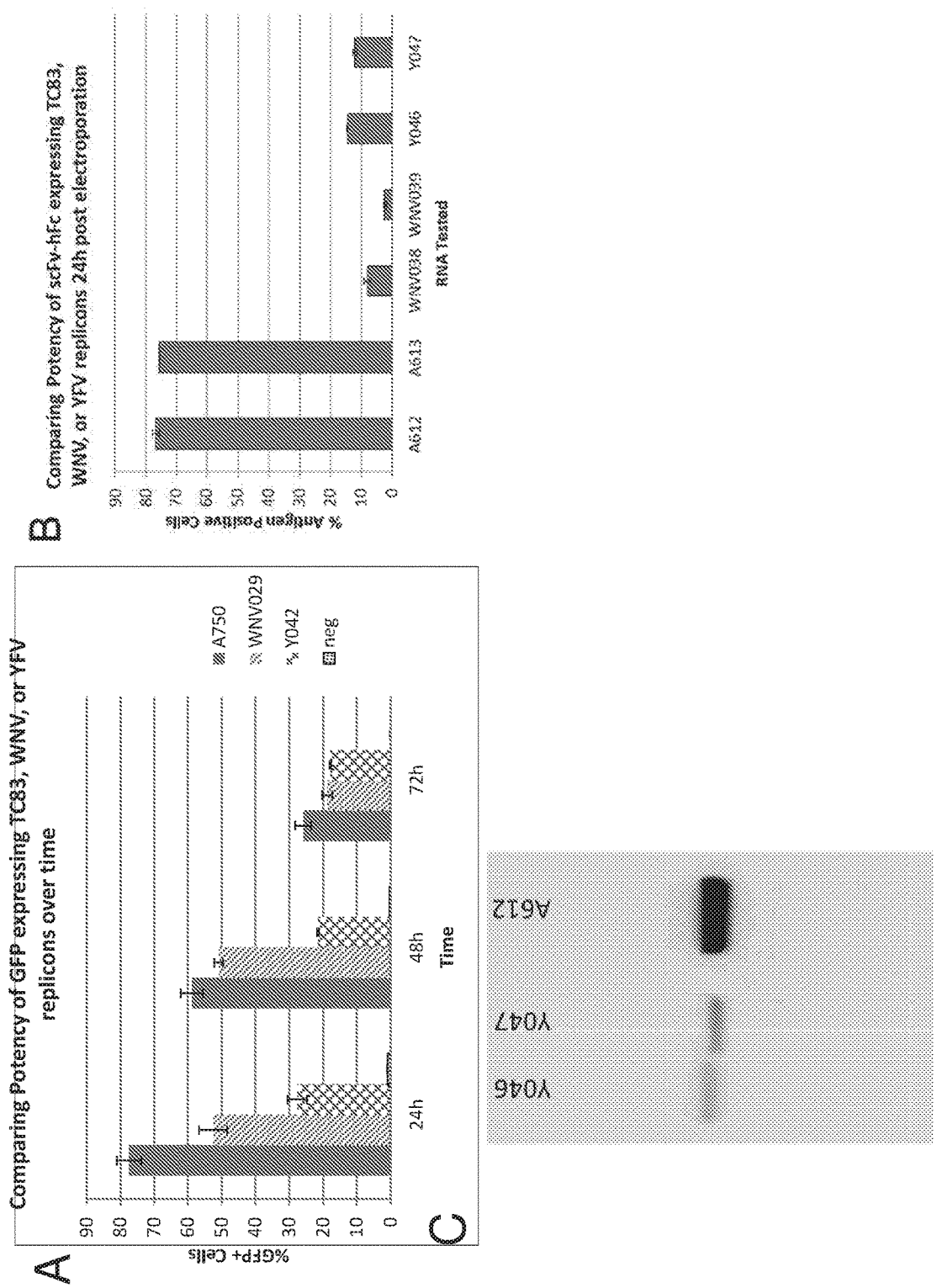
FIGS. 25A-25C summarize evaluation of YFV replicon function against TC83 and WNV.

RNA from these constructs was tested in vitro using BHK cells using a variety of methods (FIG. 19A, 19B, 19C). The most successful reporter gene setup was WNV010, containing the reporter within the deleted structural gene region with the viral pRM signal peptide followed by WNV011. The IRES driven reporter construct was essentially non-fictional with very few cells expressing GFP or WNV+ antigen. These preliminary studies indicated that WNV constructs better express heterologous genes when inserted into the structural deleted region, consistent with previous results obtained using other flavivirus replicons.

The FLFPD.RSVF-FurinF2A-GFP reporter gene was also evaluated in YFV replicons (without the 5' UTR optimization as was not yet discovered during these tests). Replicon Y032 contained the EMCV-IRES driven FLFPD.RSVF-FurinF2A-GFP reporter cassette in an upstream region of the 3' UTR. Y033 contained the reporter cassette in the structural deleted region with the viral pRM signal peptide driving processing of reporter based on results with WNV. FLAG tags were also added to the C terminus of both RSVF and GFP reporter constructs. A separate replicon, Y037 contained only a F2A-GFP'FLAG-GSGP2A reporter cassette to determine single reporter gene efficacy (FIG. 20A). RNA from each replicon was tested in vitro in BHK cells and potency was determined 24 hr and 48 hr post-electroporation. The results indicated that potency was severely reduced with the dual-reporter being inserted into the 3' UTR. The dual-reporter inserted into the structural deleted region was more effective than the IRES-3' UTR reporter, but potency was still heavily reduced. The GFP single reporter in Y037 appears to not have affected potency.

Additional mono-reporter (FIG. 21) cassettes were evaluated in YFV replicons with results indicating that flanking the transgene with F2A and GSGP2A self-cleaving peptide sequences improves replicon potency and aids in the separation of the transgene from the viral polypeptide chain.

Testing of optimized replicon reporters is further described in FIGS. 22-25.

Materials and Methods

Construction and Propagation of Flavivirus Vectors:

All WNV or YFV replicon sequences described in this study were assembled into low-copy number (p15 ori) vectors with ampicillin resistance cassettes. Vectors were constructed using a variety of molecular biology tools such as general restriction digestion and ligation, PCR, site-directed mutagenesis, and in-fusion cloning. WNV vectors were propagated via transformation of XL-10 Gold Ultra-competent cells (Agilent). YFV vectors were propagated via transformation of Stellar competent cells (Clontech). Carbenicillin (25 µg/ml) was used as a selection marker on agar Luria broth plates (Teknova) or in Luria broth media during plasmid preparation and growth.

Generation of Flavivirus Templates for In Vitro Transcription:

Plasmids holding WNV replicon sequences were used to generate templates prior to in vitro transcription using a variety of methods: (i) XbaI Linearization and exonuclease treatment—for constructs such as WNV001, plasmid WNV001 was linearized via XbaI (New England Biolabs) digestion for 2 hr at 37° C. followed by treatment with Mung Bean Nuclease (New England Biolabs) to remove non-native nucleotides from the template strand. (ii) PCR template generation—for constructs such as WNV001, plasmid WNV001 was used as a PCR template to generate a WNV replicon template without the need for digestion or exonuclease treatment. (iii) XbaI linearization—for constructs containing ribozyme sequences plasmids were linearized via XbaI digestion for 2 hr at 37° C. Plasmids holding YFV replicon sequences were used to generate templates prior to in vitro transcription using a variety of methods. (i) PmeI Linearization—for constructs containing ribozyme sequences plasmids were linearized via PmeI digestion (New England Biolabs) digestion for 2 hr at 37° C. (ii) PCR template generation—PCR was used to generate YFV replicon template without the need for digestion (iii) BspQI linearization—YFV plasmids containing a BspQI linearization site were linearized via BspQI (New England Biolabs) digestion for 2 hr at 50° C. Reaction products for all types of template generation were purified using QIAquick PCR purification kit (Qiagen)

Generation of Alphavirus Templates for In Vitro Transcription:

Plasmids containing TC83 replicon sequences, such as A750, were linearized via BspQI digestion for 2 hr at 50° C. followed by purification using QIAquick PCR purification kit.

In Vitro Transcription:

Approximately 1 µg-5 µg of prepared DNA template was added into 50 µl-100 µl of in vitro transcription mix with the following formulation: 40 mM Tris-HCl pH 8.0 (SIGMA), MgCl$_2$ (SIGMA), 6 mM ATP, 6 mM GTP, 6 mM CTP, 6 mM UTP (NEB), 10 mM dithiothreitol (SIGMA), 2 mM spermidine (SIGMA), 0.002 U/µl pyrophosphatase (NEB), 0.8 U/µl RNase inhibitor (NEB), 1 U/µl T7 RNA polymerase (NEB). The reaction was incubated for 2 hr at 30° C. RNA was capped via the addition of the following components to the final concentration indicated: 50 mM Tris-HCl pH 8.0, 5 mM KCl (SIGMA), 2.5 mM GTP, 0.1 mM S-Adenosyl methionine (NEB), 3.5 mM Dithiothreitol, 0.01 U/µl Turbo DNAse (Invitrogen), 0.95 U/µl RNAse inhibitor, 0.2 U/µl vaccinia capping system (NEB), water to increase volume of initial reaction by 4x. The capping reaction was incubated for 1 hr at 30° C. 7.5 M LiCl was added to the in vitro transcription reaction to a final concentration of 2.8 M and incubated at −20° C. for 30 min or overnight. RNA was pelleted via centrifugation. The pellet was washed once with 70% ethanol and allowed to air dry followed by resuspension in nuclease free water. For applications where uncapped RNA was required, vaccinia capping enzyme was not included as a component.

Baby Hamster Kidney or HeLa Cell Culture:

BHK cells were grown in Dulbecco's Modification of Eagle's Medium (DMEM) (Hyclone) supplemented with 5% fetal bovine serum (Omega Scientific), 100 units of penicillin and 100 µg/ml streptomycin (Invitrogen), and 2 mM L-Glutamine (Invitrogen). Cells were grown at 37° C. and 5% $CO_2$. HeLa cells were grown using a similar media formulation except supplemented with 10% FBS.

Electroporation of BHK Cells:

Baby hamster kidney (BHK) cells were collected from T225 parent flask at 80%-90% confluency by aspirating media and washing with 10 ml 1×DPBS. Approximately 10 ml trypsin (0.25%, phenol red, Life Technologies) was added to the flask and aspirated. Cells were incubated at 37° C. for 5 min and flask was agitated to assist cell detachment. To stop trypsination, 10 ml of media was added to the flask. Cells were centrifuged at ~460× g for 5 min and media was removed. Cells were resuspended in OPTI-MEM (Life Technologies) to a final concentration of $4 \times 10^6$ cells/ml. The desired amount of RNA was added to a 2 mm cuvette along with mouse thymus RNA (Hyclone) to bring total RNA to 4.2 µg, followed by 250 µl of OPTI-MEM resuspended cells ($1 \times 10^6$ cells). Electroporation was performed with a Bio-Rad Gene Pulser X-Cell using the Square Wave protocol with the following parameters: 120 V, 25 msec pulse, 0 pulse interval, 1 pulse. Electroporated cells were allowed to rest for 10 min before being transferred to a well in a 6-well plate containing 2 ml of media.

Cationic Transfection of mRNA

BHK or HeLa were seeded into a 6-well plate at 250 k/well and were grown until 80% confluency. RNA was transfected into cells using a TransIT-mRNA kit (MIRUS). The transfection protocol for one-well is as follows and can be scaled up appropriately: 250 ng of RNA was diluted in Opti-MEM to a total volume of 265 µl; 1 µl of mRNA boost reagent was immediately added and gently swirled followed by the addition of 1 µl of TransIT-mRNA reagent; the solution was gently swirled again and allowed to incubate at room temperature for 3 min; the transfection solution was diluted in complete growth medium (DMEM+5% FBS or DMEM+10% FBS for BHK or HeLa cells, respectively) to a final volume of 2.5 ml and gently mixed. Media from a well to be transfected was aspirated and replaced with transfection media. Cells were incubated for 4 hr at 37° C. 5% $CO_2$, after which the transfection media was replaced with normal growth media.

Immunohistochemistry to Detect WNV Antigen Expressing Cells:

Wells (6-well format) containing electroporated cells were washed with 1×DPBS and fixed in −20° C. acetone: methanol (1:1 v/v) for 3 min. Fixation solution was aspirated and cell layers were washed with 1×DPBS followed by the addition of PBS+2% normal goat serum (NGS, SIGMA) blocking solution for 1 hr at room temp. Following blocking, cells were incubated with 1:1000 dilution of primary antibody solution of anti-WNV mouse hyperimmune ascitic fluid (MHIAF, a gift from R.B. Tesh) in PBS+2% NGS at room temp for 1 h. Primary antibody solution was removed and cells were washed 2 times with 1×DPBS. Secondary antibody solution of 1:1000 dilution horse radish peroxidase conjugated goat anti-mouse IgM (HAL, Rockland) in PBS+2% NGS was then added and incubated at room temp for 2 h. Secondary antibody solution was removed and washed 3× with 1×PBS. To visualize cells, True Blue Peroxidase Substrate (KPL) was added to cell layer and incubated at 5 min at RT until blue color developed.

Western Blot Analyses:

Western blots were performed on cell supernatants and/or cell lysates as follows. Supernatants were collected and centrifuged to pellet debris. Debris free supernatant was stored at −20° C. until analysis. Cell lysates were collected by aspirating media and washing cell layers with 1×DPBS. Wash was removed and cells were lysed using RIPA buffer (Boston BioProducts) with pipetting to facilitate cell lysis. Lysates were centrifuged to pellet debris. Lysates were stored at −20° C. until analysis. Supernatants or lysates were diluted in 4× NuPage LDS Buffer (Life Technologies); for applications requiring reduction, 1M DTT (Life Technologies) was added to a final concentration of 62.5 mM. Samples were heated at 95° C. for 5 min followed by loading onto NuPAGE Novex 4-12% Bis-Tris Protein Gel (Life Technologies) and ran in 1×MOPS Buffer (Life Technologies) at 150V for 1 hr. Gel was transferred onto a nitrocellulose membrane using the iBlot Gel Transfer device (Invitrogen), following the manufacturer's instructions. Nitrocellulose membranes were blocked with 1×PBS+0.1% Tween+10% milk. Membranes were washed 3× with 1×PBS+0.1% Tween and stained for WNV antigen, YFV antigen, or FLAG tags depending on the application as follows. WNV antigen staining: Primary antibody solution (1:1000 dilution of anti-WNV MHIAF in 1×PBS+0.1% Tween) was added to membrane and incubated at room temp. for 2 h, washed 3× with PBS+0.1% Tween. Secondary antibody solution (1:10000 dilution Rockland HRP conjugated goat anti-mouse IgM in 1×PBS+0.1% Tween) was then added to the blot and incubated at room temp for 1 hr. Sample was washed 3× with 1×PBS+0.1% Tween and 1×PBS for 5 min. ECL Western Blotting Detection Reagent (GE Healthcare) was added to the blot, following the manufacturer's instructions. Western blot films were developed by exposure onto ECL hyperfilm (GE Healthcare) and processed using Konica Minolta SRX-101A X-Ray device. YFV antigen staining: same protocol as above except primary antibody solution (1:1000 dilution of anti-WNV MHIAF in 1×PBS+0.1% Tween) was used. FLAG-Tag antigen staining: same protocol as above except primary antibody solution (Mouse Monoclonal ANTI-FLAG M2 Antibody 1 μg/ml, clone M2, SIGMA F1804 SLBD6976 in 1×PBS-T) was used.

Luciferase Assay:

Media was removed from cells and cell layers were washed with 1×DPBS. Wash was removed and 1× Cell Culture Lysis Buffer (Promega) was added to wells followed by scraping to facilitate cell layer lysis. Debris was pelleted via centrifugation and discarded. Lysates were stored at −80° C. until analysis. To measure luciferase activity, samples were thawed and equilibriated at room temperature and 20 μl of each sample was added to a well in a 96-w flat bottom, opaque well plate (Costar). The plate was analyzed using a Centro LB960 luminometer and accompanying MikroWin2000 software using the following parameters: Inject 100 μl luciferase assay reagent (Promega); 2 sec pause; 1 sec read.

Antigenic Replicon Potency Via Flow Cytometry Analysis:

Media was removed from cells and cell layers were washed with 1×DPBS. Trypsin (0.25%) was added to cells and incubated at 37° C. until cells began to detach. Detachment was facilitated by pipetting and transferred into a 96-well round bottom plate. Cells were pelleted by centrifugation at ~462× g for 3 min. Typsin was decanted and cells were washed 1× with staining buffer (1×PBS+0.25% bovine serum albumin+0.2% NaN$_3$) and pelleted as before. Pellets were resuspended in Cytofix/Cytoperm solution (BD) and incubated at 4 C for 20 min and re-pelleted. Cells were washed 2× in Perm/Wash buffer (Perm/Wash buffer, BD, diluted to 1× in 1×PBS) with pelleting between washes. Antigens from TC83, WNV, or YFV were detected as follows per sample. TC83 antigen detection: 0.75 µl of J2 monoclonal antibody mouse, IgG2a, kappa chain (Scicons) was diluted in 0.75 µl Zenon Allophycocyanin (APC) mouse IgG2a labeling kit component A (Invitrogen) and incubated for 5 min at room temperature followed by the addition of 0.75 µl Zenon Allophycocyanin (APC) mouse IgG2a labeling kit component B and incubated for 5 min at room temp. The stain was diluted with 57.5 µl of perm/wash solution and a cell pellet was resuspended in 50 µl of the diluted solution and incubated for 30 min at 4° C. Stained cells were repelleted and washed 2× with perm/wash buffer and 2× with staining buffer. Cells were run through BD FACsCalibur E-4647 Instrument and potency was determined using FlowJo analysis software by determining the number of antigen positive cells compared to the total cell population. WNV antigen detection: same protocol as above except anti-WNV MHIAF was diluted into component A. YFV antigen detection: same protocol as above except anti-YFV MHIAF was diluted into component A.

Potency, Cytotoxicity, and Expression Analysis Using GFP Expressing Replicons

Media from cells transfected with GFP expressing replicons was harvested to collect any dead or unadhered cells along with cell layers via treatment with 0.25% trypsin. Mock transfected cells were used as a negative control and cells treated with 10 µg/µl puromycin in media were used as a positive control. Media and trypsinized cells were combined and centrifuged together at ~462xg for 3 min. Cell pellets were washed with 1×DPBS and transferred into one well in a 96-well round bottom plate. Cells were pelleted and resuspended in 1:1000 dilution of Live/Dead Fixable Far Red Dead Cell Stain (Molecular Probes) in 1×DBPS and incubated at 4° C. for 30 min. Live/Dead stained cells were pelleted and washed with twice with 1×DPBS+1% bovine serum albumin. Samples were run through the BD FACsCalibur E-4647 Instrument and FlowJo analysis software was used to analyze the data. Cytotoxicity was determined by gating for GFP positive cells indicating the presence of the replicon followed by determining percentage of dead cells within the GFP positive population. Potency was determined by gating for live cells and the percentage of GFP positive cells within the live population. GFP expression was determined by analyzing the mean fluorescence intensity (MFI) of live, GFP expressing cells.

It should be understood that for all numerical bounds describing some parameter in this application, such as "about," "at least," "less than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that they are incorporated by reference in their entirety for all purposes as well as for the proposition that is recited. Where any conflict exists between a document incorporated by reference and the present application, this application will control. All information associated with reference gene sequences disclosed in this application, such as GeneIDs or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures), as well as chemical references (e.g., PubChem compound, PubChem substance, or PubChem Bioassay entries, including the annotations therein, such as structures and assays, et cetera), are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art—thus, to the extent an element is described in one or more references known to the person having ordinary skill in the art, they may be excluded from the claimed invention by, inter alia, a negative proviso or disclaimer of the feature or combination of features.

---

SEQUENCE LISTING

WNV Replicon Nucleotide Sequence (UTRs included);
SEQ ID NO: 1:
agtagttcgcctgtgtgagctgacaaacttagta
gtgtttgtgaggattaacaacaattaacacagtg
cgagctgtttcttagcacgaagatctcgatgtct
aagaaaccaggagggcccggcaagagccgggctg
tcaatatgctaaaacgcggaatgccccgcgtgtt
gtccttgattggacttaagatgggcatcaatgct

SEQUENCE LISTING

```
cgtgataggtccatagctctcacgtttctcgcag
ttggaggagttctgctcttcctctccgtgaacgt
gcacgctgacactgggtgtgccatagacatcagc
cggcaagagctgagatgtggaagtggagtgttca
tacacaatgatgtgaaggcttggatggaccgata
caagtattaccctgaaacgccacaaggcctagcc
aagatcattcagaaagctcataaggaaggagtgt
gcggtctacgatcagtttccagactggagcatca
aatgtgggaagcagtcaaggacgagctgaacact
cttttgaaggagaatggtgtggaccttagtgtcg
tggttgagaaacaggagggaatgtacaagtcagc
acctaaacgcctcaccgccaccacggaaaaattg
gaaattggctggaaggcctggggaaagagtattt
tatttgcaccagaactcgccaacaacacctttgt
ggttgatggtccggagaccaaggaatgtccgact
cagaatcgcgcttggaatagcttagaagtggagg
attttggatttggtctccaccagcactcggatgtt
cctgaaggtcagagagagcaacacaactgaatgt
gactcgaagatcattggaacggctgtcaagaaca
acttggcgatccacagtgacctgtcctattggat
tgaaagcaggctcaatgatacgtggaagcttgaa
agggcagttctgggtgaagtcaaatcatgtacgt
ggcctgagacgcataccttgtggggcgatggaat
cctgagacggacttgataataccagtcacactg
gcggaccacgaagcaatcacaatcggagacctg
ggtacaagacacaaaaccagggccatgggacga
aggccgggtagagattgacttcgattactgccca
ggaactacggtcaccctgagtgagagctgcgac
accgtggacctgccactcgcaccaccacagagag
cggaaagttgataacagattggtgctgcaggagc
tgcaccttaccaccactgcgctaccaaactgaca
gcggctgttggtatggtatggagatcagaccaca
gagacatgatgaaaagaccctcgtgcagtcacaa
gtgaatgcttataatgctgatatgattgacccctt
ttcagttgggccttctggtcgtgttcttggccac
ccaggaggtccttcgcaagaggtggacagccaag
atcagcatgccagctatactgattgctctgctag
tcctggtgtttgggggcattacttacactgatgt
gttacgctatgtcatcttggtggggggcagctttc
gcagaatctaattcgggaggagacgtggtacact
tggcgctcatggcgaccttcaagatacaaccagt
gtttatggtggcatcgtttctcaaagcgagatgg
accaaccaggagaacatttgttgatgttggcgg
ctgttttctttcaaatggcttatcacgatgcccg
ccaaattctgctctgggagatccctgatgtgttg
aattcactggcggtagcttggatgatactgagag
ccataacattcacaacgacatcaaacgtggttgt
tccgctgctagccctgctaacacccgggctgaga
tgcttgaatctggatgtgtacaggatactgctgt
tgatggtcggaataggcagcttgatcaggagaa
gaggagtgcagctgcaaaaaagaaaggagcaagt
ctgctatgcttggctctagcctcaacaggacttt
tcaaccccatgatccttgctgctgctgattac
atgtgatcccaaccgtaaacgcggatggcccgca
actgaagtgatgacagctgtcggcctgatgtttg
ccatcgtcggagggctggcagagcttgacattga
ctccatggccattccaatgactatcgcggggctc
atgtttgctgctttcgtgatttctgggaaatcaa
cagatatgtggattgagagaacggcggacatttc
ctgggaaagtgatgcagaaattacaggctcgagc
gaaagagttgatgtgcggcttgatgatgatggaa
acttccagctcatgaatgacaccgaccaccttg
gaagatatggatgctcagaatggtctgtctcgcg
attagtgcgtacaccccctgggcaatcttgccct
cagtagttggattttggataactctccaatacac
aaagagaggaggcgtgttgtgggacactccctca
ccaaaggagtacaaaaggggggacacgaccaccg
gcgtctacaggatcatgactcgtgggctgctcgg
cagttatcaagcaggagcgggcgtgatggttgaa
ggtgttttccacaccctttggcatacaacaaaag
gagccgctttgatgagcggagagggccgcctgga
cccatactgggtcagtgtcaaggatactgacttc
tgttacggaggaccctggaaattgcagcacaagt
ggaacgggcaggatgaggtgcagatgattgtggt
ggaacctggcaagaacgttaagaacgtccagacg
aaaccaggggtgttcaaaacacctgaaggagaaa
tcggggccgtgactttggacttccccactggaac
```

```
atcaggctcaccaatagtggacaaaaacggtgat
gtgattgggctttatggcaatggagtcataatgc
ccaacgctcatacataagcgcgatagtgcaggg
tgaaaggatggatgagccaatcccagccggattc
gaacctgagatgctgaggaaaaaacagatcactg
tactggatctccatcccggcgccggtaaaacaag
gaggattctgccacagatcatcaaagaggccata
aacagaagactgagaacagccgtgctagcaccaa
ccagggttgtggctgctgagatggctgaagcact
gagaggactgcccatccggtaccagacatccgca
gtgcccagagaacataatggaaatgagattgttg
atgtcatgtgtcatgctaccctcacccacaggct
gatgtctcctcacagggtgccgaactacaacctg
ttcgtgatggatgaggctcatttcaccgacccag
ctagcattgcagcaagaggttacatttccacaaa
ggtcgagctaggggaggcggcggcaatattcatg
acagccacccaccaggcacttcagatccattcc
cagagtccaattcaccaatttccgacttacagac
tgagatcccggatcgagcttgaactctggatac
gaatggatcacagaatacaccgggaagacggttt
ggtttgtgcctagtgtcaagatggggaatgagat
tgccctttgcctacaacgtgctgaaagaaagta
gtccaattgaacagaaagtcgtacgagacggagt
acccaaaatgtcagaactgattgggacttttgt
tatcacaacagacatatctgaaatgggggctaac
tttaaggcgagcagggtgattgacagccggaaga
gtgtgaaaccaaccatcataacagaaggagaagg
gagagtgatcctgggagaaccatctctgcagtgaca
gcagctagtgccgcccagaacgatggacgtatcg
gtagaaatccgtcgcaagttggtgatgagtactg
ttatggggggcacacgaatgaagacgactcgaac
ttcgcccattggactgaggcacgaatcatgctgg
acaacatcaacatgctgaaacggactgatcgctca
attctaccaaccagagcgtgagaaggtatatacc
atggatggggaataccggctcagaggagaagaga
gaaaaaactttctggaactgttgaggactgcaga
tctgccagtttggctggcttacaaggttgcagcg
gctgagtgtcataccacgaccggaggtggtgct
ttgatggtcctaggacaaacacaattttagaaga
caacaacgaagtggaagtcatcacgaagcttggt
gaaaggaagattctgaagacaccgcgctggattgacg
ccagggtgtactcggatcaccaggcactaaaggc
gttcaaggacttcgcctcgggaaaacgttctcag
atagggctcattgaggttctgggaaagatgcctg
agcacttcatggggaagacatgggaagcacttga
caccatgtacgttggccactgcagagaaagga
ggaagagctcacagaatggccctggaggaactgc
cagatgctcttcagacaattgccttgattgcctt
attgagtgtgatgaccatgggagtattcttcctc
ctcatgcagcggaagggcattggaaagataggtt
tgggaggcgctgtcttgggagtcgcgaccttttt
ctgttggatggctgaagttccaggaacgaagatc
gccggaatgttgctgctctcccttctcttgatga
ttgtgctaattcctgagccagagaagcaacgttc
gcagacagacaaccagctagccgtgttcctgatt
tgtgtcatgacccttgtgagcgcagtggcagcca
acgagatgggttggctagataagaccaagagtga
cataagcagtttgtttgggcaaagaaattgaggtc
aaggagaatttcagcatgggagagtttcttctgg
acttgaggccggcaacagcctggtcactgtacgc
tgtgacaacagcggtcctcactccactgctaaag
catttgatcacgtcagattacatcaacacctcat
tgacctcaataaacgttcaggcaagtgcactatt
cacactcgcgcgaggcttccccttcgtcgatgtt
ggagtgtcggctctcctgctagcagccggatgct
ggggacaagtcaccctcaccgttacggtaacagc
ggcaacactccttttttgccactatgcctacatg
gttcccggttggcaagctgaggcaatgcgctcag
cccagcggcggacagcggccggaatcatgaagaa
cgctgtagtggatggcatcgtggccacggacgtc
ccagaattagagcgcaccacacccatcatgcaga
agaaagttggacatcatgctgatcttggtgtc
tctagctgcagtagtagtgaacccgtctgtgaag
acagtacgagaagccggaattttgatcacggccg
cagcggtgacgctttgggagaatggagcaagctc
tgtttggaacgcaacaactgccatcggactctgc
cacatcatgcgtgggggttggttgtcatgtctat
```

SEQUENCE LISTING

```
ccataacatggacactcataaagaacatggaaaa
accaggactaaaaagagggtggggcaaaaggacgc
acctttgggagaggtttggaaagaaagactcaacc
agatgacaaaagaagagttcactaggtaccgcaa
agaggccatcatcgaagtcgatcgctcagcagca
aaacacgccaggaaagaaggcaatgtcactggag
ggcatccagtctctaggggcacagcaaaactgag
atggctggtcgaacggaggtttctcgaaccggtc
ggaaaagtgattgaccttggatgtggaagaggcg
gttggtgttactatatggcaacccaaaaagagt
ccaagaagtcagagggtacacaaagggcggtccc
ggacatgaagagccccaactagtgcaaagttatg
gatgaacattgtcaccatgaagagtggggtgga
tgtgttctacagaccttctgagtgttgtgacacc
ctcctttgtgacatcggagagtcctcgtcaagtg
ctgaggttgaagagcataggacgattcgggtcct
tgaaatggttgaggactggctgcaccgagggcca
agggaattttgcgtgaaggtgctctgcccctaca
tgccaaagtcatagagaagatggagctgctcca
acgccggtatgggggggactggtcagaaaccca
ctctcacggaattccacgcacgagatgtattggg
tgagtcgagcttcaggcaatgtggtacattcagt
gaatatgaccagccaggtgctcctaggaagaatg
gaaaaaggacctgaagggaccccaatacgagg
aagatgtaaacttgggaagtggaaccagggcggt
gggaaaaccctgctcaactcagacaccagtaaa
atcaagaacaggattgaacgactcaggcgtgagt
acagttcgacggtggcaccacgatgagaaccaccc
atatagaacctggaactatcacggcagttatgat
gtgaagcccacaggctccgccagttcgctggtca
atggagtggtcaggctcctctcaaaaccatggga
caccatcacgaagtgttaccaccatggccatgact
gacactactccctttcgggcagcagcgagtgttca
aagagaaggtggacacgaaagctcctgaaccgcc
agaaggagtgaagtacgtgctcaacgagaccacc
aactggttgtgggcgttttttggccagagaaaac
gtcccagaatgtgctctcgagaggaattcataag
aaaggtcaacgacaatgcagctttggtgccatg
tttgaagagcagaatcaatggaggagcgccagag
aggcagttgaagatccaaaattttgggagatggt
ggatgaggagcgcgaggcacatctgcgggagaa
tgtcacacttgtcatttacaacatgatgggaaga
gagagaaaaacccggagagttcggaaaggccaa
gggaagcagagccatttggttcatgtggctcgga
gctcgctttctggagttcgaggctctgggttttc
tcaatgaagaccactggttcgtggaagaaagaactc
aggaggaggtgtcgagggcttgggcctccaaaa
ctgggtt

SEQUENCE LISTING

VKTVREAGILITAAAVTLWENGASSVWNATTAIG
LCHIMRGGWLSCLSITWTLIKNMEKPGLKRGGAK
GRTLGEVWKERLNQMTKEEFTRYRKEAIIEVDRS
AAKHARKEGNVTGGHPVSRGTAKLRWLVERRFLE
PVGKVIDLGCGRGGWCYYMATQKRVQEVRGYTKG
GPGHEEPQLVQSYGWNIVTMKSGVDVFYRPSECC
DTLLCDIGESSSSAEVEEHRTIRVLEMVEDWLHR
GPREFCVKVLCPYMPKVIEKMELLQRRYGGGLVR
NPLSRNSTHEMYWVSRASGNVVHSVNMTSQVLLG
RMEKRTWKGPQYEEDVNLGSGTRAVGKPLLNSDT
SKIKNRIERLRREYSSTWHHDENHPYRTWNYHGS
YDVKPTGSASSLVNGVVRLLSKPWDTITNVTTMA
MTDTTPFGQQRVFKEKVDTKAPEPPEGVKYVLNE
TTNWLWAFLAREKRPRMCSREEFIRKVNSNAALG
AMFEEQNQWRSAREAVEDPKFWEMVDEEREAHLR
GECHTCIYNMMGKREKKPGEFGKAKGSRAIWFMW
LGARFLEFEALGFLNEDHWLGRKNSGGGVEGLGL
QKLGYILREVGTRPGGKIYADDTAGWDTRITRAD
LENEAKVLELLDGEHRRLARAIIELTYRHKVVKV
MRPAADGRTVMDVISREDQRGSGQVVTYALNTFT
NLAVQLVRMMEGEGVIGPDDVEKLTKGKGPKVRT
WLFENGEERLSRMAVSGDDCVVKPLDDRFATSLH
FLNAMSKVRKDIQEWKPSTGWYDWQQVPFCSNHF
TELIMKDGRTLVVPCRGQDELVGRARISPGAGWN
VRDTACLAKSYAQMWLLLYEHRRDLRLMANAICS
AVPVNWVPTGRTTWSIHAGGEWMTTEDMLEVWNR
VWIEENEWMEDKTPVEKWSDVPYSGKREDIWCGS
LIGTRARATWAENIQVAINQVRAIIGDEKYVDYM
SSLKRYEDTTLVEDTVL

YFV Replicon Nucleotide Sequence (UTRs included);
SEQ ID NO: 3:
agtaaatcctgtgtgctaattgaggtgcattggt
ctgcaaatcgagttgctaggcaataaacacattt
ggattaattttaatcgttcgttgagcgattagca
gagaactgaccagaacatgtctggtcgtaaagct
cagggaaaaaccctgggcgtcaatatggtacgac
gaggagttcgctccttgtcaaactcgcgaaacat
gacaatgtccatgagcatgatcttggtaggagtg
atcatgatgtttttgtctctaggagttggggcgg
atcaaggatgcgccatcaactttggcaagagaga
gctcaagtgcggagatggtatcttcatatttaga
gactctgatgactggctgaacaagtactcatact
atccagaagatcctgtgaagcttgcatcaatagt
gaaagcctcttttgaagaagggaagtgtggccta
aattcagttgactcccttgagcatgagatgtgga
gaagcagggcagatgagatcaatgccatttttga
ggaaaacgaggtggacatttctgttgtcgtgcag
gatccaaagaatgtttaccagagaggaactcatc
cattttccagaattcgggatggtctgcagtatgg
ttggaagacttggggtaagaaccttgtgttctcc
ccagggaggaagaatggaagcttcatcatagatg
gaaagtccaggaaagaatgcccgttttcaaaccg
ggtctggaattctttccagatagaggagtttggg
acgggagtgttcaccacacgcgtgtacatggacg
cagtctttgaatacaccatagactgcgatggatc
tatcttgggtgcagcggtgaacggaaaaaagagt
gcccatggctctccaacattttggatgggaagtc
atgaagtaaatgggacatggatgatccacacctt
ggaggcattagattacaaggagtgtgagtggcca
ctgacacatacgattggaacatcagttgaagaga
gtgaaatgttcatgccgagatcaatcggaggccc
agttagctctcacaatcatatccctggatacaag
gttcagacgaacggaccttggatgcaggtaccac
tagaagtgaagagagaagcttgcccagggactag
cgtgatcattgatggcaactgtgatggacgggga
aaatcaaccagatccaccacggatagcgggaaag
ttattcctgaatggtgttgccgctcctgcacaat
gccgcctgtgagcttccatggtagtgatgggtgt
tggtatcccatggaaattaggccaaggaaaacgc
atgaaagccatctggtgcgctcctgggttacagc
tggagaaatacatgctgtcccttttggtttggtg
agcatgatgatagcaatggaagtggtcctaagga
aaagacagggaccaaagcaaatgttggttggagg
agtagtgctcttgggagcaatgctggtcgggcaa
gtaactctccttgatttgctgaaactcacagtgg
ctgtgggattgcatttccatgagatgaacaatgg

SEQUENCE LISTING aggagacgccatgtatatggcgttgattgctgcc
ttttcaatcagaccagggctgctcatcggctttg
ggctcaggaccctatggagccctcgggaacgcct
tgtgctgaccctaggagcagccatggtggagatt
gccttgggtggcgtgatgggcggcctgtggaagt
atctaaatgcagtttctctctgcatcctgacaat
aaatgctgttgcttctaggaaagcatcaaatacc
atcttgcccctcatggctctgttgacacctgtca
ctatggctgaggtgagacttgccgcaatgttctt
ttgtgccgtggttatcataggggtccttcaccag
aatttcaaggacacctccatgcagaagactatac
ctctggtggccctcacactcacatcttacctggg
cttgacacaaccttttttgggcctgtgtgcattt
ctggcaacccgcatatttgggcgaaggagtatcc
cagtgaatgaggcactcgcagcagctggtctagt
gggagtgctggcaggactggcttttcaggagatg
gagaacttccttggtccgattgcagttggaggac
tcctgatgatgctggttagcgtggctgggagggt
ggatgggctagagctcaagaagcttggtgaagtt
tcatgggaagaggaggcggagatcagcgggagtt
ccgcccgctatgatgtggcactcagtgaacaagg
ggagttcaagctgctttctgaagagaaagtgcca
tgggaccaggttgtgatgacctcgctggccttgg
ttggggctgccctccatccatttgcacttctgct
ggtccttgctgggtggctgtttcatgtcagggga
gctaggagaagtggggatgtcttgtgggatattc
ccactcctaagatcatcgaggaatgtgaacatct
ggaggatgggatttatggcatattccagtcaacc
ttcttgggggcctcccagcgaggagtgggagtgg
cacagggaggggtgttccacacaatgtggcatgt
cacaagaggagctttccttgtcaggaatggcaag
aagttgattccatcttgggcttcagtaaaggaag
accttgtcgcctatggtggctcatggaagttgga
aggcagatgggatggagaggaagaggtccagttg
atcgcggctgttccaggaaagaacgtggtcaacg
tccagacaaaaccgagcttgttcaaagtgaggaa
tgggggagaaatcggggctgtcgctcttgactat
ccgagtggcacttcaggatctcctattgttaaca
ggaacggagaggtgattgggctgtacggcaatgg
catccttgtcggtgacaactccttcgtgtccgcc
atatcccagactgaggtgaaggaagaaggaaagg
aggagctccaagagatcccgacaatgctaaagaa
aggaatgacaactgtccttgattttcatcctgga
gctgggaagacaagacgtttcctcccacagatct
tggccgagtgcgcacggagacgcttgcgcactct
tgtgttggcccccaccagggttgttctttctgaa
atgaaggaggcttttcacggcctggacgtgaaat
tccacacacaggctttttccgctcacggcagcgg
gagagaagtcattgatgccatgtgccatgccacc
ctaacttacaggatgttggaaccaactagggttg
ttaactgggaagtgatcattatggatgaagccca
tttttggatccagctagcatagccgctagaggt
tgggcagcgcacagagctagggcaaatgaaagtg
caacaatcttgatgacagccacaccgcctgggac
tagtgatgaatttccacattcaaatggtgaaata
gaagatgttcaaacggacatacccagtgagccct
ggaacacagggcatgactggatcctagctgacaa
aaggcccacggcatggttccttccatccatcaga
gctgcaaatgtcatggctgcctctttgcgtaagg
ctggaaagagtgtggtggtcctgaacaggaaaac
ctttgagagagaatacccccacgataaagcagaag
aaacctgactttatattggccactgacatagctg
aaatgggagccaacctttgcgtggagcgagtgct
ggattgcaggacggcttttaagcctgtgcttgtg
gatgaagggaggaaggtggcaataaaagggccac
ttcgtatctccgcatcctctgctgctcaaaggag
gggcgcattgggagaaatcccaacagagatgga
gactcatactactattctgagcctacaagtgaaa
ataatgcccaccacgtctgctggttggaggcctc
aatgctcttggacaacatggaggtgaggggtgga
atggtcgccccactctatggcgttgaaggaacta
aaacaccagtttcccctggtgaaatgagactgag
ggatgaccagaggaaagtcttcagagaactagtg
aggaattgtgacctgcccgtttggctttcgtggc
aagtggccaaggctggtttgaagacgaatgatcg
taagtggtgttttgaaggccctgaggaacatgag
atcttgaatgacagcggtgaaacagtgaagtgca

SEQUENCE LISTING

```
gggctcctggaggagcaaagaagcctctgcgccc
aaggtggtgtgatgaaagggtgtcatctgaccag
agtgcgctgtctgaatttattaagtttgctgaag
gtaggagggggagctgctgaagtgctagttgtgct
gagtgaactccctgattcctggctaaaaaaggt
ggagaggcaatggataccatcagtgtgtttctcc
actctgaggaaggctctagggcttaccgcaatgc
actatcaatgatgcctgaggcaatgacaatagtc
atgctgtttatactggctggactactgacatcgg
gaatggtcatctttttcatgtctcccaaaggcat
cagtagaatgtctatgcgatgggcacaatggcc
ggctgtggatatctcatgttccttggaggcgtca
aacccactcacatcctctatatcatgctcatatt
ctttgtcctgatggtggttgtgatccccgagcca
gggcaacaaaggtccatccaagacaaccaagtgg
catacctcattattggcatcctgacgctggtttc
agcggtggcagccaacgagctaggcat

SEQUENCE LISTING

```
IGVLHQNFKDTSMQKTIPLVALTLTSYLGLTQPF
LGLCAFLATRIFGRRSIPVNEALAAAGLVGVLAG
LAFQEMENFLGPIAVGGLLMMLVSVAGRVDGLEL
KKLGEVSWEEEAEISGSSARYDVALSEQGEFKLL
SEEKVPWDQVVMTSLALVGAALHPFALLLVLAGW
LFHVRGARRSGDVLWDIPTPKIIEECEHLEDGIY
GIFQSTFLGASQRGVGVAQGGVFHTMWHVTRGAF
LVRNGKKLIPSWASVKEDLVAYGGSWKLEGRWDG
EEEVQLIAAVPGKNVVNVQTKPSLFKVRNGGEIG
AVALDYPSGTSGSPIVNRNGEVIGLYGNGILVGD
NSFVSAISQTEVKEEGKEELQEIPTMLKKGMTTV
LDFHPGAGKTRRELPQILAECARRRLRTLVLAPT
RVVLSEMKEAFHGLDVKFHTQAFSAHGSGREVID
AMCHATLTYRMLEPTRVVNWEVIIMDEAHFLDPA
SIAARGWAAHRARANESATILMTATPPGTSDEFP
HSNGEIEDVQTDIPSEPWNTGHDWILADKRPTAW
FLPSIRAANVMAASLRKAGKSVVVLNRKTFEREY
PTIKQKKPDFILATDIAEMGANLCVERVLDCRTA
FKPVLVDEGRKVAIKGPLRISASSAAQRRGRIGR
NPNRDGDSYYYSEPTSENNAHHVCWLEASMLLDN
MEVRGGMVAPLYGVEGTKTPVSPGEMRLRDDQRK
VFRELVRNCDLPVWLSWQVAKAGLKTNDRKWCFE
GPEEHEILNDSGETVKCRAPGGAKKPLRPRWCDE
RVSSDQSALSEFIKFAEGRRGAAEVLVVLSELPD
FLAKKGGEAMDTISVFLHSEEGSRAYRNALSMMP
EAMTIVMLFILAGLLTSGMVIFFMSPKGISRMSM
AMGTMAGCGYLMFLGGVKPTHISYIMLIFFVLMV
VVIPEPGQQRSIQDNQVAYLIIGILTLVSAVAAN
ELGMLEKTKEDLFGKKNLIPSSASPWSWPDLDLK
PGAAWTVYVGIVTMLSPMLHHWIKVEYGNLSLSG
IAQSASVLSFMDKGIPFMKMNISVIMLLVSGWNS
ITVMPLLCGIGCAMLHWSLILPGIKAQQSKLAQR
RVFHGVAKNPVVDGNPTVDIEEAPEMPALYEKKL
ALYLLLALSLASVAMCRTPFSLAEGIVLASAALG
PLIEGNTSLLWNGPMAVSMTGVMRGNHYAFVGVM
YNLWKMKTGRRGSANGKTLGEVWKRELNLLDKRQ
FELYKRTDIVEVDRDTARRHLAEGKVDTGVAVSR
GTAKLRWEHERGYVKLEGRVIDLGCGRGGWCYYA
AAQKEVSGVKGFTLGRDGHEKPMNVQSLGWNIIT
FKDKTDIHRLEPVKCDTLLCDIGESSSSSVTEGE
RTVRVLDTVEKWLACGVDNFCVKVLAPYMPDVLE
KLELLQRRFGGTVIRNPLSRNSTHEMYYVSGARS
NVTFTVNQTSRLLMRRMRRPTGKVTLEADVILPI
GTRSVETDKGPLDKEAIEERVERIKSEYMTSWFY
DNDNPYRTWHYCGSYVTKTSGSAASMVNGVIKIL

TYPWDRIEEVTRMAMTDTTPFGQQRVFKEKVDTR
AKDPPAGTRKIMKVVNRWLFRHLAREKNPRLCTK
EEFIAKVRSHAAIGAYLEEQEQWKTANEAVQDPK
FWELVDEERKLHQQGRCRTCVYNMMGKREKKLSE
FGKAKGSRAIWYMWLGARYLEFEALGFLNEDHWA
SRENSGGGVEGIGLQYLGYVIRDLAAMDGGGFYA
DDTAGWDTRITEADLDDEQEILNYMSPHHKKLAQ
AVMEMTYKNKVVKVLRPAPGGKAYMDVISRRDQR
GSGQVVTYALNTITNLKVQLIRMAEAEMVIHHQH
VQDCDESVLTRLEAWLTEHGCNRLKRMAVSGDDC
VVRPIDDRFGLALSHLNAMSKVRKDISEWQPSKG
WNDWENVPFCSHHFHELQLKDGRRIVVPCREQDE
LIGRGRVSPGNGWMIKETACLSKAYANMWSLMYF
HKRDMRLLSLAVSSAVPTSWVPQGRTTWSIHGKG
EWMTTEDMLEVWNRVWITNNPHMQDKTMVKKWRD
VPYLTKRQDKLCGSLIGMTNRATWASHIHLVIHR
IRTLIGQEKYTDYLTVMDRYSVDADLQLGELI
```

TABLE 1

Exemplary 2A peptide sequences:

| Name | Amino Acid Sequence |
|---|---|
| P2A (with GSG Linker) | --------GSG---ATNFSLLKQAGDVEENPGP (SEQ ID NO: 5) |
| F2A (Long length) | FARHKQKIVAPVKQTLNFDLLKLAGDVESNPGP (SEQ ID NO: 6) |
| F2A (Intermediate length with GSG Linker) | --------GSGVKQTLNFDLLKLAGDVESNPGP (SEQ ID NO: 7) |
| E2A (with GSG Linker) | -------GSG---QCTNYALLKLAGDVESNPGP (SEQ ID NO: 8) |
| T2A (with GSG Linker) | -------GSG-----EGRGSLLTCGDVEENPGP (SEQ ID NO: 9) |

TABLE 2

Exemplary IRES elements:

| Name | Nucleotide sequence |
|---|---|
| EMCV (p) | cccccccctaacgttactggccgaagccgcttggaataaggccggtgtgcgt ttgtctatatgttattttccaccatattgccgtcttttggcaatgtgagggc ccggaaacctggccctgtcttcttgacgagcattcctaggggtctttccct ctcgccaaaggaatgcaaggtctgttgaatgtcgtgaaggaagcagttcctc tggaagcttcttgaagacaaacaacgtctgtagcgacccctttgcaggcagcg gaaccccccacctggcgacaggtgcctctgcggccaaaaagccacgtgtataa gatacacctgcaaaggcggcacaacccagtgccacgttgtgagttggatag ttgtggaaagagtcaaatggctctcctcaagcgtattcaacaaggggctgaa ggatgcccagaaggtacccccattgtatgggatctgatctggggcctcggtgc acatgctttacatgtgtttagtcgaggttaaaaaacgtctaggccccccgaa ccacgggacgtggttttccttttgaaaaacacgatgataatatggccacaac catg (SEQ ID NO: 10) |
| EMCV (7423) | Ttaaaacagctgtgggttgttcccacccacagggcccactgggcgctagcac tctgattttacgaaatccttgtgcgcctgttttatatcccttccctaattcg aaacgtagaagcaatgcgcaccactgatcaatagtaggcgtaacgcgccagt tacgtcatgatcaagcatatctgttccccggactgagtatcaatagactgc ttacgcggttgaaggagaaaacgttcgttatccggctaactacttcgagaag cccagtaacaccatggaagctgcagggtgtttcgctcagcacttcccccgtg tagatcaggtcgatgagccactgcaatcccacaggtgactgtggcagtggc tgcgttggcggcctgcctatggggagacccataggacgctctaatgtggaca tggtgcgaagagcctattgagctagttagtagtcctccggcccctgaatgcg gctaatcctaactgcggagcacatgccttcaacccagagggtagtgtgtcgt |

TABLE 2-continued

Exemplary IRES elements:

| Name | Nucleotide sequence |
|---|---|
| | aatgggcaactctgcagcggaaccgactactttgggtgtccgtgtttcttt<br>tattcttatattggctgcttatggtgacaattacagaattgttaccatatag<br>ctattggattggccatccggtgtgtaatagagctgttatatacctatttgtt<br>ggctttgtaccactaactttaaaatctataactaccctcaactttatattaa<br>ccctcaatacagttgaac<br>(SEQ ID NO: 11) |
| HCV (L) | gccagcccccgattgggggcgacactccaccatagatcactcccctgtgagg<br>aactactgtcttcacgcagaaagcgtctagccatggcgttagtatgagtgtc<br>gtgcagcctccaggccccccctcccggggagagccatagtggtctgcggaac<br>cggtgagtacaccggaattgccaggacgaccgggtcctttcttggatcaatc<br>ccgctcaatgcctggagatttgggcgtgcccccgcgagactgctagccgagt<br>agtgttgggtcgcgaaaggccttgtggtactgcctgatagggtgcttgcgag<br>tgccccgggaggtctcgtagaccgtgcaccatgagcacgaatcctaaa<br>(SEQ ID NO: 12) |
| CrPV | ctaaaaagcaaaaatgtgatcttgcttgtaaatacaatttgagaggttaat<br>aaattacaagtagtgctatttttgtatttaggttagctatttagctttacgt<br>tccaggatgcctagtggcagcccccacaatatccaggaagccctctctgcggt<br>ttttcagattaggtagtcgaaaaacctaagaaatttacctgctacatttcaa<br>gat<br>(SEQ ID NO: 13) |
| h.Rhino A89 | ttaaaactgggagtgggttgttcccactcactccacccatgcggtgttgtac<br>tctgttattacggtaactttgtacgccagttttttcccacccttccccataat<br>gtaacttagaagtttgtacaatatgaccaataggtgacaatcatccagactg<br>tcaaaggtcaagcacttctgtttccccggtcaatgaggatatgctttaccca<br>aggcaaaaaccttagagatcgttatccccacactgcctacacagagcccagt<br>accattttgatataattgggttggtcgctccctgcaaacccagcagtagac<br>ctggcagatgaggctggacattccccactggcgacagtggtccagcctgcgt<br>ggctgcctgctcacccttcttgggtgagaagcctaattattgacaaggtgtg<br>aagagccgcgtgtgctcagtgtgcttcctccggcccctgaatgtggctaacc<br>ttaaccctgcagccgttgcccataatccaatgggtttgcggtcgtaatgcgt<br>aagtgcgggatgggaccaactactttgggtgtccgtgtttcctgttttctt<br>ttgattgcattttatggtgacaatttatagtgtatagattgtcatc<br>(SEQ ID NO: 14) |
| Coxsackie B1 | ttaaaacagcctgtgggttgttcccacccacaggcccattgggcgctagcac<br>tctggtatcacggtacctttgtgcgcctgttttacatcccctccccaaattg<br>taatttagaagtttcacacaccgatcattagcaagcgtggcacaccagccat<br>gttttgatcaagcacttctgttaccccggactgagtatcaatagaccgctaa<br>cgcggttgaaggagaaaacgttcgttacccggccaactacttcgaaaaacct<br>agtaacaccatggaagttgcggagtgtttcgctcagcactaccccagtgtag<br>atcaggtcgatgagtcaccgcgttccccacgggcgaccgtggcggtggctgc<br>gttggcggcctgcctacggggaaacccgtaggacgctctaatacagacatgg<br>tgcgaagagtctattgagctagttggtaatcctccggcccctgaatgcggct<br>aatcctaactgcggagcacataccctcaaaccaggggggcagtgtgtcgtaac<br>gggcaactctgcagcggaaccgactactttgggtgtccgtgtttcattttat<br>tcctatactggctgcttatggtgacaattgacaggttgttaccatatagtta<br>ttggattggccatccggtgactaacagagcaattatatatctctttgttggg<br>tttataccacttagcttgaaagaggttaaaacactacatctcatcattaaac<br>taaatacaacaaa<br>(SEQ ID NO: 15) |

TABLE 3

Exemplary Retained cyclization sequences, DNA sequence of the 5' UTR to the beginning of NS1 after the engineered deletions in WNV and YFV. The sequence in bold corresponds to the proposed cyclization sequence after IVT based on previous literature. These are proposed sequences based on previous experimentation and in silico analysis.

| Name | Nucleotide sequence |
|---|---|
| West Nile Replicon | 5' AGTAGTTCGCCTGTGTGAGCTGACAAACTTAGTAGTGTTTGTGAGGATTA<br>ACAACAATTAACACAGTGCGAGCTGTTTCTTAGCACGAAGATCTCGATGTCT<br>AAGAAACCAGGAGGGCCCGGCAAGAGCCGGGCTGTCAATATGCTAAAACGCG<br>GAATGCCCCGCGTGTTGTCCTTGATTGGACTTAAGATGGGCATCAATGCTCG<br>TGATAGGTCCATAGCTCTCACGTTTCTCGCAGTTGGAGGAGTTCTGCTCTTC<br>CTCTCCGTGAACGTGCACGCT-begin NS1 sequence<br>(SEQ ID NO: 16) |

TABLE 3-continued

Exemplary Retained cyclization sequences, DNA sequence of the 5' UTR to the beginning of NS1 after the engineered deletions in WNV and YFV. The sequence in bold corresponds to the proposed cyclization sequence after IVT based on previous literature. These are proposed sequences based on previous experimentation and in silico analysis.

| Name | Nucleotide sequence |
|---|---|
| Yellow Fever Replicon | 5' AGTAAATCCTGTGTGCTAATTGAGGTGCATTGGTCTGCAAATCGAGTTGC TAGGCAATAAACACATTTGGATTAATTTTAATCGTTCGTTGAGCGATTAGCA GAGAACTGACCAGAACATGTCTGGTCGTAAAGCTCAGGGAAAAACCCTGGGC GTCAATATGGTACGACGAGGAGTTCGCTCCTTGTCAAACTCGCGAAACATGA CAATGTCCATGAGCATGATCTTGGTAGGAGTGATCATGATGTTTTTGTCTCT AGGAGTTGGGGCG-begin NS1 sequence (SEQ ID NO: 17) |

TABLE 4

Exemplary retained signal sequences:

| Replicon | Sequence |
|---|---|
| NS1 Signal/Translocation Nucleotide Sequence West Nile Replicon | ATGGGCATCAATGCTCGTGATAGGTCCATAGCTCTCACGTT TCTCGCAGTTGGAGGAGTTCTGCTCTTCCTCTCCGTGAACG TGCACGCT (SEQ ID NO: 18) |
| NS1 Signal/Translocation Peptide Sequence West Nile Replicon | MGINARDRSIALTFLAVGGVLLFLSVNVHA (SEQ ID NO: 19) |
| NS1 Signal/Translocation Nucleotide Sequence Yellow Fever Replicon | GAAACATGACAATGTCCATGAGCATGATCTTGGTAGGAGTG ATCATGATGTTTTTGTCTCTAGGAGTTGGGGCG (SEQ ID NO: 20) |
| NS1 Signal/Translocation Peptide Sequence Yellow Fever Replicon | NMTMSMSMILVGVIMFLSLGVGA (SEQ ID NO: 21) |

TABLE 5

Promoter sequences useful to express a flavivirus RNA:

| Promoter | Sequence |
|---|---|
| T7 promoter Φ 6.5 (traditional) | TAATACGACTCACTATAG<u>A</u>--- (SEQ ID NO: 22) |
| T7 promoter Φ 2.5 | TAATACGACTCACTATT<u>AA</u>--- (SEQ ID NO: 23) |
| T7 promoter Φ 6.5 mut. | TAATACGACTCACTATA<u>AA</u>--- (SEQ ID NO: 24) |
| T7 promoter Φ 2.5 (OL) | TAATACGACTCACTATTA---- (SEQ ID NO: 25) |
| T7 promoter Φ 6.5 mut. (OL) | TAATACGACTCACTATA<u>A</u>---- (SEQ ID NO: 26) |

*in bold is the transcription start site. Underlined is the first nucleotide of the flavivirus 5' UTR. OL indicates that transcription is expected to start on the first nucleotide of the 5' UTR.

The invention claimed is:

1. An isolated nucleic acid, comprising a sequence encoding a (+) strand self-replicating RNA, the self-replicating RNA comprising a flavivirus replicase-coding sequence and a heterologous protein-coding sequence, the heterologous protein coding sequence being disposed between at least two flanking separation sequences, and the self-replicating RNA lacking coding sequence for viral structural proteins capable of forming viral particles,
   (i) wherein the flavivirus replicase is a West Nile Virus (WNV) replicase, wherein the WNV is selected from the group consisting of WNV NY99, WN NY 2000-crow3356, HNY1999, NY99flamingo38299, IS98STD, goose-Hungary/03, Italy1998Equine, RO9750, VLG4, LEIV-Vlg99-27889, PaH001, PaAn001, Eg101, Chin-01, Sarafend, B956 (WNFCG), goshawk-Hungary/04, LEIV-Krnd88-190, Nea Santa-Greece 2010, Goshawk-Hungary/04, Greece/2012/Kavala.39.1, Italy/2013/Rovigo/32.1, and Austria/2008-gh; and
   (ii) wherein each of said separation sequences comprises a viral 2A sequence;
   (iii) wherein said isolated nucleic acid comprises a modified T7 promoter upstream of the 5' end of said self-replicating RNA, wherein said modified T7 promoter comprises a nucleotide sequence of SEQ ID NO: 25 or SEQ ID NO: 26, wherein the last nucleotide of said modified T7 promoter is A which overlaps with the transcription initiation site of said self-replicating RNA; and
   (iv) where said isolated nucleic acid comprises a sequence encoding a ribozyme downstream of the 3' end of said self-replicating RNA.

2. The nucleic acid of claim 1, wherein the replicase comprises an amino acid sequence with at least 60% homology to SEQ ID NO:2.

3. The nucleic acid of claim 1, wherein the at least two flanking separation sequences do not recombine.

4. The nucleic acid of claim 1, wherein said isolated nucleic acid further comprises a restriction enzyme recognition sequence downstream of said ribozyme sequence.

5. The nucleic acid of claim 1, wherein the nucleic acid comprises a sequence at least about 60% identical to SEQ ID NO: 1.

6. The nucleic acid of claim 1, wherein the nucleic acid is a plasmid, wherein the plasmid is a low-copy number plasmid.

7. The nucleic acid of claim 1, wherein the heterologous protein coding sequence is an antigenic protein.

8. The nucleic acid of claim 1, wherein the heterologous protein coding sequence is a therapeutic protein, wherein the therapeutic protein is selected from a growth factor, cytokine, antibody, or antigen-binding fragment of an antibody.

9. The nucleic acid of claim 1, complexed with a delivery system, wherein the delivery system is selected from a viral replicon particle (VRP), a lipid nanoparticle (LNP), a cationic nanoemulsion, or a biodegradeable polymer.

10. A host cell comprising the nucleic acid of claim 1, wherein the host is selected from XL10Gold® ultracompetent cells (Tet$^r$Δ(mcrA)183 Δ(mcrCB-hsdSMR-mrr)173 endA1 supE44 thi-1 recA1 gyrA96 relA1 lac Hte [F' proAB lacI$^q$ZΔM15 Tn10 (Tet$^r$) Amy Cam$^r$] cells) and STELLAR® cells (F-, endA1, supE44, thi-1, recA1, relA1, gyrA96, phoA, Φ80d lacZΔ M15, Δ (lacZYA-argF) U169, Δ (mrr-hsdRMS-mcrBC), ΔmcrA, λ-cells).

11. A self-replicating RNA encoded by the nucleic acid of claim 1.

12. A composition comprising the nucleic acid of claim 1, further comprising an adjuvant, wherein the adjuvant is a metal salt.

13. The composition of claim 12, further comprising a TLR agonist, wherein the TLR agonist is a TLR7 agonist.

* * * * *